US012575745B2

(12) United States Patent
Park

(10) Patent No.: US 12,575,745 B2
(45) Date of Patent: Mar. 17, 2026

(54) OPERATION METHOD FOR MEASURING BIOMETRIC INDEX OF A SUBJECT

(71) Applicant: GB SOFT CO., LTD., Daegu (KR)

(72) Inventor: Ki Bum Park, Daegu (KR)

(73) Assignee: GB SOFT CO., LTD., Daegu (KR)

( * ) Notice: Subject to any disclaimer, the term of this patent is extended or adjusted under 35 U.S.C. 154(b) by 375 days.

(21) Appl. No.: 18/452,862

(22) Filed: Aug. 21, 2023

(65) Prior Publication Data

US 2023/0397826 A1     Dec. 14, 2023

Related U.S. Application Data

(63) Continuation of application No. PCT/KR2022/002699, filed on Feb. 24, 2022.

(30) Foreign Application Priority Data

Feb. 25, 2021     (KR) ........................ 10-2021-0025427

(51) Int. Cl.
*G06T 7/90* (2017.01)
*A61B 5/00* (2006.01)
(Continued)

(52) U.S. Cl.
CPC ........... *A61B 5/021* (2013.01); *A61B 5/1032* (2013.01); *A61B 5/7207* (2013.01); *G06T 5/20* (2013.01);
(Continued)

(58) Field of Classification Search
CPC ..... A61B 5/021; A61B 5/1032; A61B 5/7207; A61B 5/0033; A61B 5/02416; A61B 5/7257; A61B 5/02108; A61B 5/725;
A61B 5/7264; A61B 5/0077; A61B 5/024; A61B 5/7485; A61B 5/4484; A61B 5/7271; A61B 2576/00; A61B 5/0013; A61B 5/02007; A61B 5/02055; A61B 5/0261; G06T 5/20; G06T 5/70; G06T 7/0016; G06T 7/90;
(Continued)

(56) References Cited

U.S. PATENT DOCUMENTS 9,750,420 B1 * 9/2017 Agrawal ................... G06T 7/73
11,103,144 B2 * 8/2021 Park ........................ A61B 5/165
(Continued)

FOREIGN PATENT DOCUMENTS

CN       111759292 A  * 10/2020  ......... A61B 5/02416
KR    10-2015-0059631 A    6/2015
(Continued)

OTHER PUBLICATIONS

International Search Report of PCT/KR2022/002699 Mailed on Jun. 17, 2022.

*Primary Examiner* — Jose L Couso

(57) ABSTRACT

A bio-index measurement method is disclosed. According to an embodiment, a method of measuring a biometric index of a subject using an artificial neural network in a non-contact manner, performed by one or more processors, may be provided. The method of measuring a biometric index of a subject is performed based on capturing an image of the subject, extracting a plurality of color channel values from the image, and obtaining characteristic values indicating the biometric index based on the plurality of color channel values.

15 Claims, 30 Drawing Sheets

OBTAINING A PLURALITY OF IAMGE FRAMES OF A SUBJECT — S2810

OBTAINING FIRST, SECOND, AND THIRD COLOR CHANNEL VALUES — S2820

CALCULATING A FRIST DIFFRENCE VALUE AND A SECOND DIFFERENCE VALUE — S2830

OBTAINING A FIRST CHARACTERISTIC VALUE AND A SECOND CHARACTERISTIC VALUE — S2840

OBTAINING TIME SERIES DATA BASED ON A FIRST CHARACTERISTIC VALUE AND A SECOND CHARACTERISTIC VALUE — S2850

OBTAINING BIOMETRIC CHARACTERISTIC DATA BSED ON TIME SERIES DATA — S2860

OBTAINIG BIOMETRIC INDEX OF A SUBJECT USING BIOMETRIC IDNEX OBTAINING MODEL BASED ON BIOMETRIC CHARACTERISTIC DATA — S2870

(51) Int. Cl.

| | |
|---|---|
| *A61B 5/021* | (2006.01) |
| *A61B 5/103* | (2006.01) |
| *G06T 5/20* | (2006.01) |
| *G06T 5/70* | (2024.01) |
| *G06T 7/00* | (2017.01) |
| *G16H 50/30* | (2018.01) |

(52) U.S. Cl.
CPC .............. *G06T 5/70* (2024.01); *G06T 7/0016* (2013.01); *G06T 7/90* (2017.01); *G16H 50/30* (2018.01); *G06T 2207/10024* (2013.01); *G06T 2207/20056* (2013.01); *G06T 2207/20084* (2013.01); *G06T 2207/30088* (2013.01)

(58) Field of Classification Search
CPC . G06T 2207/10024; G06T 2207/20056; G06T 2207/20084; G06T 2207/30088; G06T 2207/20081; G06T 2207/20216; G06T 2207/30076; G06T 2207/10016; G06T 3/4046; G06T 5/60; G06T 9/002; G06T 2207/20076; G16H 50/30; G16H 50/20; G16H 30/20; G16H 30/40; G16H 40/67; G16H 50/70; G06V 40/169; G06V 10/26; G06V 10/56; G06V 10/763; G06V 40/1388; G06V 40/15; G06V 40/162; G06V 40/45; G06V 10/454; G06V 10/54; G06V 10/7764; G06V 10/774; G06V 10/82; G06V 10/84; G06V 20/41; G06V 30/18057; G06V 20/698; G06V 30/19173; G06V 30/194; G06N 3/02; G06N 3/08–088; G06N 3/0445; G06N 3/0454; G06N 3/0464; G06N 3/4046; G06N 3/4053; G06N 7/00; G06N 7/01; G06N 20/00; G06K 7/1482; G06F 18/214; G06F 18/22; G06F 18/241; G06F 18/24; G06F 18/2411; G06F 18/2415; G06F 30/27; Y10S 128/925

See application file for complete search history.

(56) References Cited

U.S. PATENT DOCUMENTS

| | | | |
|---|---|---|---|
| 12,023,133 B2 * | 7/2024 | Park ....................... | G16H 40/63 |
| 12,249,176 B2 * | 3/2025 | Park ................... | G06V 40/1365 |
| 2013/0274610 A1 * | 10/2013 | Kamshilin ......... | A61B 5/02416 |
| | | | 600/479 |
| 2014/0192177 A1 * | 7/2014 | Bartula ................. | G06T 7/0016 |
| | | | 348/77 |
| 2015/0148687 A1 | 5/2015 | Kitajima et al. | |
| 2015/0366456 A1 * | 12/2015 | Takamori ............. | A61B 5/0077 |
| | | | 600/479 |
| 2016/0343135 A1 | 11/2016 | De Haan et al. | |
| 2017/0172434 A1 * | 6/2017 | Amelard .............. | A61B 5/7278 |
| 2018/0042486 A1 * | 2/2018 | Yoshizawa ......... | A61B 5/02125 |
| 2018/0214088 A1 * | 8/2018 | Newberry ........... | A61B 5/6817 |
| 2019/0150763 A1 * | 5/2019 | Gladshtein ........... | A61B 3/1241 |
| 2020/0060584 A1 * | 2/2020 | Musin ............... | A61B 5/02055 |

FOREIGN PATENT DOCUMENTS

| | | | | |
|---|---|---|---|---|
| KR | 10-2017-0027468 A | 3/2017 | | |
| KR | 10-2018-0007425 A | 1/2018 | | |
| KR | 10-2020-0079691 A | 7/2020 | | |
| KR | 20200139047 A | * 12/2020 | .......... | G06V 40/168 |

* cited by examiner

BIOMETRIC INDES OBTAINING DEVICE — 10

SERVER — 20

IMAGE OBTAINING DEVICE — 30

SERVER — 20

Figure 4:
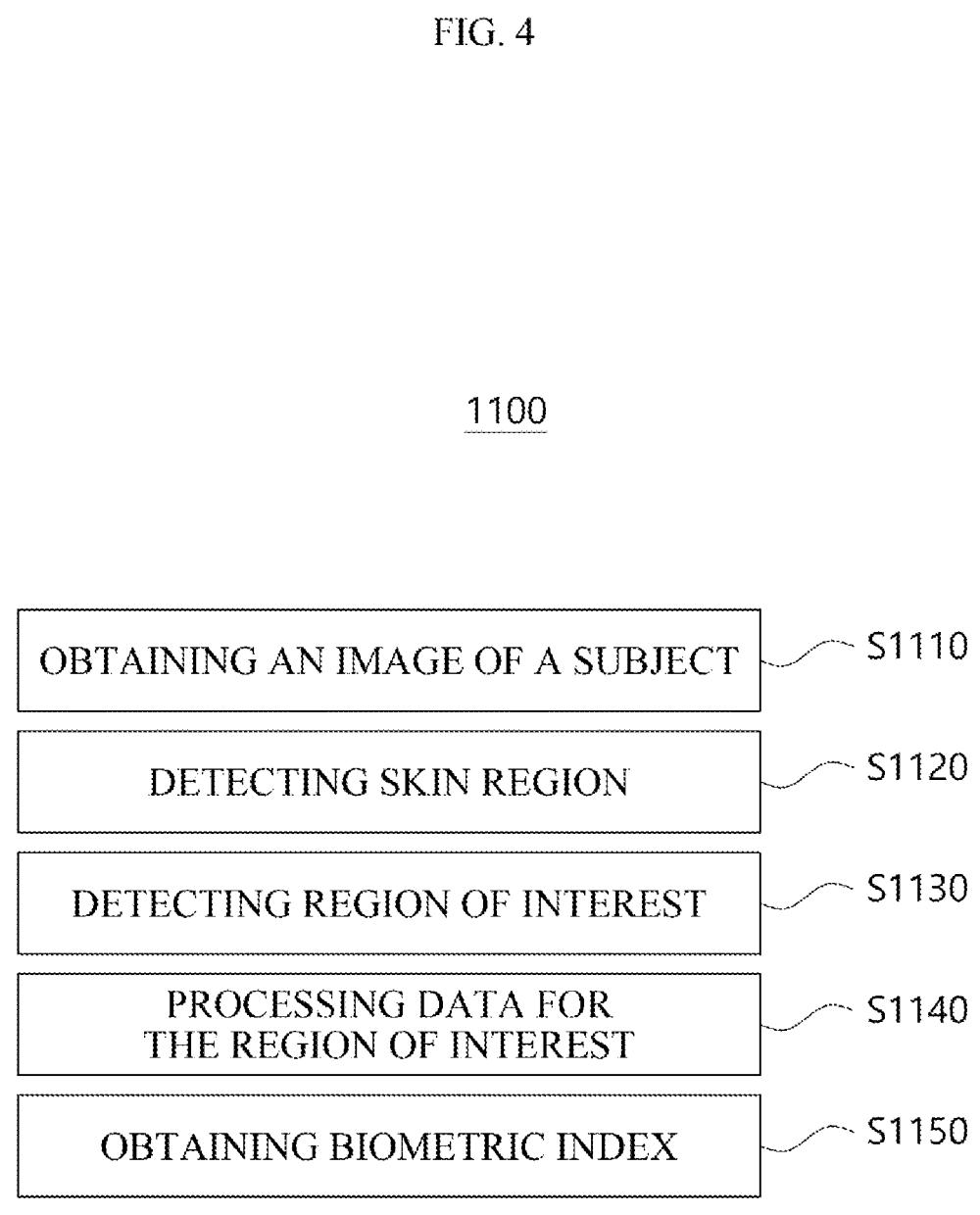

| | |
|---|---|
| OBTAINING AN IMAGE OF A SUBJECT | S1110 |
| DETECTING SKIN REGION | S1120 |
| DETECTING REGION OF INTEREST | S1130 |
| PROCESSING DATA FOR THE REGION OF INTEREST | S1140 |
| OBTAINING BIOMETRIC INDEX | S1150 |

FIG. 5
1160
1161
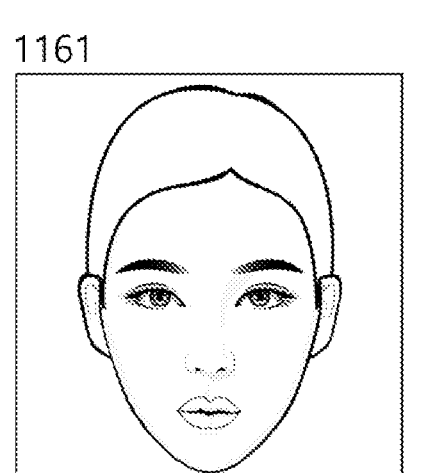
1164
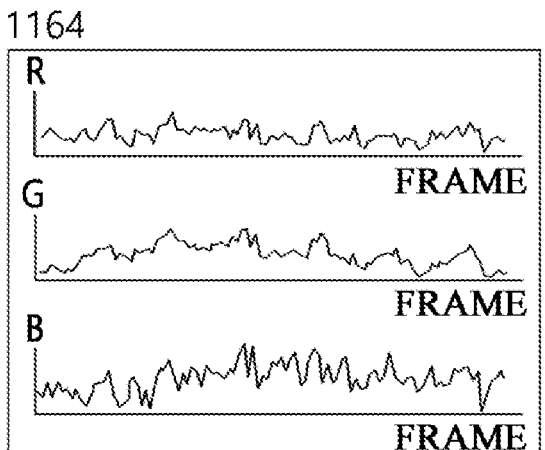
1162
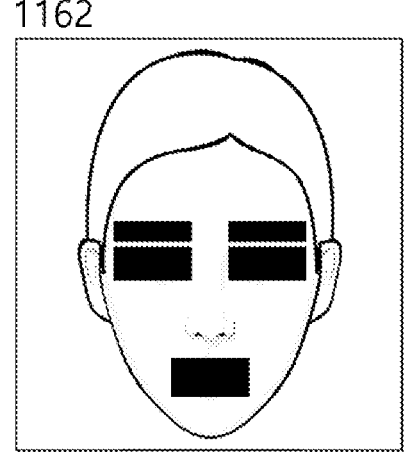
1165
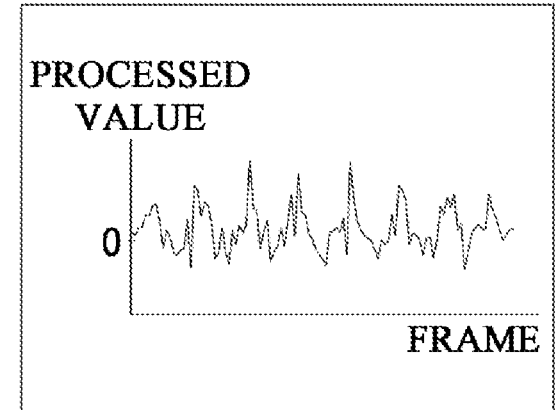
1163
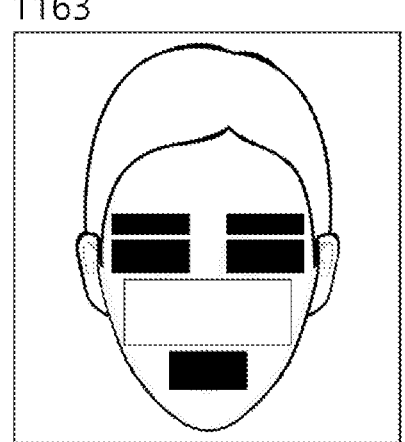
1166
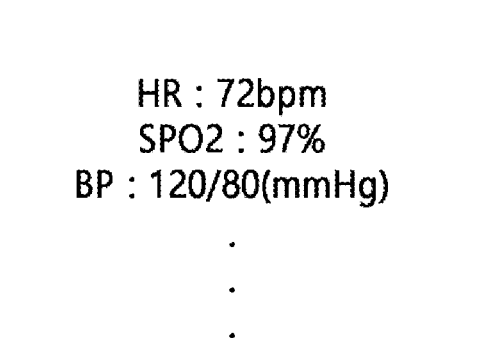

Figure 6:
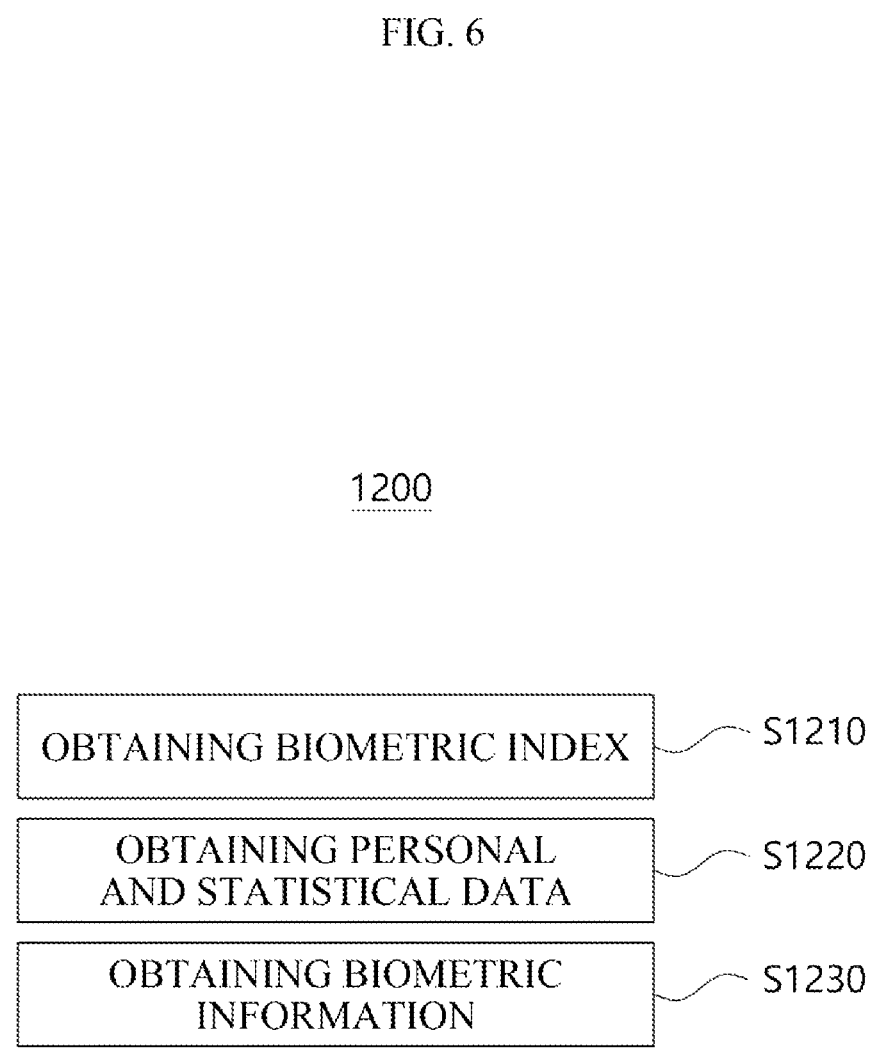

| OBTAINING BIOMETRIC INDEX | S1210 |

| OBTAINING PERSONAL AND STATISTICAL DATA | S1220 |

| OBTAINING BIOMETRIC INFORMATION | S1230 |

1301 — IMAGE 1300    1302 — BIOMETRIC INDEX OBATINING MODEL

Figure 7:
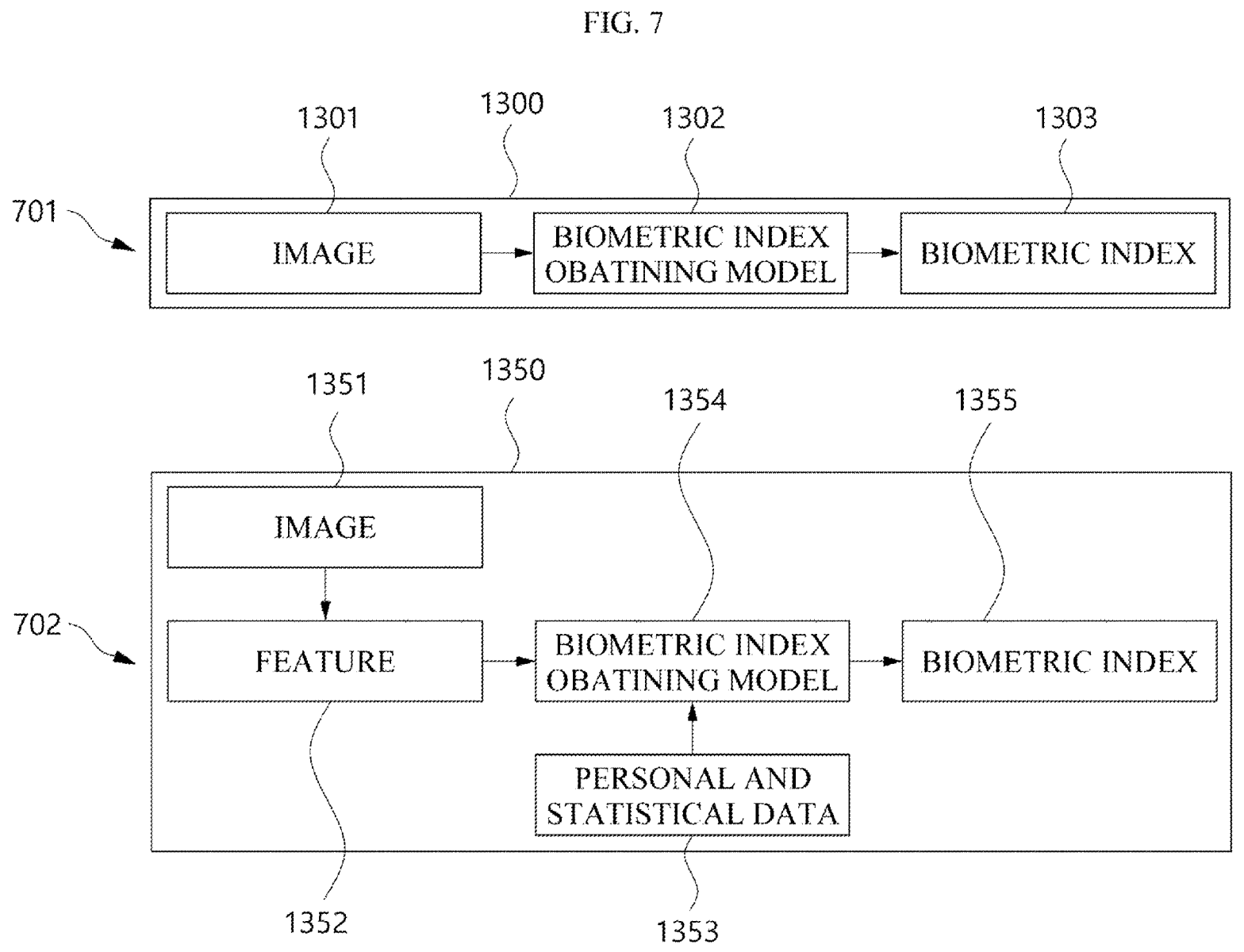

1303 — BIOMETRIC INDEX

702

1351 — IMAGE

1352 — FEATURE 1350    1354 — BIOMETRIC INDEX OBATINING MODEL

1353 — PERSONAL AND STATISTICAL DATA

1355 — BIOMETRIC INDEX

Figure 12:
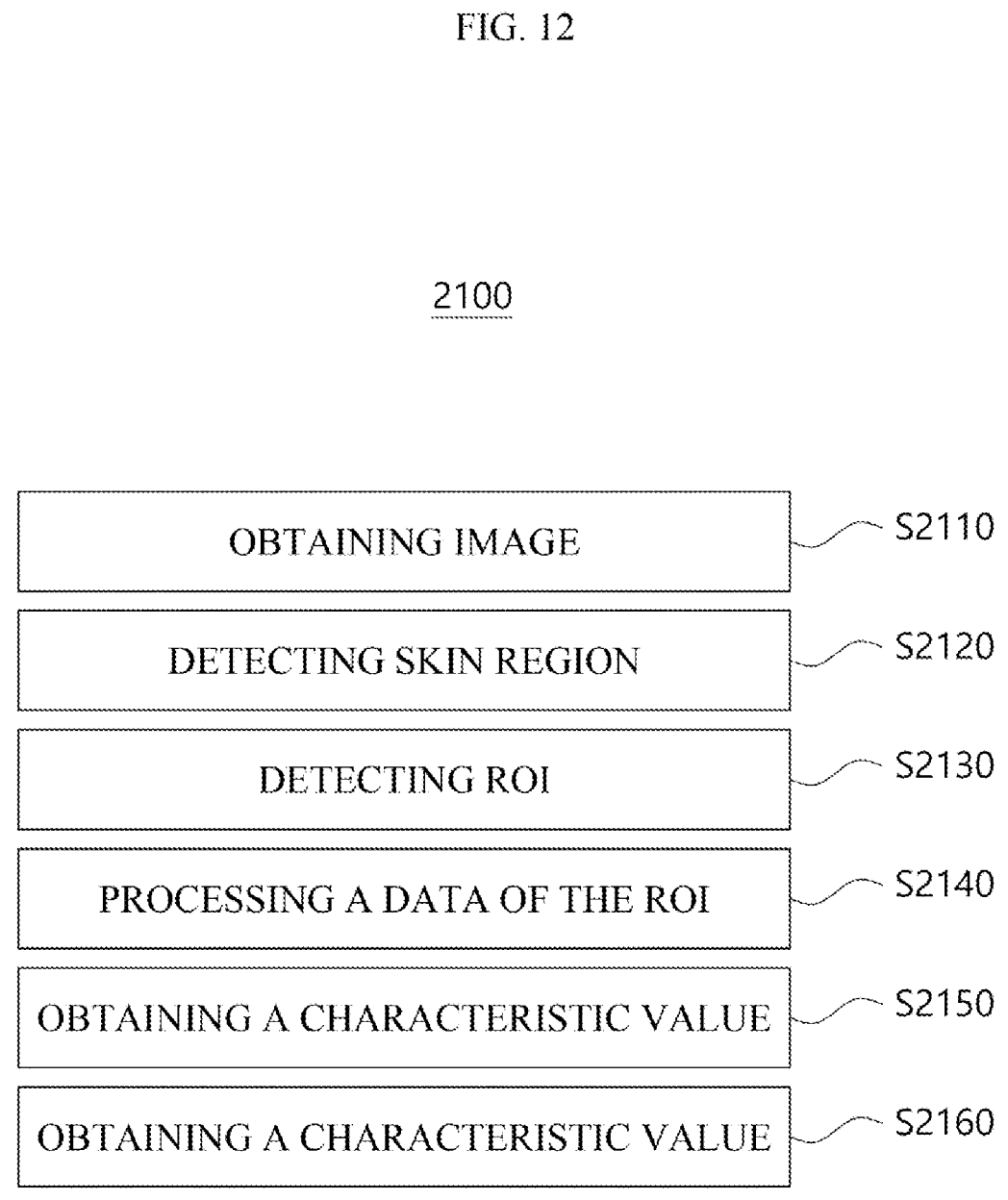

| | |
|---|---|
| OBTAINING IMAGE | S2110 |
| DETECTING SKIN REGION | S2120 |
| DETECTING ROI | S2130 |
| PROCESSING A DATA OF THE ROI | S2140 |
| OBTAINING A CHARACTERISTIC VALUE | S2150 |
| OBTAINING A CHARACTERISTIC VALUE | S2160 |

FIG. 14
1401
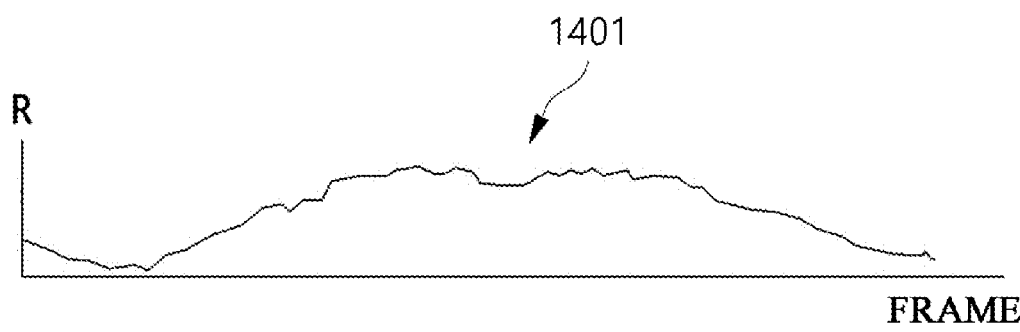
1402
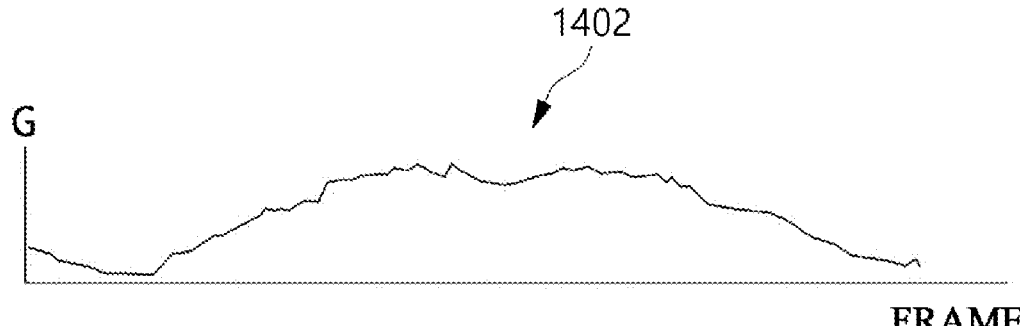
1403
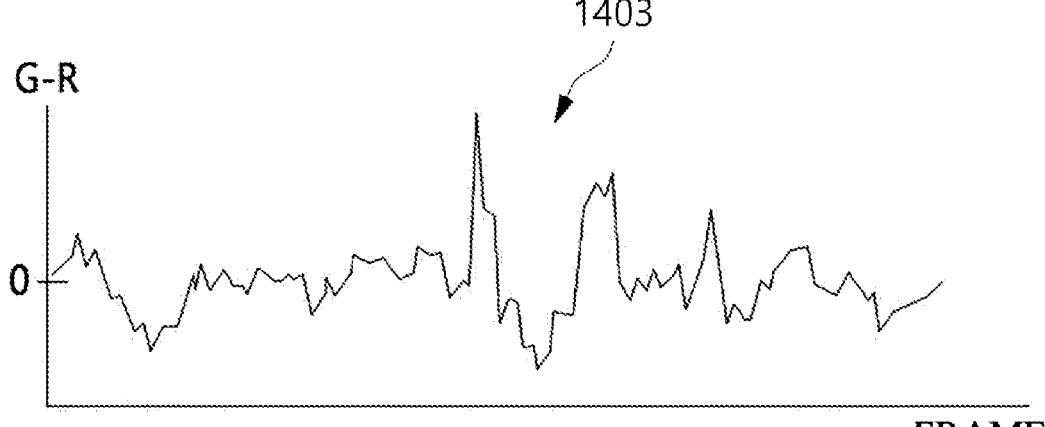

FIG. 16
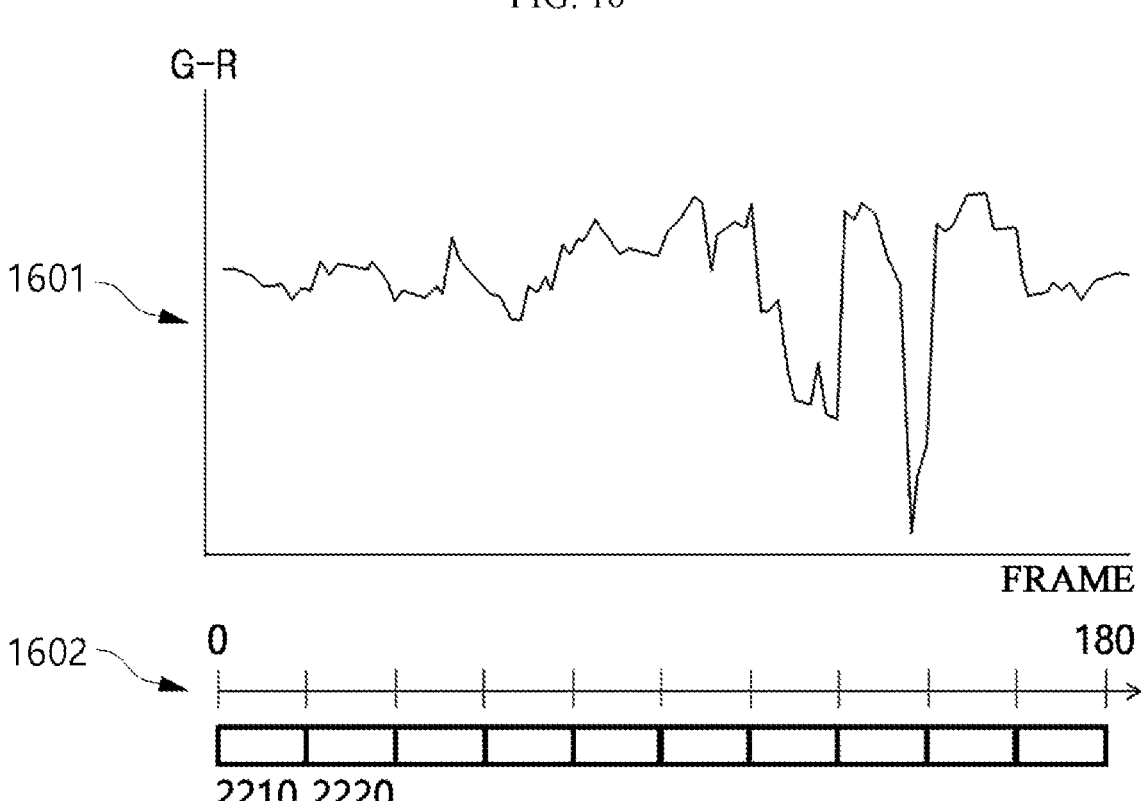
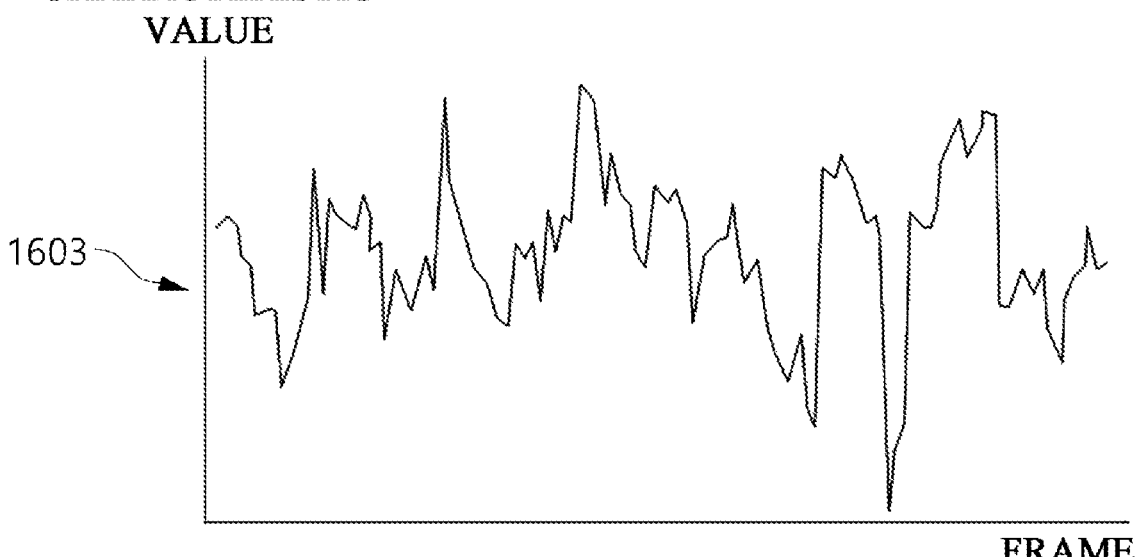

FIG. 18
--------- FIRST CHARACTERISTIC VALUE
-------- SECOND CHARACTERISTIC VALUE
1801
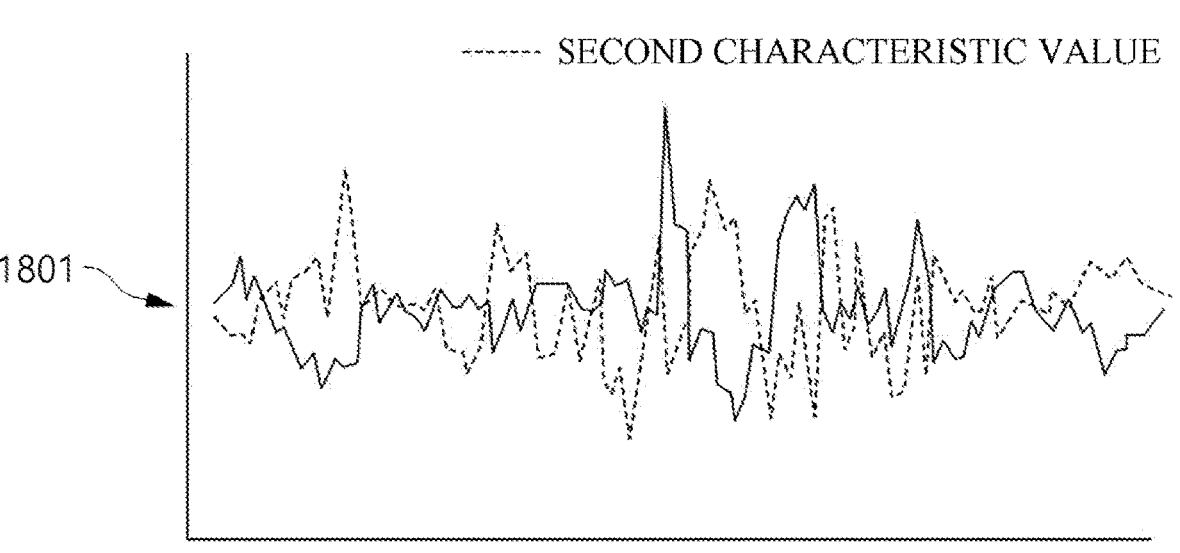
FRAME
THIRD
CHARACTERISTIC
VALUE
1802
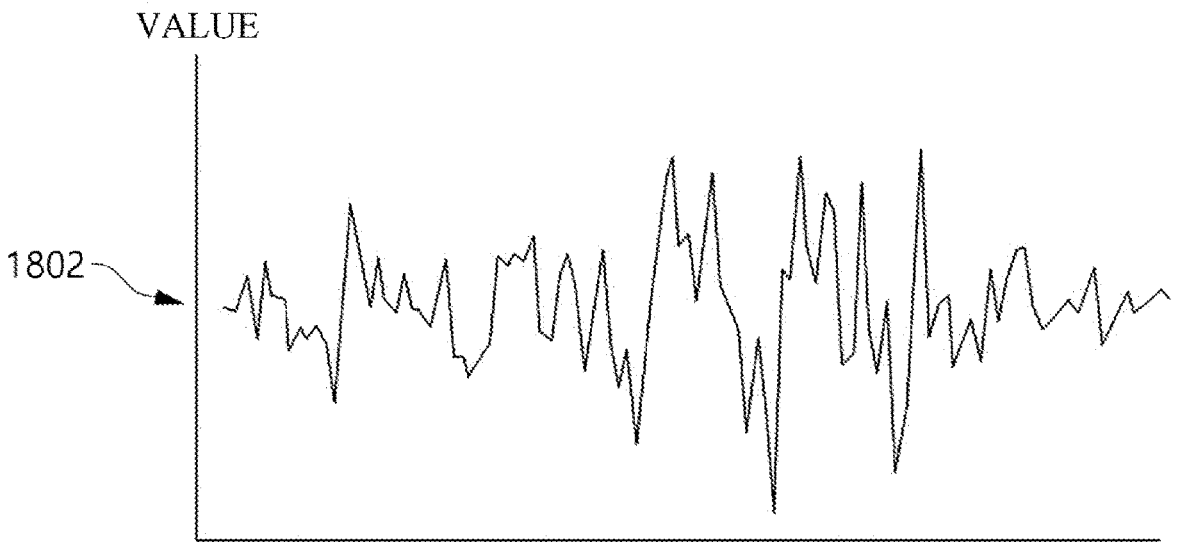
FRAME FREQUENCY (Hz)

1.2

2500

S2510 — OBTAINING FIRST HEART RATE

S2520 — COMPARING A DIFFERENCE BETWEEN THE FIRST HEART RATE AND A HEART RATE AT A FRST TIME POINT WITH A REFRENCE VALUE

S2531 — OUTPUTING THE FIRST HERAT RATE AS A HERAT RATE AT A SECODN TIME POINT

S2532 — OUTPUTING A HEART RATE CORRECTED FROM THE FIRST HERAT RATE AS A HERAT RATE AT A SECODN TIME POINT

Figure 25:
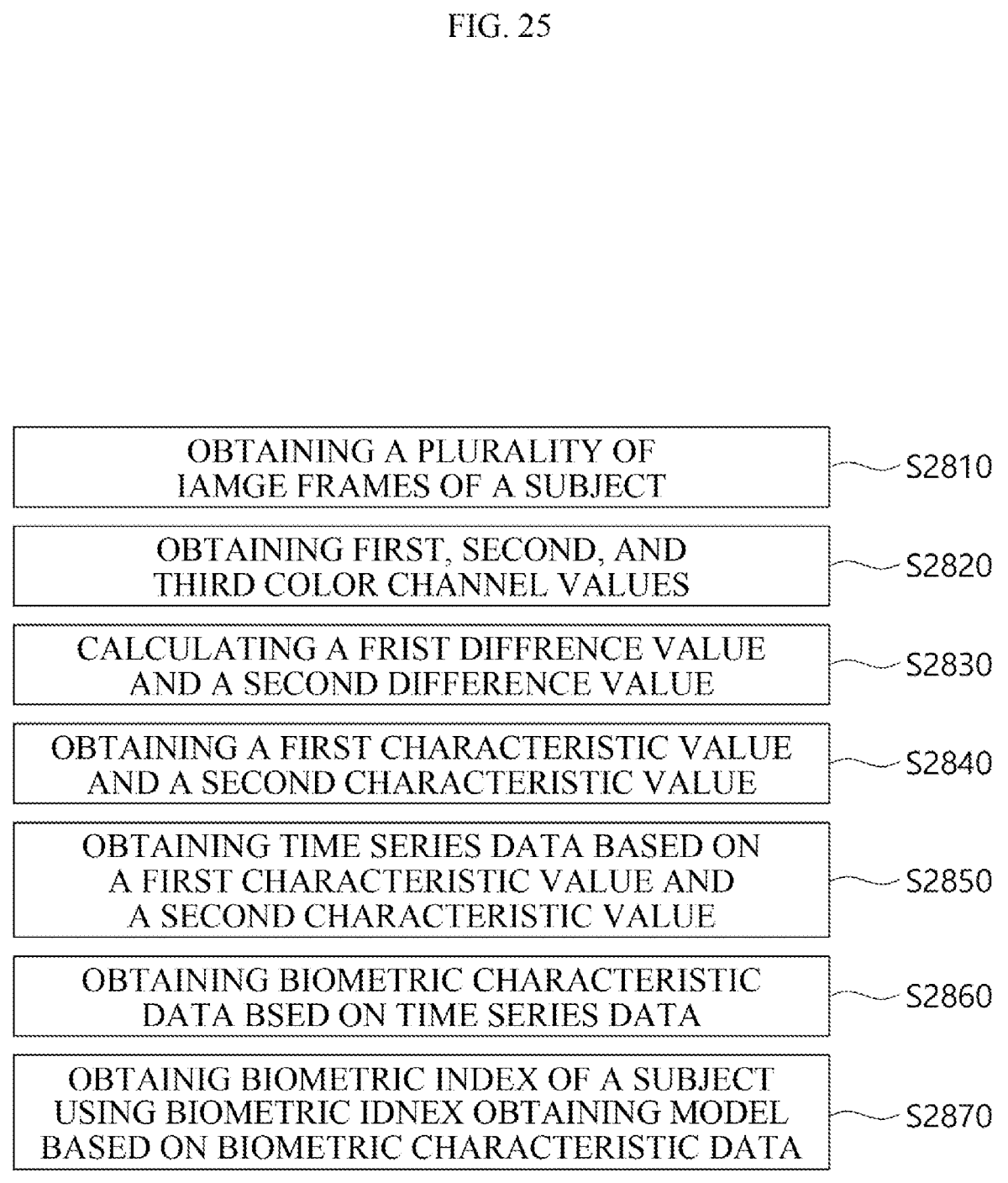

OBTAINING A PLURALITY OF
IAMGE FRAMES OF A SUBJECT     ∽ S2810

OBTAINING FIRST, SECOND, AND
THIRD COLOR CHANNEL VALUES     ∽ S2820

CALCULATING A FRIST DIFFRENCE VALUE
AND A SECOND DIFFERENCE VALUE     ∽ S2830

OBTAINING A FIRST CHARACTERISTIC VALUE
AND A SECOND CHARACTERISTIC VALUE     ∽ S2840

OBTAINING TIME SERIES DATA BASED ON
A FIRST CHARACTERISTIC VALUE AND
A SECOND CHARACTERISTIC VALUE     ∽ S2850

OBTAINING BIOMETRIC CHARACTERISTIC
DATA BSED ON TIME SERIES DATA     ∽ S2860

OBTAINIG BIOMETRIC INDEX OF A SUBJECT
USING BIOMETRIC IDNEX OBTAINING MODEL
BASED ON BIOMETRIC CHARACTERISTIC DATA     ∽ S2870

FIG. 27
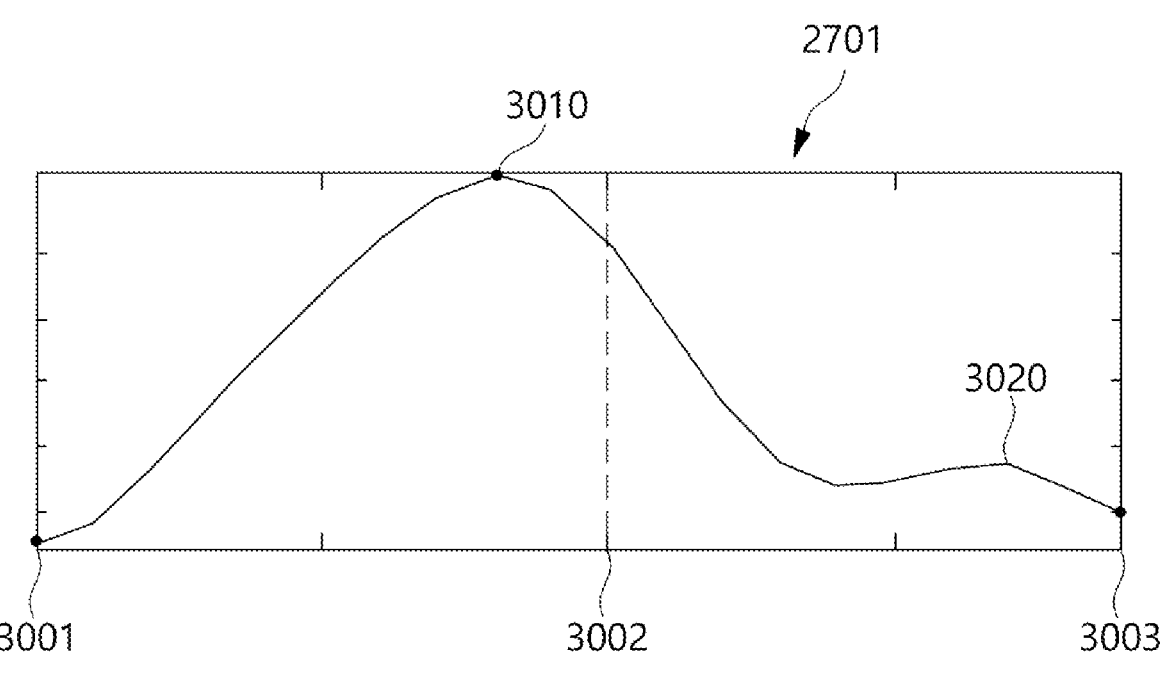
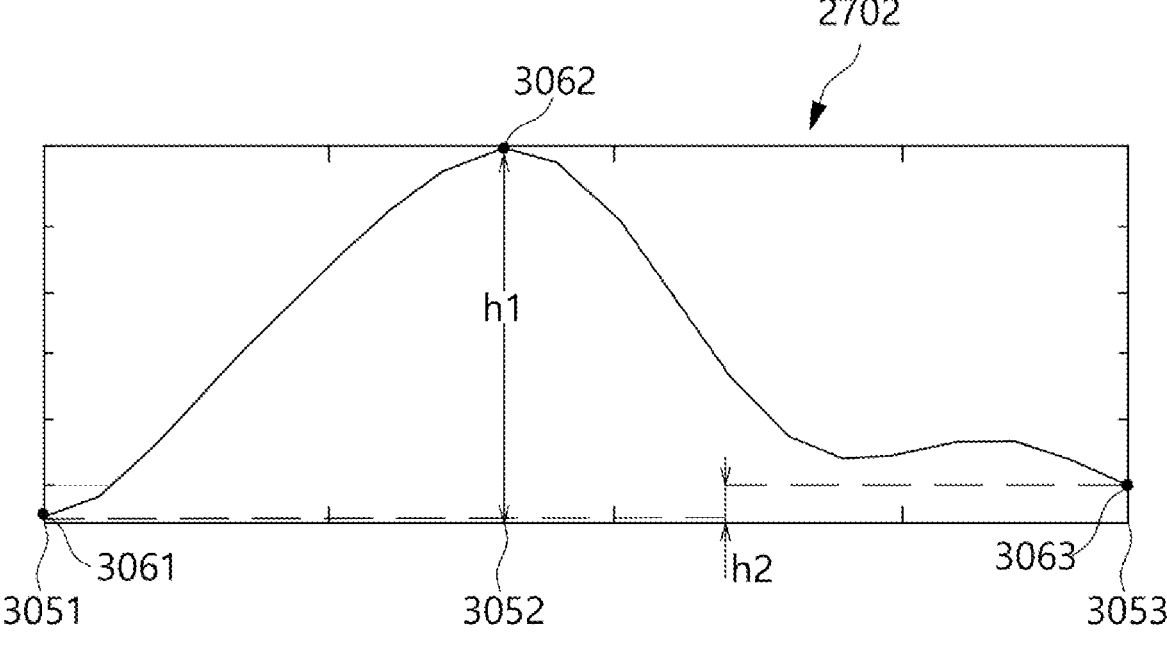

OPERATION METHOD FOR MEASURING BIOMETRIC INDEX OF A SUBJECT

CROSS-REFERENCE TO RELATED APPLICATIONS

This application is a bypass continuation of International PCT Application No. PCT/KR2022/002699, filed on Feb. 24, 2022, which claims priority to Republic of Korea Patent Application No. 10-2021-0025427, filed on Feb. 25, 2021, which are incorporated by reference herein in their entirety.

BACKGROUND

1. Field

Plethysmography is a technique for measuring and analyzing such changes when the volume changes as organs or blood vessels of a human body flows to blood vessels, and the shape of the blood vessels changes naturally.

2. Description of Related Art

The most common technique for measuring photoplethysmography (PPG) using light is explained by the Beer-Lambert law that a method of analyzing the amount of light transmitted to light irradiated to a human body is used, and the absorbance is proportional to the concentration of a substance absorbed and the thickness of an absorbing layer. According to this law, since the change in the transmitted light is a signal proportional to the change in the volume of the transmitted substance, the heart state may be determined using the PPG even when the absorbance of the substance is not known.

Recently, one step of the technique using PPG and a technique using remote photoplethysmography (rPPG) have been developed. As a most popular technique for determining a signal related to heartbeat using PPG, a technique for directly illuminating a camera and a device having a light attached to a nearby distance such as a smartphone by directly contacting a human body to obtain PPG by measuring the transmitted light, a technique related to remote photoplethysmography (rPPG) for determining a change in the volume of a blood vessel from a signal obtained from an image captured by a camera has been continuously researched and developed.

The technique using rPPG is not necessary to contact a subject and a measurement device, and thus may be variously applied to devices and places including a camera such as an airport access and entrance management center and a remote medical treatment.

However, the technique related to rPPG has a large influence on a signal of noise generated by ambient light and a movement of the subject during a process of capturing the subject using the camera, and thus a technique for extracting only a signal related to the change in the volume of the measurement subject from the captured image is considered a key technique among the techniques for measuring a biosignal using rPPG.

SUMMARY

The object to be solved according to an embodiment is to obtain a biometric index by a non-contact method.

The object to be solved according to another embodiment is to reduce noise according to a motion of a subject in order to obtain a biometric index.

The object to be solved according to another embodiment is to reduce noise according to a change in intensity of external light in order to obtain a biometric index.

The object to be solved according to the other embodiment is to obtain a biometric index in a non-contact manner using an artificial neural network.

According to an embodiment, a method of measuring a biometric index of a subject using an artificial neural network in a non-contact manner, performed by one or more processors, includes acquiring a plurality of image frames of the subject; obtaining a first color channel value, a second color channel value, and a third color channel value for at least one image frame included in the plurality of image frames; Calculating a first difference value and a second difference value based on the first color channel value, the second color channel value, and the third color channel value with respect to at least one image frame included in the plurality of image frames Step—the first difference value is a difference value between the first color channel value and the second color channel value for the same image frame, and the second difference value is the first color channel value for the same image frame and the second color channel value for the same image frame. Indicates a difference value between third color channel values—; obtaining a first characteristic value based on the first difference value of at least one image frame included in the first image frame group with respect to a first image frame group acquired during a first preset time period; obtaining a second characteristic value based on a second difference value for at least one image frame included in the first image frame group; obtaining time-series data based on the first characteristic value and the second characteristic value; acquiring bio-signal characteristic data based on the time-series data; and obtaining a biometric index of the subject by using a biometric index obtaining model based on the biosignal feature data.

According to an embodiment of the present invention, a method of obtaining a biometric index by non-contacting may be provided.

According to another embodiment of the present invention, a method of reducing noise according to movement of a subject may be provided.

According to the other embodiment of the present invention, a method of reducing noise according to a change in intensity of an external light may be provided.

According to the other embodiment of the present invention, a method of obtaining a biometric index by non-contacting using an artificial neural network may be provided.

BRIEF DESCRIPTION OF THE DRAWINGS

FIG. 1 is a diagram related to a biometric index and a biometric information management system according to an embodiment.

FIG. 2 is a diagram related to a biometric index and a biometric information management system according to another embodiment.

FIG. 4 is a flowchart illustrating a biometric index obtaining method according to an embodiment.

FIG. 5 is a diagram illustrating a biometric index obtaining method according to an embodiment.

FIG. 6 is a flowchart illustrating a biometric information obtaining method according to an embodiment.

FIGS. 7 and 8 are diagrams for describing a biometric index obtaining method using a biometric index obtaining model.

FIG. 12 is a flowchart illustrating a heart rate obtaining method according to an embodiment.

FIG. 14 is a graph illustrating a noise reduction method according to an embodiment.

FIG. 16 is a diagram illustrating a characteristic value obtaining method according to an embodiment.

FIG. 18 is a diagram illustrating a method of using a plurality of characteristic values.

FIG. 25 is a flowchart illustrating a biometric index obtaining method according to an embodiment.

FIG. 27 is a diagram illustrating target time series data according to an embodiment.

DETAILED DESCRIPTION

Figure 3:
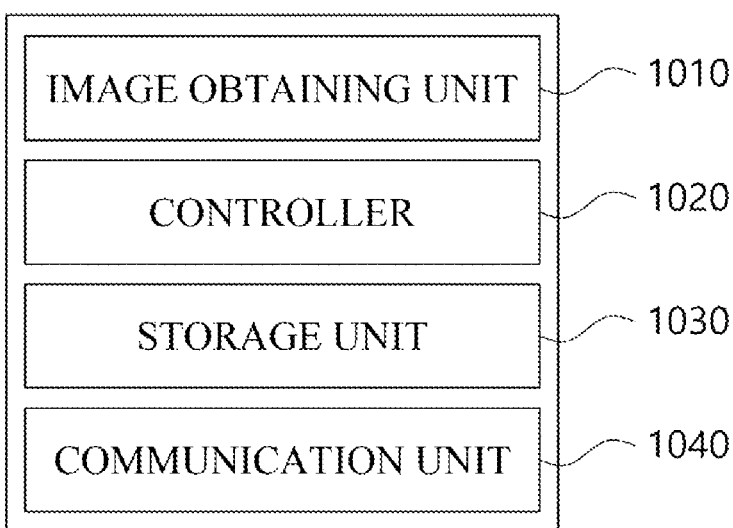
FIG. 3 is a diagram for describing a biometric index obtaining device according to an embodiment.

The embodiments described herein are for clearly illustrating the spirit of the present invention to those skilled in the art, and the present invention is not limited to the embodiments described herein, and the scope of the present invention should be interpreted as including modifications or variations that do not depart from the spirit of the present invention.

The terms used herein have selected general terms that are widely used in the present invention, but they may vary depending on the intention of a person skilled in the art, precedent, or the appearance of new technologies. However, in contrast, when a specific term is defined and used in arbitrary meanings, the meaning of the term will be separately described. Therefore, the terms used herein should be interpreted based on the substantial meanings of the terms and the contents throughout this specification rather than a simple name of the terms.

The drawings attached to the present specification are for easy description of the present invention, and the shapes illustrated in the drawings may be exaggerated as necessary to help understand the present invention, and thus the present invention is not limited by the drawings.

In the present specification, when it is judged that a detailed description of a known configuration or function related to the present invention may make the gist of the present invention ambiguous, a detailed description thereof will be omitted as necessary.

According to an embodiment, a method of measuring a biometric index of a subject using an artificial neural network in a non-contact manner, performed by one or more processors, may include: obtaining a plurality of image frames of the subject; obtaining a first color channel value, a second color channel value, and a third color channel value with respect to at least one image frame included in the plurality of image frames; calculating a first difference value and a second difference value with respect to at least one image frame included in the plurality of image frames based on the first color channel value, the second color channel value, and the third color channel value, wherein the first difference value is a difference value between the first color channel value and the second color channel value with respect to a same image frame, and the second difference value indicates a difference value between the first color channel value and the third color channel value with respect to a same image frame; obtaining a first characteristic value with respect to a first image frame group obtained for a first predetermined time based on the first difference value with respect to at least one image frame included in the first image frame group; obtaining a second characteristic value with respect to at least one image frame included in the first image frame group based on the second difference value; obtaining time series data based on the first characteristic value and the second characteristic value; obtaining biosignal characteristic data based on the time series data; and obtaining a biometric index of the subject using a biometric index obtaining model based on the biosignal characteristic data.

The obtaining of the bio-signal feature data based on the time series data may include: filtering the time series data using a band pass filter; and obtaining the bio-signal feature data using the filtered time series data.

The filtering of the time series data using the band pass filter may include filtering the time series data using a band pass filter having a frequency band corresponding to a heart rate of the subject.

The filtering of the time series data using the band pass filter corresponding to the heart rate of the subject may include extracting a frequency band corresponding to the heart rate of the subject by performing Fourier transform on the time series data.

The obtaining of the bio-signal characteristic data based on the time series data may include: dividing the time series data into a plurality of detailed time series data; and extracting a target time series data based on the divided time series data, wherein the target time series data may include a first maximum value and a second maximum value smaller than the first maximum value.

The bio-signal characteristic data may be generated based on at least one of a value at a start time point of the target time series data, the first maximum value, and a value at an end time point of the target time series data.

The bio-signal characteristic data may be generated based on time series data obtained by dividing the target time series data into first differentials and time series data obtained by dividing the target time series data into second differentials.

The biometric index for the subject may include at least one of a lowest blood pressure or a highest blood pressure of the subject.

The first, second, and third color channels may be color channels according to RGB color space.

The first color channel may be set to a Green channel, the second color channel may be set to a Red channel, and the third color channel may be set to a Blue channel.

The first characteristic value may be obtained based on a first deviation value of the first difference value for at least one image frame included in the first image frame group, the second characteristic value may be acquired based on a second deviation value of the second difference value for at least one image frame included in the first image frame group, the first deviation value may be calculated based on an average value of the first difference value for the first image frame group and the first difference value for the at least one image frame, and the second deviation value may be calculated based on an average value of the second difference value for the first image frame group and the second difference value for the at least one image frame.

The first characteristic value and the second characteristic value may be normalized values.

The first characteristic value may be a value normalized by a first standard deviation value, the second characteristic value may be a value normalized by a second standard deviation value, and the first standard deviation value may be a standard deviation value of the first difference value for the first image frame group, and the second standard deviation value may be a standard deviation value of the second difference value for the first image frame group.

The time series data may be obtained based on third characteristic data obtained as a sum of the first characteristic value and the second characteristic value.

0. Definition of Terms

The term "measurement" used in the present specification may be understood to include all of determining by reading, determining by speculating, and measuring a size of other amounts based on a predetermined amount.

The "heart rate" used in the present specification may be understood as the number of heart rates, and this may be understood as a concept including both the concept of "heart rate" that may mean the number of hearts measured near the heart as a result of heart rates, and the concept of "pulse" that may mean that vibrations generated as a result of heart rates have propagated to the peripheral blood vessels.

The "blood pressure" used in the present specification may be understood as a pressure generated in the blood vessel when blood is pushed from the heart, and this may be understood as a value that can be estimated as a value that can be understood as a normal "blood pressure", e.g., a value measured by the blood vessel arm arteries, regardless of a measurement site.

The "oxygen saturation" used in the present specification may be understood as a degree of saturation of oxygen in the blood, and more specifically, a fraction of oxygen hemoglobin to total hemoglobin in the blood.

The "core temperature" used in the present specification may be understood as a temperature of a body of a human or animal, and may be understood differently from the "skin temperature" that can be measured in the skin.

The "skin temperature" used in the present specification may be understood as a surface temperature of the skin to be measured.

The "image" used in the present specification may be understood as a concept including all of a plurality of images included in one image or an image.

The "color channel" used in the present specification may be understood as a respective axis constituting a color space, and for example, the Red channel, the Green channel, and the Blue channel may mean the Red axis, the Green axis, and the Blue axis constituting the RGB color space, and the color channel may be configured in two dimensions or may be configured in three dimensions or four dimensions.

The "image of a measured person" used in the present specification may be understood as an image including a position of a measured person to be measured, and for example, when the position of the measured person is a face of the measured person, the image may be understood as an image including a face area of the measured person.

The "personal and statistical data" used in the present specification may mean personal and statistical data that can be collected by the measured person such as age, gender, height, and weight, and may mean personal and statistical data that can be observed such as a facial expression of the measured person, wrinkles, and face color, and may mean personal and statistical data that can be numerated such as statistical data calculated for a group including the measured person or related to the measured person (e.g., 20s average blood pressure, average skin color of yellow persons, average height of 30s males, average weight of Korean males, and the like).

The "time series data" used in the present specification may mean data arranged along a time axis, but is not limited thereto, may mean data arranged along an image frame axis that can correspond to time, may mean data arranged along a time axis or an image frame axis, and may be understood as normal "time series data".

1. Biometric Index and Biometric Information Management System

The "biometric index" may refer to a result of biometric activity of a human body that may be measured or estimated, and may include, for example, heart rate, oxygen saturation, blood pressure, body temperature, blood flow rate, and the like, but is not limited thereto, and may refer to other results of biometric activity of a human body that may be measured or estimated.

The "biometric information" may refer to a result of biometric activity of a human body such as a biometric index and information that may be calculated by considering at least some of personal and statistical data such as facial expression, posture, age, and the like, and may include, for example, sleepiness information, stress information, excitability information, emotional information, and the like, but is not limited thereto.

The biometric index and biometric information management system may refer to a management system that may store, share, or analyze a biometric index that may be measured or estimated and biometric information that may be calculated, and may comprehensively manage a health of an individual using the biometric index and biometric information management system.

Figure 1:
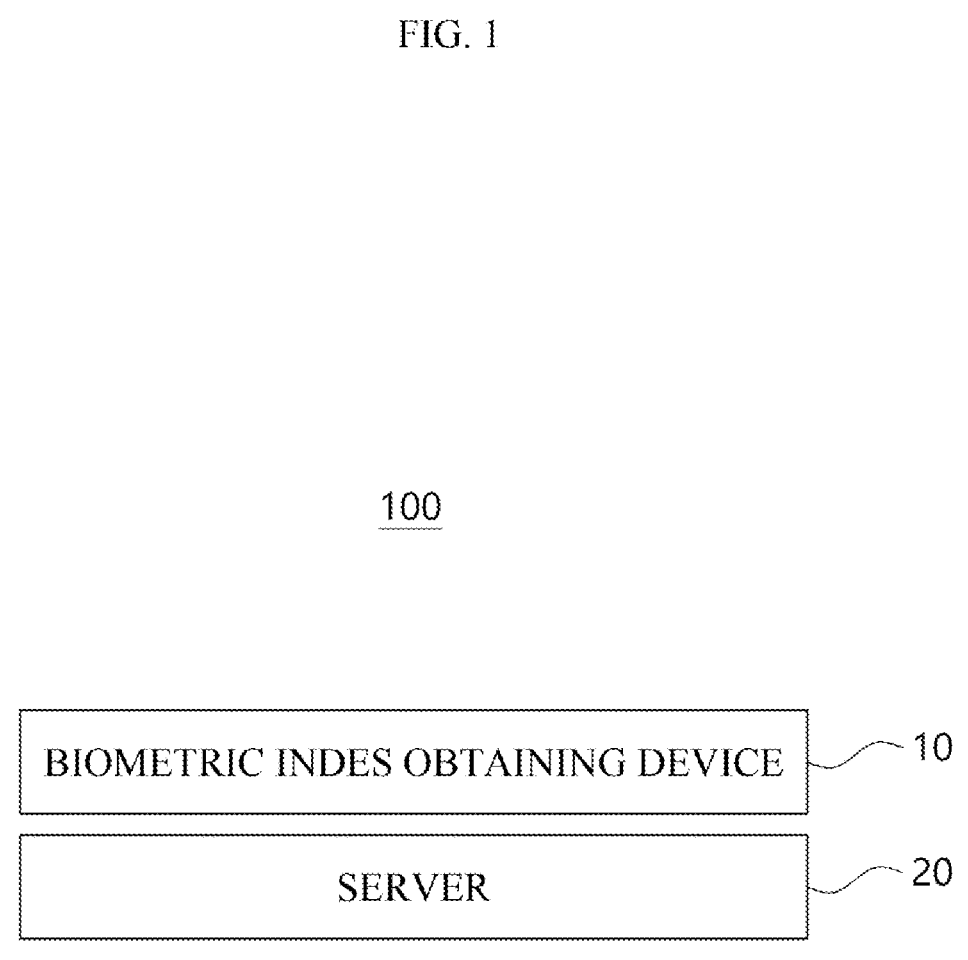
Figure 2:
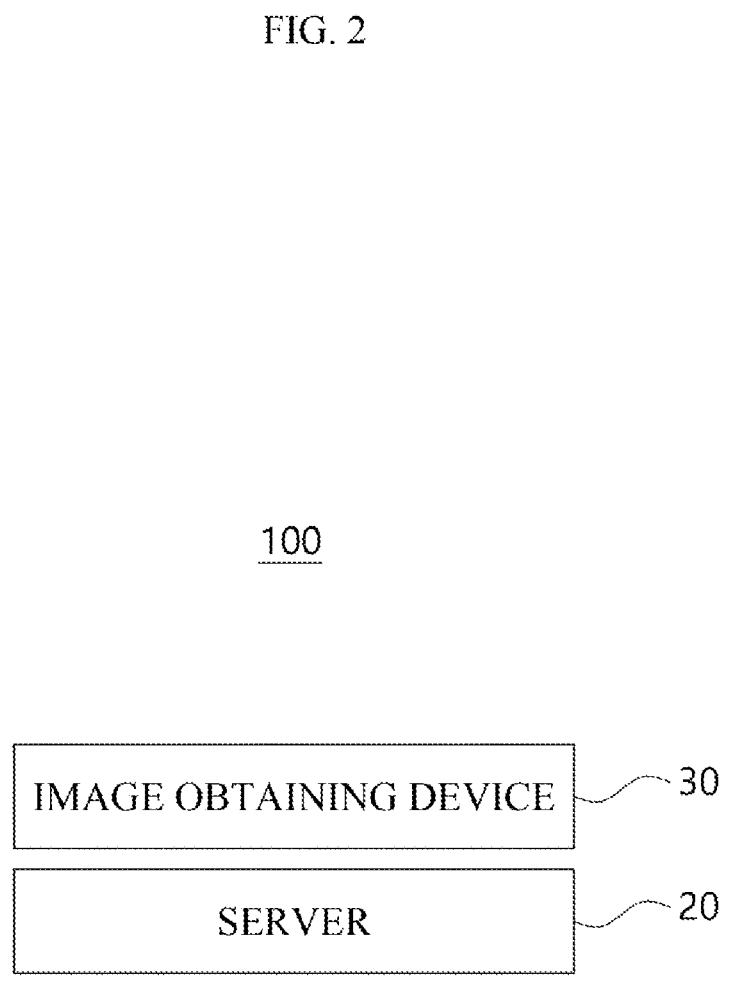

FIGS. 1 and 2 are diagrams illustrating a biometric index and biometric information management system according to an embodiment, respectively.

Referring to FIG. 1, a biometric index and biometric information management system 100 according to an embodiment may include a biometric index acquisition device 10 and a server 20.

In this case, the biometric index obtaining device 10 may measure a biometric index of a subject. More specifically, the biometric index obtaining device 10 may invasively measure the parameter of the subject, measure the biometric index of the subject in a non-chip invasive but contacting manner, or measure the biometric index of the subject in a non-contact manner, or the like.

For example, the biometric index obtaining device 10 may analyze an image or an image of the subject and measure a biometric index such as heart rate, oxygen saturation, blood pressure, and the like, but is not limited thereto.

In addition, the biometric index obtaining device 10 may calculate biometric information based on the measured parameter. More specifically, the biometric index obtaining device 10 may calculate biometric information based on the measured biometric index, and may calculate biometric information by comprehensively considering personal and statistical data such as facial expression, posture, age, and the like.

For example, the biometric index obtaining device 10 may calculate emotional information, sleepiness information, and the like of the subject based on the measured biometric index such as heart rate, oxygen saturation, blood pressure, and the like, but is not limited thereto.

In addition, the biometric index obtaining device 10 may store the measured parameter and the calculated biometric information. For example, the biometric index obtaining device 10 may store the measured parameter and the calculated biometric information of the subject in an internal memory, but is not limited thereto.

In addition, the biometric index obtaining device 10 may display the measured parameter and the calculated biometric information. For example, the biometric index obtaining device 10 may further include a display, and may display the measured biometric index and the calculated biometric information of the subject using the display, but is not limited thereto, and may transmit corresponding information to be displayed on an external display.

In addition, the biometric index may be displayed once through the display, and a biometric index that changes in real time may be continuously displayed.

The biometric index obtaining device 10 may transmit the biometric index and the biometric information of the subject to the server 20.

In this case, the biometric index and the biometric information transmitted to the server 20 may be stored in the server 20 as personal data. For example, the biometric index measured from the subject A and the calculated biometric information may be stored in the server 20 as data for the subject A, and the biometric index measured from the subject B and the calculated biometric information may be stored in the server 20 as data for the subject B.

The server 20 may communicate with an external terminal to transmit the biometric index and the biometric information of the subject when necessary. For example, when a person called subject A in which the biometric index and the biometric information data are stored in the server 20 visits a hospital to receive a treatment, a doctor for treating the subject A may need the parameter and the biometric information of the subject A. In this case, when the server 20 receives a request for transmitting the biometric index and the biometric information data of the subject A from an external terminal disposed in the hospital, the server 20 may communicate with the external terminal to transmit the biometric index and the biometric information data of the subject A.

As described above, it is apparent that the biometric index and the biometric information management system 100 may be a foundation for providing a continuous and comprehensive management service for personal health, and the biometric index and the biometric information management system 100 may be a foundation for providing various comprehensive management services using the parameter and the biometric information that are continuously measured and stored and managed as well as the above-described examples.

In addition, referring to FIG. 2, the biometric index and the biometric information management system 100 according to an embodiment may include an image obtaining device 30 and a server 20.

In this time, the image obtaining device 30 may obtain an image or a video of the subject.

In addition, the server 20 may obtain a video or image of the subject from the image obtaining device 30.

In addition, the server 20 may obtain personal and statistical data of the subject from an input device, an external terminal, and the like.

In addition, the server 20 may measure the biometric index of the subject based on the obtained image or the image. For example, the server 20 may measure the biometric index such as a heart rate, oxygen saturation, blood pressure, and the like of the subject by analyzing the obtained image or the image, but is not limited thereto.

In addition, the server 20 may calculate the biometric information based on the measured biometric index. More specifically, the server 20 may calculate biometric information based on the measured biometric index, and may calculate biometric information by comprehensively considering the measured biometric index and personal and statistical data such as facial expression, posture, and age.

For example, the server 20 may calculate the biometric information such as emotion information, drowsiness information, and the like of the subject based on the measured biometric index such as a heart rate, oxygen saturation, blood pressure, and the like, but is not limited thereto.

Also, the server 20 may store the measured biometric index and the calculated biometric information.

Further, since it is clear that the biometric index and biometric information management system 100 including the image obtaining device 30 and the server 20 may perform the functions of the biometric index and biometric information management system described above with reference to FIG. 1, redundant descriptions will be omitted.

2. Various Embodiments of a Biometric Index Obtaining Device

FIG. 3 is a diagram for describing a biometric index obtaining device according to an embodiment.

Referring FIG. 3, the biometric index obtaining device 1000 may include at least some of the image obtaining unit 1010, the controller 1020, the storage 1030, and the communication unit 1040. For example, the biometric index obtaining device 1000 may include only the image obtaining unit 1010 and the controller 1020, but is not limited thereto and may be implemented in various ways.

In addition, the image obtaining unit 1010 may obtain an image or a video of the subject. More specifically, the image obtaining unit 1010 may include a photographing device, and may obtain an image or an image of the subject by using the photographing device, or may obtain an image or an image of the subject from a photographing device disposed outside the biometric index obtaining device 1000, but is not limited thereto.

In addition, when the image obtaining unit 1010 obtains an image or an image of a subject from the photographing device, the photographing device may be provided as a visible camera for obtaining a visible light image, an infrared camera for obtaining an infrared image, or the like, but is not limited thereto, and a hybrid type camera for obtaining a visible light image and an infrared image may be provided.

In addition, when the photographing device obtains a visible light image, the obtained visible light image may be obtained as at least one color channel value. For example, the obtained visible light image may be obtained as a color channel value of an RGB color space expressed by red, green, and blue, and may be obtained as a color channel value of an HSV color space represented by hue, saturation, and brightness.

In addition, when the photographing device obtains an infrared image, the photographing device may obtain an infrared image through infrared illumination disposed inside or outside the photographing device. In this case, the infrared illumination may illuminate infrared light in a near infrared region having a wavelength band of 750 nm to 3000 nm, but is not limited thereto, and may also illuminate infrared light in a middle infrared region, a far infrared region, and an extreme infrared region.

In addition, the controller 1020 may obtain a biometric index by using an image of a subject obtained from the image obtaining unit 1010.

For example, the controller 1020 may obtain a biometric index such as heart rate, oxygen saturation, blood pressure, and body temperature of the subject by analyzing an image of the subject obtained from the image obtaining unit 1010, but is not limited thereto, and may obtain various biometric indexes.

In addition, the controller 1020 may calculate biometric information based on the obtained biometric index.

For example, the controller 1020 may calculate biometric information such as emotion information and drowsiness information of the subject based on the obtained biometric index such as heart rate, oxygen saturation, blood pressure, and body temperature, but is not limited thereto and may calculate various biometric information.

In addition, the controller 1020 may control operations of at least some of the image obtaining unit 1010, the storage unit 1030, and the communication unit 1040.

In addition, the storage unit 1030 may store the biometric index and the biometric information obtained by the controller 1020. More specifically, the storage unit 1030 may store the biometric index and the biometric information of one subject, or may store the biometric index and the biometric information of several subjects, respectively.

In addition, the communication unit 1040 may transmit the biometric index and the biometric information obtained by the controller 1020. More specifically, the communication unit 1040 may transmit the biometric index and the biometric information obtained by the controller 1020 toward a management server or toward a terminal of a user.

3. Various Embodiments of the Biometric Index and the Biometric Information Obtaining Method

3.1 Method for Obtaining Biometric Index

FIG. 4 is a flowchart illustrating a method of obtaining a bioindex according to an embodiment.

Referring to FIG. 4, the biometric index obtaining method 1100 according to an embodiment may include obtaining an image of a subject with respect to the subject (S1110).

In this case, in order to obtain an image of the subject, the image may be obtained using various cameras such as a visible light camera and an infrared camera, or the image may be obtained from various cameras, and thus a detailed description thereof will be omitted.

In addition, the biometric index obtaining method 1100 according to an embodiment may include detecting a skin region (S1120).

In this case, the skin region may mean a region that may be estimated as the skin region of the subject among the images of the subject.

In addition, the skin region may have a well-reflective change in blood vessels due to heartbeat, and detecting the skin region as described above may improve accuracy of biometric index obtaining.

In addition, in order to detect the skin region, a region other than the skin region of the subject, such as the eye, hair, etc., may be removed, except for the skin region that may reflect a change in color due to a blood vessel expansion. For example, the color value of the skin region other than the eye, hair, etc., of the subject may be substituted with a value that is not meaningful, such as black, but is not limited thereto.

In addition, according to an embodiment, a specific color space may be used to detect the skin region. For example, in the step of detecting the skin region (S1120), the image of the obtained subject may be substituted with a value of a YCrCb color space, and the skin region may be detected based on the image represented by the YCrCb color space, but is not limited thereto.

In addition, it is apparent that the skin region may be detected using various techniques known in the art to detect the skin region.

In addition, the biometric index obtaining method 1110 according to an embodiment may include setting a region of interest (S1130).

In this case, the ROI may mean an area of interest for data processing among the obtained images of the subject, and may mean an area that can be used for data processing to obtain the biometric index, but is not limited thereto.

In addition, according to an embodiment, a face area of the subject may be set to set the ROI. For example, the face area of the subject may be set to set the ROI included in the face of the subject.

More specifically, an area having a predetermined ratio based on the center of the face area of the subject may be set as the ROI.

For example, the face area may be vertically cropped by 80%, and horizontally cropped by 60%, based on the center of the face area of the subject, but is not limited thereto.

In addition, according to an embodiment, a feature point may be used to set the ROI. For example, a nose area of the subject may be extracted as a feature point from the obtained image of the subject, and the ROI may be set based on the extracted feature point, but is not limited thereto.

More specifically, an area having a predetermined size based on the extracted feature point for the set face area may be set as the ROI, but is not limited thereto.

In addition, according to an embodiment, a plurality of specific points may be used to set the ROI. For example, eyes and nose areas of the subject may be extracted as a feature point from the obtained image of the subject, and the ROI may be set based on the extracted feature points.

In addition, when the ROI is set for each of the plurality of images that are successively obtained, the ROI may be independently set for each of the plurality of images, and may be set to be related.

For example, in order to set the ROI for each of the plurality of images to be related, the face area of the subject may be set for each of the plurality of images, and when a difference between the center of the face area set in the first image frame and the center of the face area set in the second image frame that is obtained after the first image frame does not exceed a threshold, the face area of the second image frame may be set to be the same as the face area set in the first image frame, but is not limited thereto.

In addition, when a difference between the center of the face area set in the first image frame and the center of the face area set in the second image frame exceeds the threshold, the face area of the second image frame may be set to be different from the face area set in the first image frame, but is not limited thereto.

In addition, the ROI according to an embodiment may include a part of a body part or a part of a face according to the biometric index to be obtained, and at least one ROI may be set.

For example, the ROI may be set to include at least a part of a ball area to obtain a heart rate among the biometric index. More specifically, the ROI may be set to include a cheek area that can easily obtain a heart rate because the degree of expansion of blood vessels can be well reflected according to blood flow, but is not limited thereto.

In addition, for example, the region of interest may be set to at least two or more in order to obtain blood pressure among biometric indices, and more particularly, the region of interest may be set to a region of interest including an upper region of a face and a lower region of a face in order to reflect blood flow, but is not limited thereto.

In addition, for example, the region of interest may be set to at least two or more in order to obtain blood pressure among biometric indices, and more particularly, the region of interest may be set to two or more region of interest that are different from each other from a heart. For example, the region of interest may be set to a region of interest including a hand region and a region of interest including a face region, but is not limited thereto.

In addition, the biometric parameter obtaining method 1110 according to an embodiment may include processing data for the region of interest (S1140), in operation S1140.

In addition, a color channel value for the region of interest may be extracted in order to process the data for the region of interest. In this case, the color channel value may be an average value of color channel pixel values of pixels included in the region of interest, and may be referred to as an average pixel value.

For example, when a color channel value according to an RGB color space is extracted, a Red channel pixel value, a Green channel pixel value, and a Blue channel pixel value of respective pixels included in the region of interest may be extracted, and a Red channel value that is an average value of Red channel pixel values included in the region of interest, a Blue channel value that is an average value of Blue channel pixel values, and a Green channel value that is an average value of Green channel pixel values may be extracted, but is not limited thereto, and a color channel value according to various color spaces such as HSV and YCrCb color spaces may be extracted.

In addition, the color channel value extracted according to a specific color space may be converted into other color spaces. For example, the color channel value extracted according to an RGB color space may be converted into a color channel value according to various color spaces such as HSV and YCrCb color spaces.

In addition, the color channel value extracted in order to process the data for the region of interest may be a color channel value combined by applying a weight to at least a portion of the color channel value extracted according to various color spaces.

In addition, the color channel value may be extracted for each of a plurality of image frames that are successively obtained, and may be extracted for at least a portion of the image frames.

In addition, the color channel values extracted from one image frame may be processed through an operation or the like. More particularly, the plurality of channel values obtained from one image frame may be processed through an operation such as adding or subtracting the plurality of channel values from each other, and for example, the Green channel value and the Red channel value obtained from one image frame may be processed through a differential operation, but are not limited thereto, and various channel values may be processed through various operations.

In addition, the color channel values or the processing values extracted from each of the plurality of image frames may be processed through an operation or the like. More specifically, the color channel values or the processing values of the color channel values extracted from each of the plurality of image frames may be processed through an operation such as obtaining a predetermined interval average or obtaining a deviation, but is not limited thereto, and may obtain a difference between maximum value minimum values during a predetermined interval, or may be processed through various operations.

In addition, the color channel values and the processing values of the color channel values extracted from each of the plurality of image frames may be processed to obtain at least one time series data.

In addition, a feature value for obtaining the biometric index may be extracted based on at least some of the color channel values, the processing values, and the time series data. For example, a frequency component for obtaining a heart rate may be extracted based on a frequency component of the time series data, but is not limited thereto.

In addition, the biometric index obtaining method 1110 according to an embodiment may include obtaining the biometric index (S1150).

In addition, the feature value extracted from the ROI may be used to obtain the biometric index. For example, the heart rate may be obtained based on a frequency component of the time series data extracted from the ROI, but is not limited thereto.

In addition, since the step S1140 of processing data for the ROI and the step S1150 of obtaining the biometric index may be different according to each biometric index, more details will be described in detail in the corresponding sections.

FIG. 5 is a diagram illustrating a method of obtaining a biometric index according to an embodiment.

Referring to FIG. 5, an image 1161 of a subject may include a face region, may detect a skin region 1162, and may detect the ROI 1163. Details thereof will be omitted from the descriptions redundantly given above.

In addition, referring to FIG. 5, a color channel value for the ROI may be extracted 1164, the extracted color channel value may be processed 1165, and a biometric index may be obtained based on the extracted color channel value 1166.

However, this will be described in detail in the corresponding sections below.

3.2 Biometric Information Obtaining Method

FIG. 6 is a flowchart illustrating a method of obtaining biometric information according to an embodiment.

Referring to FIG. 6, a method of obtaining biometric information according to an embodiment may include obtaining a biometric index (S1210).

In this case, the biometric index may be obtained by the above-described method of obtaining the parameter, but is not limited thereto, and may be obtained by an external sensor such as an ECG sensor.

In addition, redundant descriptions of the biometric index will be omitted.

In addition, the method of obtaining biometric information according to an embodiment may include obtaining personal and statistical data (S1220).

In this case, the personal and statistical data may mean personal and statistical data that may be collected by the subject such as age, gender, and may mean personal and statistical data that may be observed by the subject such as facial expression, wrinkles, etc., but is not limited thereto, and may be various personal and statistical data except for the biometric index for obtaining biometric information.

In addition, the method of obtaining biometric information according to an embodiment may include obtaining biometric information (S1230).

In this case, the biometric information may be drowsiness information, emotional information, etc of the subject, but is not limited thereto.

In addition, the biometric index may be used to obtain the biometric information. For example, a heart rate among the biometric indices may be used to obtain the drowsiness information. More specifically, when the heart rate of the subject becomes a reference heart rate or less, the subject may be considered to be in a drowsiness state, and a degree of drowsiness of the subject may be obtained according to a time being less than or equal to the reference heart rate.

In addition, for example, to obtain the emotional information, a heart rate and a blood pressure among the biometric indices may be used. More specifically, when the heart rate and the blood pressure of the subject becomes a reference heart rate and a blood pressure or more, the subject may be considered to be in an excited state.

In addition, the biometric index and the personal and statistical data may be used to obtain the biometric information. For example, personal and statistical data such as the heart rate and the age, gender, etc of the subject may be used to obtain the drowsiness information.

In addition, for example, personal and statistical data such as the heart rate, the blood pressure and the expression of the subject, the age, gender, etc may be used to obtain the emotional information.

In addition, a weight may be given to the biometric index and the personal and statistical data to obtain the biometric information. For example, different weights may be given to the biometric index and the personal and statistical data to obtain the biometric information, and different weights may be given according to the subject.

Figure 8:
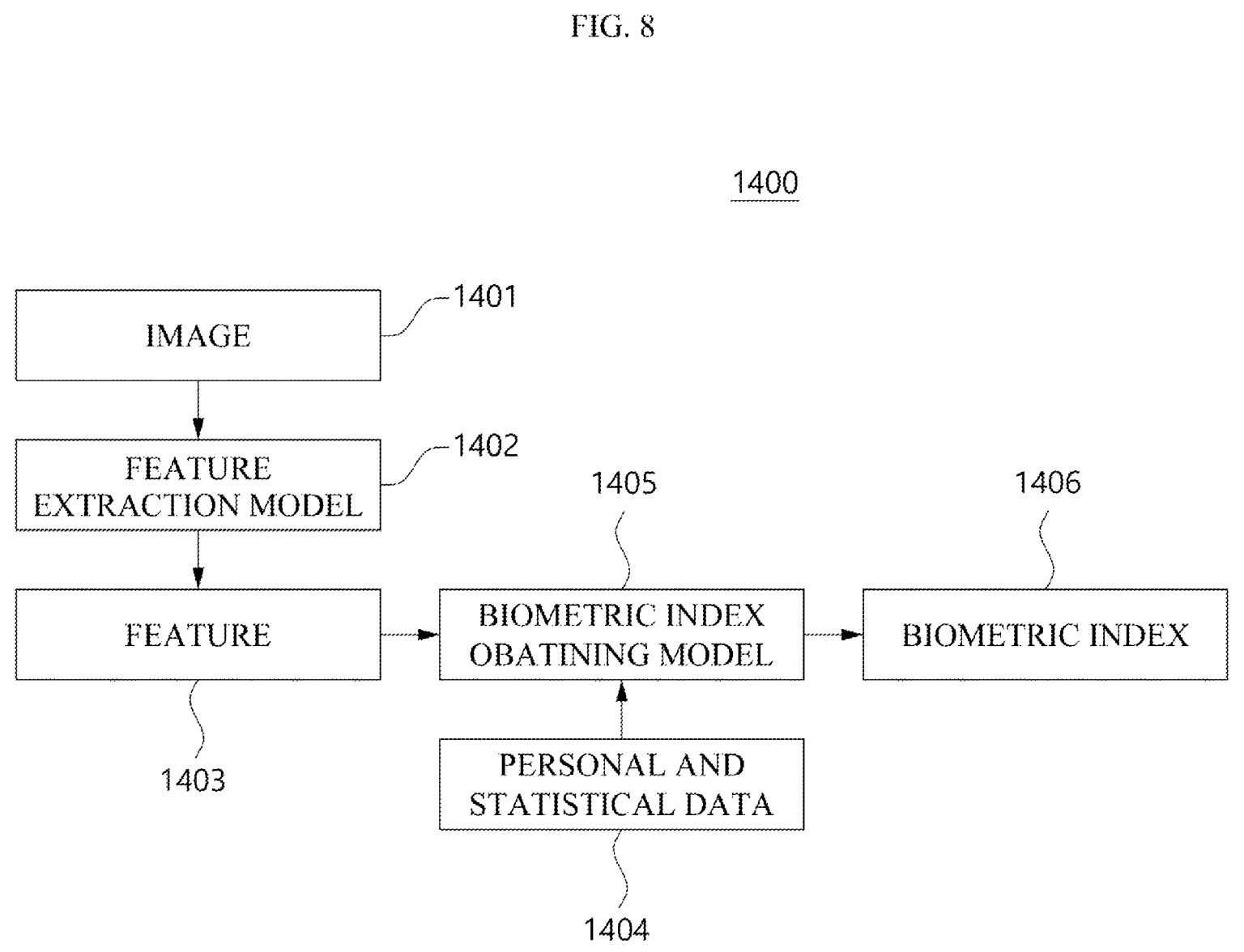

3.3 A Biometric Index Obtaining Method Using a Biometric Index Obtaining Model FIGS. 7 and 8 are diagrams for describing a method of obtaining a biometric index using a biometric index obtaining model.

14

701 of FIG. 7 illustrates a biometric index obtaining method 1300 using a biometric index obtaining model 1302 according to an embodiment.

In this case, the biometric index obtaining model 1302 according to an embodiment may be implemented by a machine learning method. For example, the biometric index obtaining model 1302 may be a model implemented through supervised learning, but is not limited thereto, and may be a model implemented through non-supervised learning, semi-supervised learning, reinforcement learning, etc.

In addition, the biometric index obtaining model 1302 according to an embodiment may be implemented as an artificial neural network (ANN). For example, the biometric index obtaining model 1302 may be implemented as a Feedforward neural network, a radial basis function network, a cohonen self-organizing network, etc., but is not limited thereto.

In addition, the biometric index obtaining model 1302 according to an embodiment may be implemented as a deep neural network (DNN). For example, the biometric index obtaining model 1302 may be implemented as a convolutional neural network (CNN), a recurrent neural network (RNN), a long short term memory network (LSTM), a gated recurrent units (GRUs), etc., but is not limited thereto.

In addition, the image 1301 input to the biometric index obtaining model 1302 may be obtained image data itself.

In addition, the image 1302 input to the biometric index obtaining model 1302 may be preprocessed image data. For example, the image 1302 may be eulerian video Magnification, but is not limited thereto, and may be various preprocessing such as obtaining an average value of the obtained RGB value. As another example, the image 1302 may include time series data or target time series data to be described later.

In addition, the obtained biometric index 1303 may be a heart rate, oxygen saturation, blood pressure, body temperature, etc.

In addition, the obtained biometric index 1303 may be one and a plurality of biometric indices may be simultaneously obtained. For example, a heart rate may be obtained as a result of the biometric index obtaining model 1302, but is not limited thereto, and a heart rate and blood pressure may be simultaneously obtained as a result of the biometric index obtaining model 1302.

(b) of FIG. 7 illustrates a biometric index obtaining method 1350 using a biometric index obtaining model 1354 according to another embodiment.

In this case, the biometric index obtaining model 1354 may obtain a feature 1352 and personal and statistical data 1353 extracted from the image 1351 as an input value. For example, a feature called time series data for a color channel value may be extracted from the image 1351, and the biometric index obtaining model 1354 may obtain time series data and personal and statistical data for the color channel value as an input value and calculate the result of the biometric index 1355.

In addition, in the present specification, the feature may be represented by biosignal feature data.

In addition, the personal and statistical data may mean personal and statistical data that can be collected by a subject such as age, gender, height, weight, etc., may mean personal and statistical data that can be observed such as facial expression, wrinkles, face color, etc., etc., etc., by a subject, and may mean personal and statistical data that can be numericalized such as average blood pressure, average color, average height, average weight, etc.

In addition, the biometric index obtaining model 1354 may apply the contents of the biometric index obtaining model 1302 described above, and thus redundant descriptions will be omitted.

In addition, FIG. 8 illustrates a biometric index obtaining method 1400 using a biometric index obtaining model 1405 according to another embodiment.

In this case, the biometric index obtaining method 1400 may include a feature extraction model 1402, and the feature extraction model 1402 according to an embodiment may be implemented by a machine learning method. For example, the feature extraction model 1402 may be a model implemented through map learning, but is not limited thereto, and may be a model implemented through non-map learning, semi-map learning, reinforcement learning, etc.

In addition, the feature extraction model 1402 according to an embodiment may be implemented as an artificial neural network (ANN). For example, the biometric index obtaining model 1302 may be implemented as a Feedforward neural network, a radial basis function network, a cohonen self-organizing network, etc., but is not limited thereto.

In addition, the feature extraction model 1402 according to an embodiment may be implemented as a deep neural network (DNN). For example, the biometric index obtaining model 1302 may be implemented as a convolutional neural network (CNN), a recurrent neural network (RNN), a long short term memory network (LSTM), a gated recurrent unit (GRU), or the like, but is not limited thereto.

In addition, the biometric index obtaining model 1405 may obtain the feature 1403 and the personal and statistical data 1404 extracted from the feature extraction model 1402 as an input value, and may calculate the biometric index 1406 as a result based on the input value.

In addition, the contents of the biometric index obtaining model 1302 described above may be applied to the biometric index obtaining model 1405, and thus redundant descriptions will be omitted.

As described above with reference to FIGS. 7 and 8, a machine learning, an artificial neural network, or a deep neural network model may be used to obtain a biometric index.

A method of obtaining a biometric index using the biometric index obtaining model will be described in more detail with reference to FIGS. 25 to 29 to be described later.

4. Various Embodiments of Biometric Obtaining

4.1 Various Embodiments of a Method of Measuring Heart Rate

When the heart is beating in the body of a living organism, the blood may be transported to the whole body by the beating of the heart. In this case, the blood flows along the blood vessel, the volume of the blood vessel may change with time, and the amount of blood included in the blood vessel may change.

Therefore, when measuring the change in the volume of the blood vessel or the change in the amount of the blood, the heart rate may be obtained. For example, when the amount of blood included in the blood vessel changes, the amount of hemoglobin and oxyhemoglobin included in the blood may change, and accordingly, the amount of light reflected by the blood may change. Therefore, when measuring the change in the amount of light reflected by the blood as described above, the heart rate may be obtained.

In addition, it is apparent that various principles for measuring the heart rate with light may be applied in addition to the above-described exemplary principles.

Figure 9:
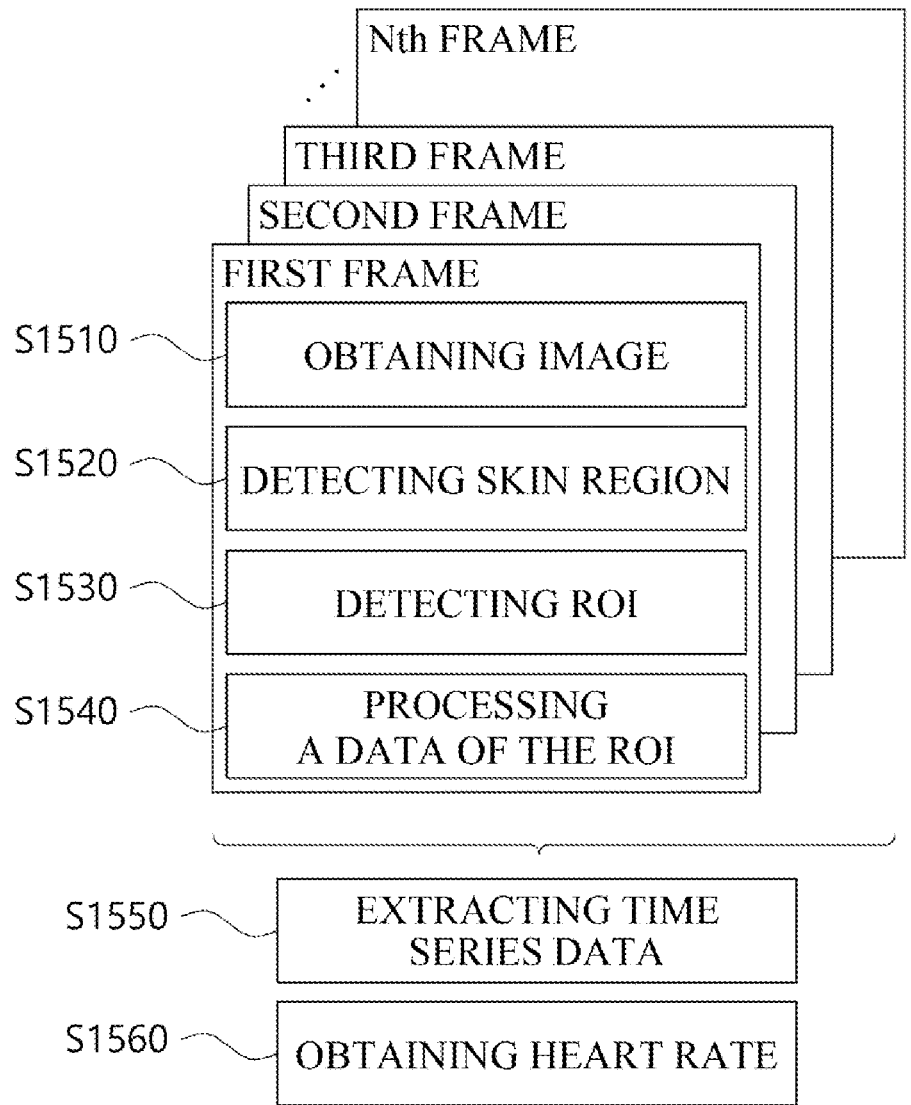
FIG. 9 is a flowchart illustrating a heart rate measurement method according to an embodiment.

FIG. 9 is a flowchart for describing a method of measuring heart rate according to an embodiment.

Referring to FIG. 9, the heart rate measurement method 1500 according to an embodiment may include at least some of the following steps: obtaining an image in step S1510, detecting a skin region in step S1520, detecting a region of interest in step S1530, and processing data of the region of interest, with respect to at least one image frame among the obtained plurality of image frames, but is not limited thereto.

In addition, the obtaining the image in step S1510, the detecting the skin region in step S1520, and the detecting the region of interest in step S1530 will not be described above.

In addition, the processing the data of the region of interest in step S1540 may be performed on at least one image frame among the obtained plurality of image frames.

In addition, a color channel value of the region of interest may be extracted with respect to at least one image frame among the obtained plurality of image frames for processing the data of the region of interest. In this case, the color channel value may be an average value of the color channel values of pixels included in the region of interest, and may be referred to as an average pixel value.

In addition, details of the step S1540 of processing the data for the region of interest will be omitted from the above-described descriptions.

In addition, the method 1500 for measuring the heart rate according to an embodiment may include at least some of the step S1550 of extracting time series data for at least some image frame groups among the obtained plurality of image frames and the step S1560 of obtaining the heart rate, but is not limited thereto.

In addition, the step S1550 of extracting the time series data may be performed on at least some image frame groups among the obtained plurality of image frames.

In this case, the image frame group may mean a plurality of image frame groups that are consecutive or discontinuous. For example, the image frame group may mean a group of image frames that are consecutive from a first image frame to a first 80 image frame, but is not limited thereto, and may mean a group of image frames that are at least some from the first image frame to the first 80 image frame.

In addition, the step S1560 of obtaining the heart rate may be performed on at least some image frame groups among the obtained plurality of image frames.

In this case, a frequency component of the obtained time series data may be extracted to obtain the heart rate. For example, the time series data may be transformed according to a fourier transform (FT) to obtain the heart rate to extract a frequency component, but is not limited thereto, and the time series data may be transformed according to a Fast Fourier transform (FFT), a discrete Fourier transform (DFT), a short time fourier transform (STFT), or the like, but is not limited thereto and may be various processing for extracting the frequency component.

In addition, the heart rate may be obtained based on one heart rate and may be obtained based on at least two heart rates. For example, one heart rate may be obtained based on one time series data, another heart rate may be obtained based on another time series data, and a final heart rate may be obtained based on the obtained at least two heart rates, but is not limited thereto.

4.2 Blood Pressure Measurement Method

The blood pressure may mean a pressure at which blood flowing along a blood vessel gives a pressure to a wall of the blood vessel.

Therefore, the blood pressure may be affected by a velocity of blood flow, a thickness of a wall of the blood vessel, a waste of blood accumulated in the blood vessel, or the like.

In addition, when blood flows along a blood vessel, the volume of the blood vessel may change with time, and the amount of blood included in the blood vessel may change.

Therefore, when measuring the velocity of change of the volume of the blood vessel and the velocity of change of the amount of blood, the blood pressure may be obtained.

For example, when measuring the change of the blood vessel at two points having different distances from the heart, the blood pressure may be obtained based on a difference in the change of the blood vessel at the two points, and the blood pressure may be obtained by extracting a feature that may indicate the change of the blood vessel that changes with time, but is not limited thereto.

In addition, it is apparent that various principles for measuring the blood pressure by light may be applied in addition to the above-described exemplary principles.

Figure 10:
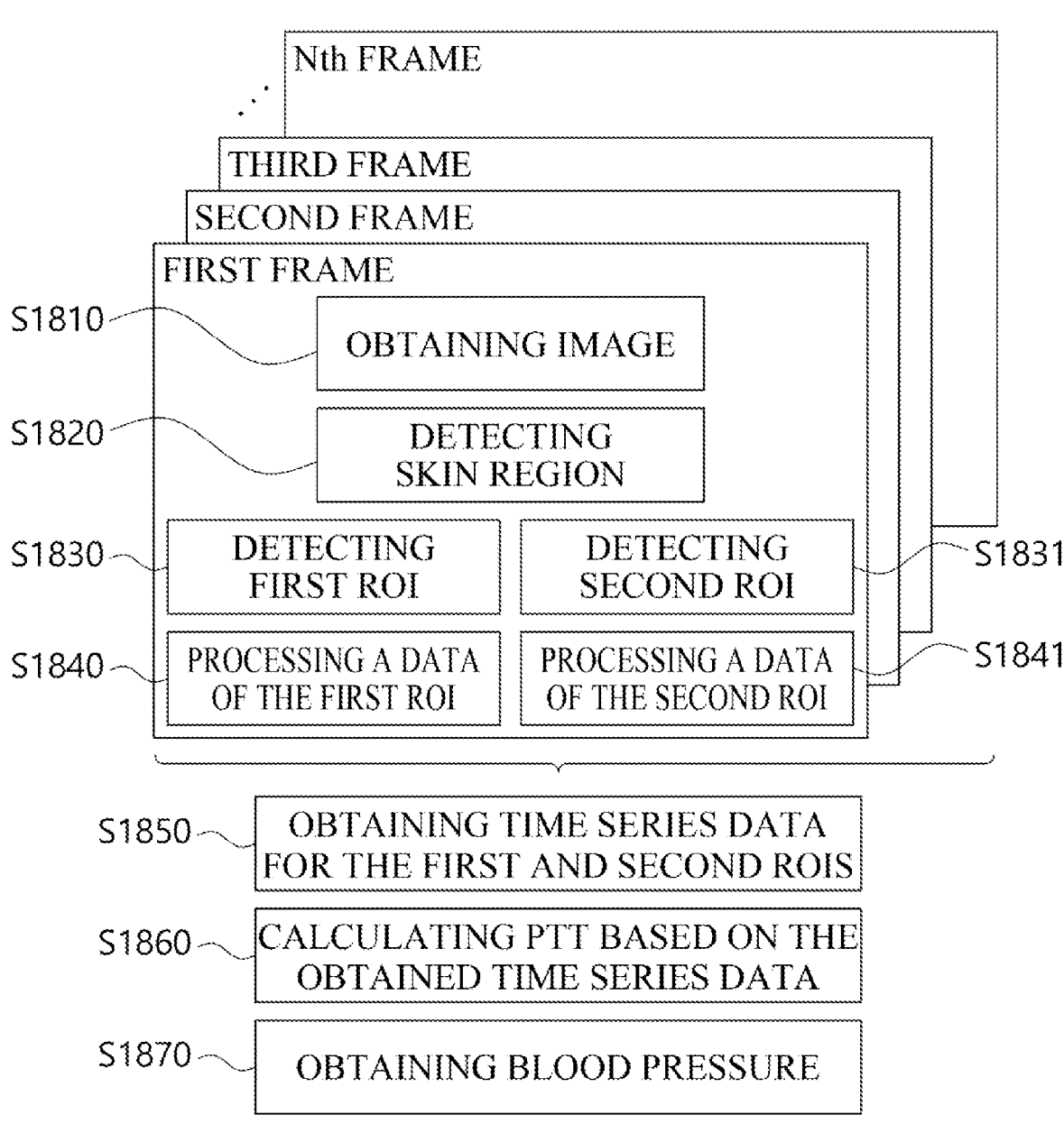
FIG. 10 is a flowchart illustrating a blood pressure measurement method according to an embodiment.

FIG. 10 is a flowchart illustrating a blood pressure measurement method according to an embodiment.

Referring to FIG. 10, the blood pressure measurement method 1800 according to an embodiment may include at least some of the following steps: obtaining an image in step S1810; detecting a skin region in step S1820; detecting a first ROI in step S1830; detecting a second ROI in step S1831; processing data for the first ROI in step S1840; and processing data for the second ROI in step S1841; with respect to at least one of the obtained plurality of image frames, but is not limited thereto.

In addition, the obtaining the image in step S1810 and the detecting the skin region in step S1820 may not be repeatedly described above.

In addition, details of the detecting the first ROI and second ROI in steps S1830 and S1831 may not be repeatedly described above.

In this case, the first ROI and the second ROI may be set to two regions having different distances from the heart of the subject. For example, the first ROI may be set to an upper region of the face of the subject and the second ROI may be set to a lower region of the face of the subject, but is not limited thereto, and the first ROI may be set to the face of the subject and the second ROI may be set to a back of the subject.

In addition, the processing the data for the first ROI in step S1840 and the processing the data for the second ROI in step S1841 may perform operations of the above-described processing of the data for the ROI, and thus a repeated description thereof will be omitted.

In addition, the blood pressure measurement method 1800 according to an embodiment may include at least some of the following steps: extracting time series data for the first and second ROIs in the image frame group of at least some of the obtained plurality of image frames in step S1850; calculating a pulse transit time (PTT) based on the obtained time series data in step S1860; and obtaining blood pressure in step S1870, but is not limited thereto.

In addition, the extracting the time series data for the first and second ROIs in step S1850 may perform operations of the above-described extracting of the time series data, and thus a repeated description thereof will be omitted.

In addition, the calculating the PTT based on the obtained time series data in step S1860 may be performed with respect to at least some of the obtained plurality of image frames.

In this case, the PTT may be calculated based on the time series data for the first ROI and the extrema of the time series data for the second ROI. For example, the PTT may be calculated based on a time difference between the extrema of the time series data for the first ROI and the extrema of the time series data for the second ROI, but is not limited thereto, and the PTT may be calculated based on a time difference between the extrema of the time series data for the first ROI and the extrema of the time series data for the second ROI.

In addition, the PTT may be calculated based on the time series data for the first region of interest and the inflection point of the time series data for the second region of interest. For example, the PTT may be calculated based on the time difference between the inflection point of the time series data for the first region of interest and the inflection point of the time series data for the second region of interest, but is not limited thereto.

In addition, the PTT may be calculated based on various points of the time series data for each region of interest in addition to the above-described extrema and inflection points.

In addition, the time difference between the time series data for the first region of interest and the time series data for the second region of interest may be calculated based on a frame obtained at a point such as the extrema and inflection points. For example, when a maximum value is obtained in a tenth frame in the time series data for the first region of interest and a maximum value is obtained in a twelfth frame in the time series data for the second region of interest, the time difference between the time series data for the first region of interest and the time series data for the second region of interest may be a time for obtaining two frames, and the PTT may be calculated based on the time difference.

In addition, the step of obtaining the blood pressure (S1870) may be performed on at least a part of the obtained image frames of the plurality of image frames.

In addition, the PTT may be used to obtain the blood pressure. For example, a function for the PTT may be used to obtain the blood pressure. More specifically, a function such as Equation 1 may be used, and various functions such as a first function using the PTT as a variable, a second function, a logarithmic function, an exponential function, and the like may be used as the function, but is not limited thereto.

$$BP = f(PTT) \qquad \text{Equation 1}$$

In addition, the PTT and the personal and statistical data may be used to obtain the blood pressure. For example, a function for the PTT and a function of the personal and statistical data such as age, weight, and height may be used to obtain the blood pressure. More specifically, Equation 2 may be used, and various functions such as a first function using the PTT as a variable, a second function using the PTT as a variable, a logarithmic function, an exponential function, and the like may be used as the function, but is not limited thereto.

$$BP = a \cdot f_1(\text{weight}) + b \cdot f_2(\text{height}) + c \cdot f_3(\text{age}) + d \cdot f_4(\text{PTT}) \qquad \text{Equation 2}$$

In addition, the method of analyzing the regression using the above-described function may be used to obtain the blood pressure, but is not limited thereto.

In addition, the method of using the above-described function may be used to obtain the blood pressure, but is not limited thereto.

In addition, it is apparent that various equations for calculating the blood pressure using the PTT may be used in addition to the above-described exemplary equations.

In addition, the blood pressure may be obtained based on one blood pressure and may be obtained based on at least two blood pressures. For example, one blood pressure may be obtained based on a first PTT calculated based on time series data for the first and second regions of interest, another blood pressure may be obtained based on a second PTT calculated based on other time series data for the first and second regions of interest, and a final blood pressure may be obtained based on the obtained at least two blood pressures, but is not limited thereto.

Figure 11:
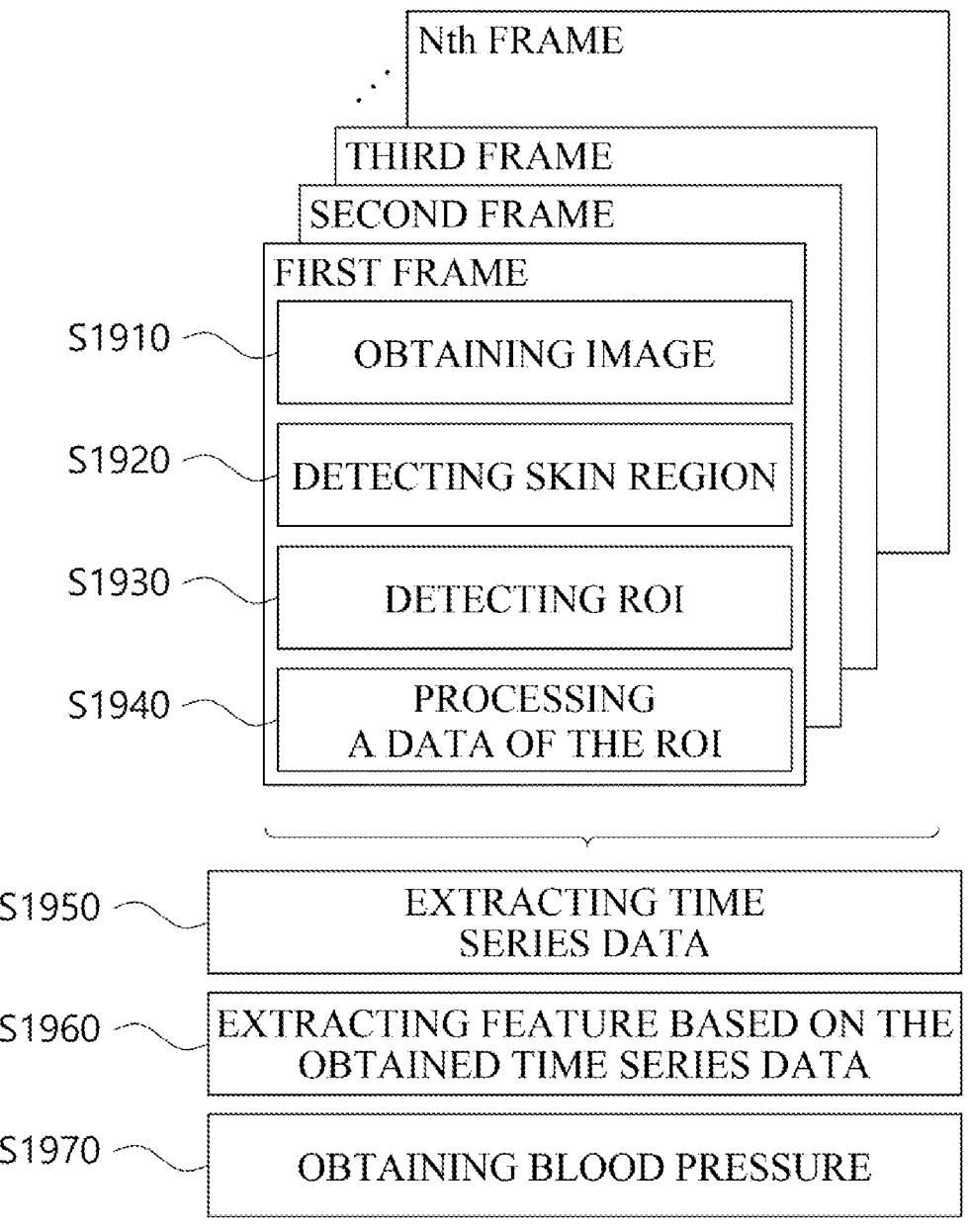
FIG. 11 is a flowchart illustrating a blood pressure measurement method according to another embodiment.

FIG. 11 is a flowchart illustrating a blood pressure measurement method according to another embodiment.

Referring to FIG. 11, the blood pressure measurement method 1900 according to an embodiment may include at least some of the following steps: obtaining an image in step S1910, detecting a skin region in step S1920, detecting a region of interest in step S1930, and processing data for the region of interest in at least one image frame among the obtained plurality of image frames, but is not limited thereto.

In this case, details of the obtaining the image in step S1910, the detecting the skin region in step S1920, the detecting the region of interest in step S1930, and the processing data for the region of interest in step S1940 are not redundant as described above.

In addition, the blood pressure measurement method 1900 according to an embodiment may include at least some of the following steps: extracting time series data for at least some image frame groups among the obtained plurality of image frames, extracting features based on the obtained time series data in step S1960, and obtaining blood pressure in step S1970, but is not limited thereto.

In addition, the operations of extracting the time series data in step S1950 may be performed by the above-described operations of extracting the time series data, and thus redundant descriptions are not redundant.

In addition, the step of extracting features based on the obtained time series data in step S1960 may be performed on at least some image frame groups among the obtained plurality of image frames. In the present specification, the features may be expressed as bio-signal feature data.

In this case, the features may mean mathematical and physical features of the obtained time series data. For example, the features may mean mathematical features such as a maximum value, an average of the maximum value, a minimum value, an average of the minimum value, a difference between the maximum value and the minimum value, an average, an inflection point, a first derivative data, a second derivative data, and a slope at a specific time point of the obtained time series data, and may mean physical features such as a change in blood volume, a change in blood speed, a change in blood vessel volume, and a change in blood vessel speed, but is not limited thereto.

In addition, it is apparent that the features may be various features for obtaining blood pressure in addition to the above-described exemplary features.

In addition, the step of obtaining the blood pressure in step S1970 may be performed on at least some image frame groups among the obtained plurality of image frames.

In addition, the features may be used to obtain the blood pressure.

For example, a function for the features may be used to obtain the blood pressure. More specifically, a function such as Equation 3 may be used, and various functions such as a primary function, a secondary function, a logarithmic function, an exponential function, etc., which uses a feature as a variable, may be used as the function, but are not limited thereto.

$$BP = f(\text{feature}) \qquad \text{Equation 3}$$

In addition, the feature and personal and statistical data may be used to obtain the blood pressure. For example, a function of the feature and a function of personal and statistical data such as age, weight, and height may be used to obtain the blood pressure. More specifically, Equation 4 may be used, and various functions such as a primary function, a secondary function, a logarithmic function, an exponential function, etc., which uses a feature, weight, height, and age as a variable, may be used as the function, but are not limited thereto.

$$BP = a \cdot f_1(\text{weight}) + b \cdot f_2(\text{height}) + c \cdot f_3(\text{age}) + d \cdot f_4(\text{feature}) \qquad \text{Equation 4}$$

In addition, a regression analysis method using the above-described function may be used to obtain the blood pressure, but is not limited thereto.

In addition, a machine learning method using the above-described function may be used to obtain the blood pressure, but is not limited thereto.

In addition, it is apparent that a formula for obtaining blood pressure using a feature may be used in addition to the above-described exemplary formula.

In addition, the blood pressure may be obtained based on one blood pressure and may be obtained based on at least two blood pressures. For example, one blood pressure may be obtained based on a first feature calculated based on time series data, another blood pressure may be obtained based on a second feature calculated based on another time series data, and a final blood pressure may be obtained based on the obtained at least two blood pressures, but is not limited thereto.

5. Various Embodiments of a Method for Measuring Heart Rate

FIG. 12 is a flowchart illustrating a method for obtaining a heart rate according to an embodiment.

Referring to FIG. 12, the heart rate obtaining method 2100 according to an embodiment may include at least some of the following steps: obtaining an image (S2110), detecting a skin area (S2120), detecting a region of interest (S2130), processing data for the region of interest (S2140), obtaining a characteristic value (S2150), and obtaining a heart rate (S2160), but is not limited thereto.

In this case, the step of obtaining the image (S2110), the step of detecting the skin area (S2120), and the step of detecting the region of interest (S2130) may not be repeatedly described above.

In addition, the step of processing the data for the region of interest (S2140) may be performed on at least one image frame among the obtained plurality of image frames.

In addition, the step of processing the data for the region of interest (S2140) may be performed to reduce motion artifacts, external light artifacts, and the like.

In addition, the step of obtaining the characteristic value (S2150) may be performed on at least some image frame groups among the obtained plurality of image frames.

In addition, the step of obtaining the characteristic value (S2150) may be performed to reduce motion artifacts, external light artifacts, and the like.

In addition, the step of obtaining the heart rate (S2160) may be performed on at least a part of the obtained image frame group.

In this case, the image frame group for obtaining the heart rate and the image frame group for obtaining the characteristic value may be the same as each other, and may be different from each other. For example, the image frame group for obtaining the characteristic value may include 18 image frames, and the image frame group for obtaining the heart rate may include 180 image frames, but is not limited thereto.

Hereinafter, the steps of processing data for the region of interest (S2140), the steps of obtaining the characteristic value (S2150), and the steps of obtaining the heart rate (S2160) will be described in more detail.

Figure 13:
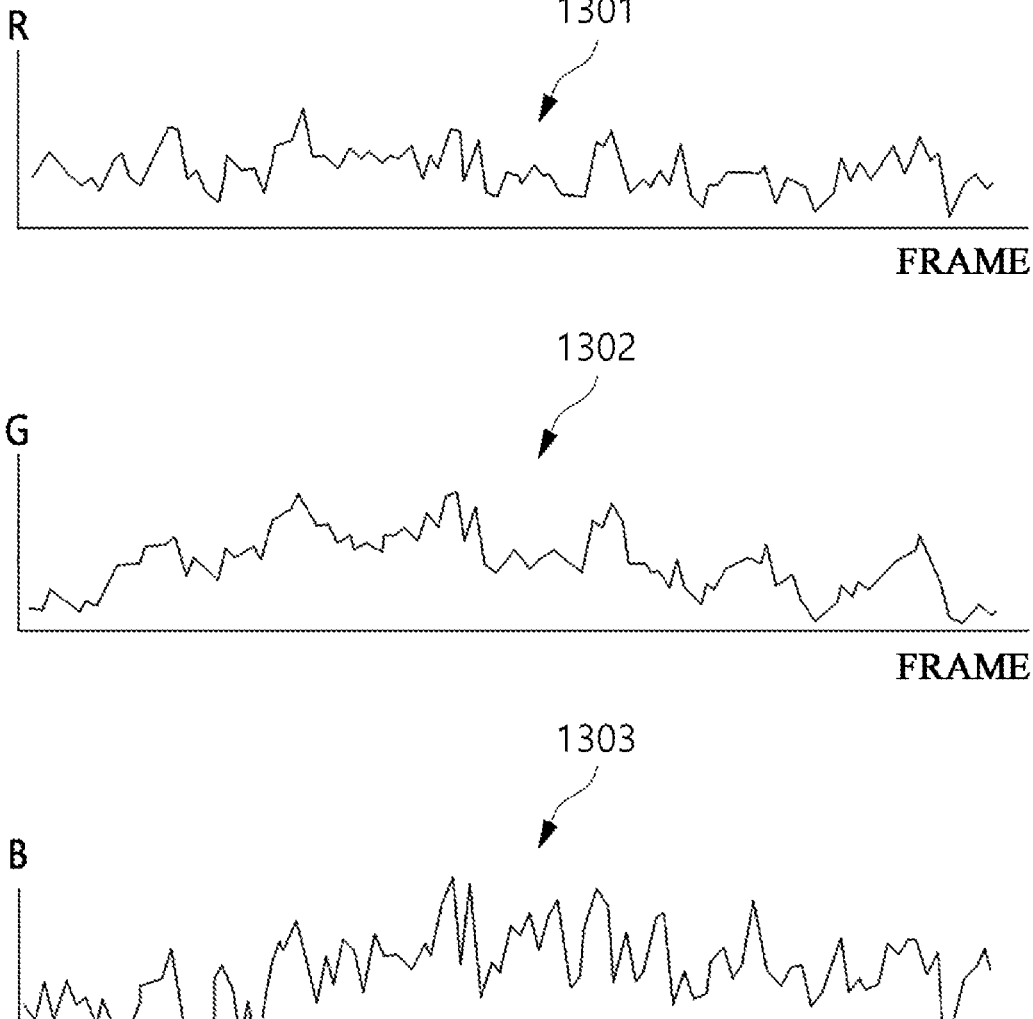
FIG. 13 is a graph of color channel values according to an embodiment.

FIG. 13 is a graph of color channel values according to an embodiment.

According to an embodiment, in order to process data for the region of interest, a color channel value for the region of interest may be extracted. In this case, the color channel value may be an average value of color channel values of pixels included in the region of interest, and may be referred to as an average pixel value.

Referring to FIG. 13, in order to process data for the region of interest, a color channel value according to an RGB color space for the region of interest may be extracted. More specifically, a Red channel value that is an average value of Red channel pixel values, a Blue channel value that is an average value of Blue channel pixel values, and a Green channel value that is an average value of Green channel pixel values may be extracted.

For example, when a color channel value according to an RGB color space is extracted, a Red channel pixel value, a Green channel pixel value, and a Blue channel pixel value of respective pixels included in the region of interest may be extracted, and a Red channel value that is an average value of Red channel pixel values, a Blue channel value that is an average value of Blue channel pixel values, and a Green channel value that is an average value of Green channel pixel values included in the region of interest may be extracted, but is not limited thereto, and a color channel value according to various color spaces such as HSV, YCrCb color space, and the like may be extracted.

In addition, the color channel value extracted according to a specific color space may be converted into another color space. For example, the color channel value extracted according to an RGB color space may be converted into a color channel value according to various color spaces such as HSV, YCrCb color space, and the like.

In addition, the color channel value extracted in order to process data for the region of interest may be a color channel value combined by applying a weight to at least a part of the color channel value extracted according to various color spaces.

In addition, the color channel value may be extracted for each of a plurality of image frames that are successively obtained, and may be extracted for at least a part of the image frames.

Hereinafter, descriptions are based on color channel values extracted according to an RGB color space, but it is apparent that various color channel values may be applied without being limited thereto.

1301 of FIG. 13 is a graph illustrating a Red channel value extracted according to an RGB color space, 1302 of FIG. 13 is a graph illustrating a Green channel value extracted according to an RGB color space, and 1303 of FIG. 13 is a graph illustrating a Blue channel value extracted according to an RGB color space.

As illustrated in FIG. 13, each color channel value may have a value variation according to a beat of a heart.

However, each color channel value may have a value variation according to a beat of a heart and also have a value variation according to a movement of a subject or a change in intensity of an external light.

Therefore, in order to obtain a heart rate using the extracted color channel value, an operation of reducing a value variation according to a movement of a subject or a change in intensity of an external light and maximizing a value variation according to a beat of a heart may be required.

5.1 Various Embodiments of a Method of Processing Data for a Region of Interest It is apparent that the above-described descriptions may be applied to a method of processing data for a region of interest, and descriptions overlapping with the above-described descriptions will be omitted.

FIG. 14 is a graph for describing a method of reducing noise according to an embodiment.

1401 of FIG. 14 is a graph illustrating a Red channel value extracted according to an RGB color space, and 1402 of FIG. 14 is a graph illustrating a Green channel value extracted according to an RGB color space.

Referring to 1401 and 1402 of FIG. 14, it can be seen that a variation of the extracted color channel value occurs over time.

In this case, the extracted color channel value may have a variation according to a beat of a heart, but may have a variation according to a movement of a subject or a change in intensity of an external light.

More specifically, a large and slow variation of a color channel value is a variation occurring because it is more influenced by a movement of a subject or a change in intensity of an external light, and a small and fast variation is a variation occurring because it is more influenced by a beat of a heart of a subject.

Therefore, since a larger variation of a value according to a movement of a subject or a change in intensity of an external light is a variation occurring than a variation according to a beat of a heart, a relative difference between at least two color channel values may be used to reduce the relative difference.

For example, a difference between a Green channel value and a Red channel value may be used to reduce noise. More specifically, a Green channel value and a Red channel value obtained in the same image frame may reflect the same movement and the same intensity of an external light, and a difference between a Green channel value and a Red channel value of the same frame may reduce noise according to a movement of a subject and a change in intensity of an external light, but the present invention is not limited thereto, and noise may be reduced by using a relative difference between at least two color channel values.

1403 of FIG. 14 is a graph illustrating a difference between the Green channel value and the Red channel value.

As illustrated in 1403 of FIG. 14, a difference between the Green channel value and the Red channel value may reduce noise according to a movement of a subject and a change in intensity of an external light, and the like.

In addition, the above-described method for reducing noise may be performed on at least one image frame among the obtained plurality of image frames, or may be performed on each of the consecutive plurality of image frames.

Although not shown in 1403 of FIG. 14, noise may be reduced by using a difference value between the Green channel value and the Blue channel value, or noise may be reduced by using a difference value between the Red channel value and the Blue channel value.

In addition, as described above, at least two color channel values may be selected to obtain a difference value in order to reduce noise by using a relative difference between the at least two color channel values.

In this case, the at least two color channel values may be selected in consideration of absorbance of blood.

Figure 15:
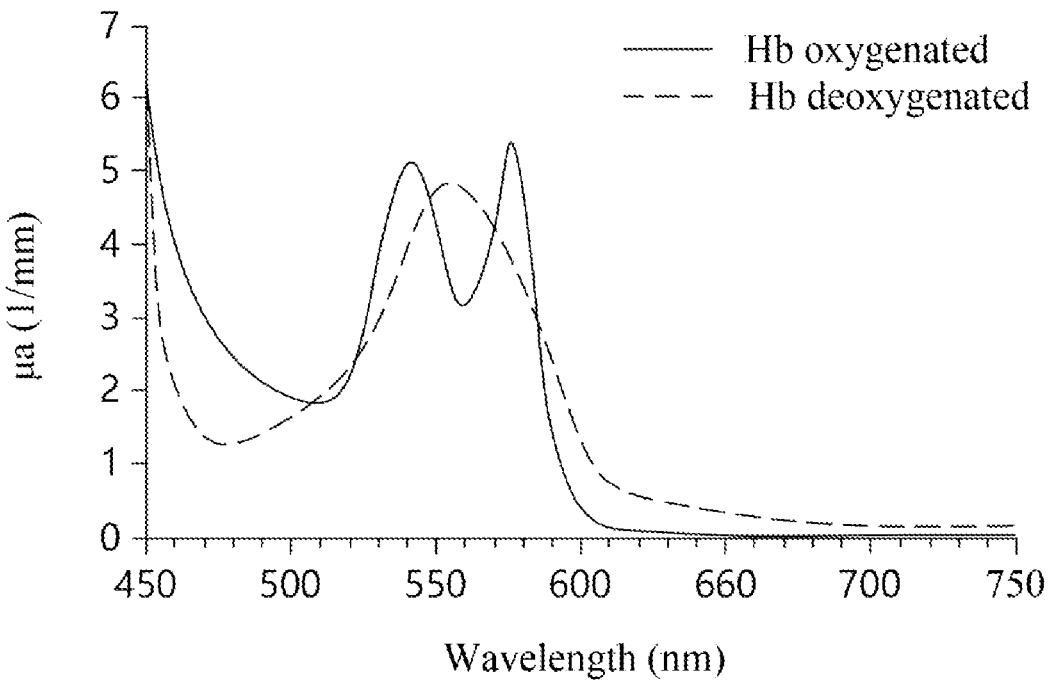
FIG. 15 is a diagram illustrating absorbance of hemoglobin and oxygen hemoglobin in a visible light band.

FIG. 15 is a diagram illustrating absorbance of hemoglobin and oxygen hemoglobin in a visible light band.

According to an embodiment, the Red channel may be a channel including at least a part of a wavelength band of 620 nm to 750 nm, the Green channel may be a channel including at least a part of a wavelength band of 495 nm to 570 nm, and the Blue channel may be a channel including at least a part of a wavelength band of 450 nm to 495 nm, but is not limited thereto, and may be color channels that are commonly understood as the Red channel, the Green channel, and the Blue channel.

Referring to FIG. 15, absorbance of hemoglobin and oxygen hemoglobin according to a wavelength band of light may be seen. For example, as shown in FIG. 18, absorbance of hemoglobin and oxygen hemoglobin for light of a wavelength band of 550 nm included in the Green channel may be higher than absorbance of hemoglobin and oxygen hemoglobin for light of a wavelength band of 650 nm included in the Red channel.

In addition, for example, as shown in FIG. 18, absorbance of hemoglobin and oxygen hemoglobin for light of a wavelength band of 550 nm included in the Green channel may be higher than absorbance of hemoglobin and oxygen hemoglobin for light of a wavelength band of 470 nm included in the Blue channel.

In addition, when blood is delivered to the entire body by heart beat, the volume of the blood vessel may change or the amount of blood included in the blood vessel may change due to the flow of blood.

Therefore, the color channel value including the wavelength band of light absorbed by the hemoglobin and oxygen hemoglobin included in the blood may be relatively greatly changed due to the change in the amount of blood due to the heart beat.

On the other hand, the color channel value including the wavelength band of light absorbed by the hemoglobin and oxygen hemoglobin included in the blood may be relatively smally changed due to the change in the amount of blood due to the heart beat.

Therefore, according to an embodiment, at least two color channels for reducing noise may be selected in consideration of absorbance of hemoglobin and oxygen hemoglobin.

For example, according to an embodiment, in order to reduce noise, a difference value between a Green channel value having a relatively high absorption by hemoglobin and oxygen hemoglobin and a Red channel value having a relatively low absorption by hemoglobin and oxygen hemoglobin may be used.

In addition, for example, according to an embodiment, in order to reduce noise, a difference value between a Green channel value having a relatively high absorption by hemoglobin and oxygen hemoglobin and a Blue channel value having a relatively low absorption by hemoglobin and oxygen hemoglobin may be used.

In addition, for example, according to an embodiment, in order to reduce noise, a difference value between a Blue channel value having a relatively high absorption by hemoglobin and oxygen hemoglobin and a Red channel value having a relatively low absorption by hemoglobin and oxygen hemoglobin may be used.

In addition, for example, according to an embodiment, a difference value between the Green channel value and the Red channel value and a difference value between the Green channel value and the Blue channel value may be simultaneously used.

Although the above examples are described based on the difference value, a processing value processed by using a weight to each channel value may be used in addition to the difference value in order to reduce noise caused by movement of a measured person and noise caused by external light.

For example, a processing value processed by using a weight to each channel value may be used as shown in Equation 5 below.

$$\text{Processing value} = a_{JI} \cdot \text{Red channel value} + b \cdot \text{Blue channel value} + c \cdot \text{Green channel value} \qquad \text{Equation 5}$$

In addition, in order to efficiently remove noise caused by movement of a measured person and noise caused by external light, a value a, b, c may be determined to be $a+b+c=0$, which may advantageously reduce noise because each channel value may include noise caused by movement of a single image frame and noise caused by external light of a similar degree, and thus may be advantageous in effectively reducing noise.

5.2 Various Embodiments of Obtaining Characteristic Values

In order to reduce noise caused by movement of a measured person and noise caused by external light intensity, a characteristic value may be obtained.

In this case, the characteristic value may be obtained for at least a part of an image frame group among the obtained plurality of image frames.

In addition, the characteristic value may be a value indicating a characteristic of the obtained color channel value or the processing value. For example, the characteristic value may mean an average value, a deviation value, a standard deviation value, or the like of the color channel value or the processing value included in the image frame group, but is not limited thereto.

FIG. 16 is a diagram for describing a method of obtaining a characteristic value according to an embodiment.

1601 of FIG. 16 is a graph illustrating a color channel value obtained according to an embodiment, and more specifically, a graph illustrating a difference value between a Green channel value and a Red channel value. However, this is only illustrated as a difference value between a Green channel value and a Red channel value for convenience of description, and may be a variety of color channel values, difference values, processing values, or the like, without being limited thereto.

Referring to 1601 of FIG. 16, a difference value between a Green channel value and a Red channel value (hereinafter, referred to as a 'G-R value') will be described. It can be seen that the magnitude of change of the value may not be constant over time.

In this case, the value of the G-R may not be constant by the movement of the measured party. For example, if the movement of the measured party is small, the change of the G-R value may be small, and if the movement of the measured party is large, the change of the G-R value may be large, but is not limited thereto.

In addition, the value of the G-R may not be constant according to the intensity of the external light. For example, if the intensity of the external light is weak, the change of the G-R value may be small, and if the intensity of the external light is strong, the change of the G-R value may be large, but is not limited thereto.

Accordingly, the characteristic value may be extracted to reduce noise caused by the movement of the measured party or the intensity of the external light.

In addition, a window for the characteristic value may be set to extract the characteristic value.

In this case, the window for the characteristic value may mean a predetermined time interval and may mean a predetermined number of frames, but is not limited thereto, and may mean a window for setting at least a part of a frame group among a plurality of frames to obtain the characteristic value.

1602 of FIG. 16 is a schematic diagram for describing a window for a characteristic value, and more particularly, a schematic diagram for describing a window for a characteristic value set to 18 image frames obtained by dividing 180 image frames by 10 equals. However, this is merely illustrative of the window for the characteristic value set to 18 image frames obtained by dividing 180 image frames by 10 for convenience of description, and is not limited thereto, and the window for the characteristic value may be set in various methods and numbers.

Referring to 1602 of FIG. 16, the obtained plurality of image frames may be set as a group by the window for the characteristic value. For example, as illustrated in 1601 of FIG. 16, 180 image frames may be set as a group including 18 image frames by the window for the characteristic value. More specifically, the first image frame to the 18th image frame may be included in the first image frame group 2210 and the 19th image frame to the 36th image frame may be included in the second image frame group 2220, but is not limited thereto.

In this case, the characteristic value may be obtained for the image frame group set by the window for the characteristic value. For example, the characteristic value may be obtained for color channel values for the first image frame group 2210 and the color channel values for the second image frame group 2220.

In addition, for example, when the characteristic value is an average value, an average value of the color channel value for the image frame group may be obtained. More specifically, the average values of the G-R values for the first to 18th image frames included in the first image frame group 2210 may be obtained and the average values of the G-R values for the 19th to 36th image frames included in the second image frame group 2220 may be obtained, but is not limited thereto.

Further, for example, when the characteristic value is a standard deviation value, a standard deviation value of a color channel value for an image frame group may be obtained. More specifically, the standard deviation values of G-R values for the first to eighth image frames included in the first image frame group 2210 may be obtained, and the standard deviation values of G-R values for the nineteenth to sixteenth image frames included in the second image frame group 2220 may be obtained, but the present invention is not limited thereto.

However, the present invention is not limited to the above examples, and various characteristic values may be obtained for an image frame group.

Further, the characteristic value may be obtained for at least some image frames included in an image frame group divided by a window for the characteristic value. For example, the characteristic value may be obtained for a color channel value for at least some image frames among 18 image frames included in the first image frame group 2210 and may be obtained for a color channel value for at least some image frames among 18 image frames included in the second image frame group 2220.

Further, for example, when the characteristic value is a deviation value, a deviation value of a color channel value for at least some image frames included in an image frame group may be obtained. More specifically, a deviation value of a G-R value of a first image frame included in a first image frame group with respect to an average of a G-R value of the first image frame group 2210 may be obtained, and a deviation value of a G-R value of a nineteenth image frame included in a second image frame group with respect to an average of a G-R value of the second image frame group 2220 may be obtained, but the present invention is not limited thereto.

Further, for example, when the characteristic value is a deviation value, a deviation value of a color channel value for at least some image frames included in an image frame group may be obtained. More specifically, a deviation value of a G-R value of a first image frame included in a first image frame group with respect to an average of a G-R value of the first image frame group 2210 may be obtained, and a deviation value of a G-R value of a second image frame included in the first image frame group 2210 may be obtained, but the present invention is not limited thereto.

Further, the obtained characteristic value may be normalized.

For example, when the characteristic value is a deviation value, the deviation value may be normalized by a standard deviation value. More specifically, when a deviation value of a G-R value of a first image frame included in a first image frame group 2210 with respect to an average of a G-R value of the first image frame group 2210 is obtained, the deviation value of the G-R value of the first image frame may be normalized by a standard deviation value of the first image frame group 2210, but the present invention is not limited thereto and may be normalized in various ways.

Further, when normalized as above, the magnitude of the variation amount may be normalized to better reflect a change in value due to heartbeat, and noise due to movement of a measured person and noise due to a change in intensity of external light may be effectively reduced.

1603 of FIG. 16 is a graph showing a characteristic value obtained according to an embodiment, and more specifically, is a graph showing a deviation value obtained based on a G-R value. However, this is merely illustrative of a deviation value obtained based on the G-R value for convenience of description, and the present invention is not limited thereto, and may be various characteristic values obtained based on various color channel values, difference values, and processing values.

Referring to 1603 of FIG. 16, it can be seen that the magnitude of the change in the value is more constant compared to 1601 of FIG. 16.

Therefore, obtaining the above-described characteristic value may reduce noise due to movement of the measured person and noise due to change in the intensity of the external light, and may better reflect the change in the value due to heartbeat.

Figure 17:
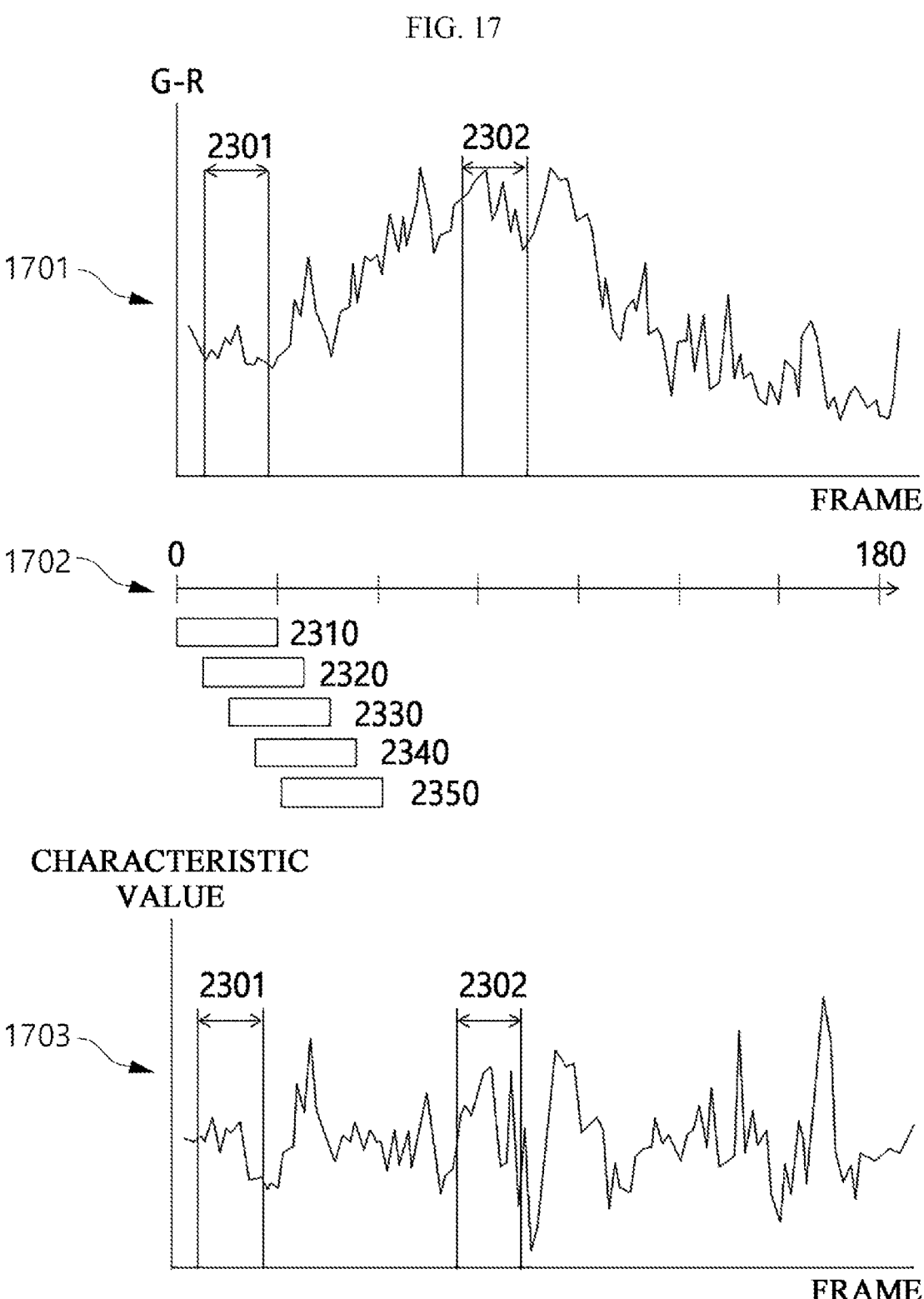
FIG. 17 is a diagram illustrating a characteristic value obtaining method according to another embodiment.

FIG. 17 is a diagram for describing a method of obtaining a characteristic value according to another embodiment.

1701 of FIG. 17 is a graph illustrating a color channel value obtained according to an embodiment, and more specifically, is a graph illustrating a difference between a Green channel value and a Red channel value. However, this is merely illustrative of a difference between a Green channel value and a Red channel value for convenience of description, and the present invention is not limited thereto, and may be various color channel values, difference values, and processing values.

Referring to 1701 of FIG. 17, a difference between a Green channel value and a Red channel value (hereinafter, referred to as a 'G-R value') is described. It can be seen that the magnitude of the change in the value may not be constant over time.

In this case, the value of the G-R may not be constant due to movement of the measured person. For example, the overall G-R value may be small in the time period 2302 in which the measured person is located in the first state, and the overall G-R value may be large in the time period 2302 in which the measured person is located in a second state different from the first state, but is not limited thereto.

In addition, the value of the G-R may not be constant depending on the intensity of the external light. For example, the intensity of the external light in the time period 2302 in which the measured person is located in the first state may be different from the intensity of the external light in the time period 2302 in which the measured person is located in the second state, and thus the overall G-R value may be different, but is not limited thereto.

Therefore, the characteristic value may be extracted to reduce noise due to movement of the measured person or the intensity of the external light.

In addition, a window for the characteristic value may be set to extract the characteristic value.

In this case, the window for the characteristic value may mean a preset time period and may mean a preset number of frames, but is not limited thereto, and may mean a window for setting at least a part of a frame group among a plurality of frames to obtain the characteristic value.

In addition, at least a part of the frame groups set by the window may at least partially overlap.

1702 of FIG. 17 is a schematic diagram for describing a window for a characteristic value, and more specifically, a schematic diagram for describing a window for a characteristic value set to a size obtained by dividing 180 image frames by 8 is illustrated. However, this is merely illustrative of a window for a characteristic value set to a size obtained by dividing 180 image frames by 8 for convenience of description, and the window for the characteristic value may be set in various ways and sizes.

Referring to 1702 of FIG. 17, the obtained plurality of image frames may be set as a group by a window for the characteristic value. For example, as illustrated in 1702 of FIG. 17, 180 image frames may be set as a group including 22 or 23 image frames by a window for the characteristic value. More specifically, the first image frame to the second image frame may be included in the first image frame group 2310.

Referring to 1702 of FIG. 17, the image frame group set by the window for the characteristic value may overlap at least some of the image frame groups. For example, as illustrated in 2002 of FIG. 20, the first image frame to the second image frame may be included in the first image frame group 2310, the sixth image frame to the twenty-eighth image frame may be included in the second image frame group 2320, the twelfth image frame to the third image frame may be included in the third image frame group 2330, and the seventeenth image frame to the 39th image frame group 2340, but the present disclosure is not limited thereto.

Referring to 1702 of FIG. 17, the image frame group set by the window for the characteristic value may not overlap. For example, as illustrated in 2002 of FIG. 20, the first image frame to the second image frame may be included in the first image frame group 2310, the third image frame to the fourteenth image frame may be included in the fifth image frame group 2350, but the present disclosure is not limited thereto.

In this case, the characteristic value may be obtained for the image frame group set by the window for the characteristic value, and may also be obtained for at least some image frames included in the image frame group, but details thereof may be applied to the above descriptions, and thus redundant descriptions thereof will be omitted.

However, the processing of the characteristic values obtained for the image frames included in the at least partially overlapping image frame groups will be described in detail below.

When the characteristic value is obtained, a plurality of characteristic values may be obtained for the image frames included in the region where the at least two image frame groups overlap.

For example, at least two characteristic values may be obtained for the sixth to the twenty-second image frames where the first image frame group 2310 and the second image frame group 2320 overlap.

More specifically, for the sixth image frame, a first deviation value may be obtained, which is a deviation value of the G-R value of the sixth image frame with respect to the G-R value average of the first image frame group 2310, and a second deviation value may be obtained, which is a deviation value of the G-R value of the sixth image frame with respect to the G-R value average of the second image frame group 2320, but the present disclosure is not limited thereto.

In addition, the obtained plurality of characteristic values may be obtained as one characteristic value through a calculation. For example, the deviation value of the sixth image frame may be obtained by adding the first deviation value and the second deviation value, but the present disclosure is not limited thereto.

In addition, the above operations may be applied to obtain a characteristic value for an image frame included in the region where the plurality of image frame groups overlap, such as three, four, etc.

In addition to the above-described operation, a sliding window method that may be generally understood may be applied.

1703 of FIG. 17 is a graph illustrating a characteristic value obtained according to an embodiment, and more particularly, is a graph illustrating a deviation value obtained based on a G-R value. However, this is merely illustrative of the deviation value obtained based on the G-R value for convenience of description, and is not limited thereto, and may be various characteristic values obtained based on various color channel values, difference values, and processing values.

Figure 20:
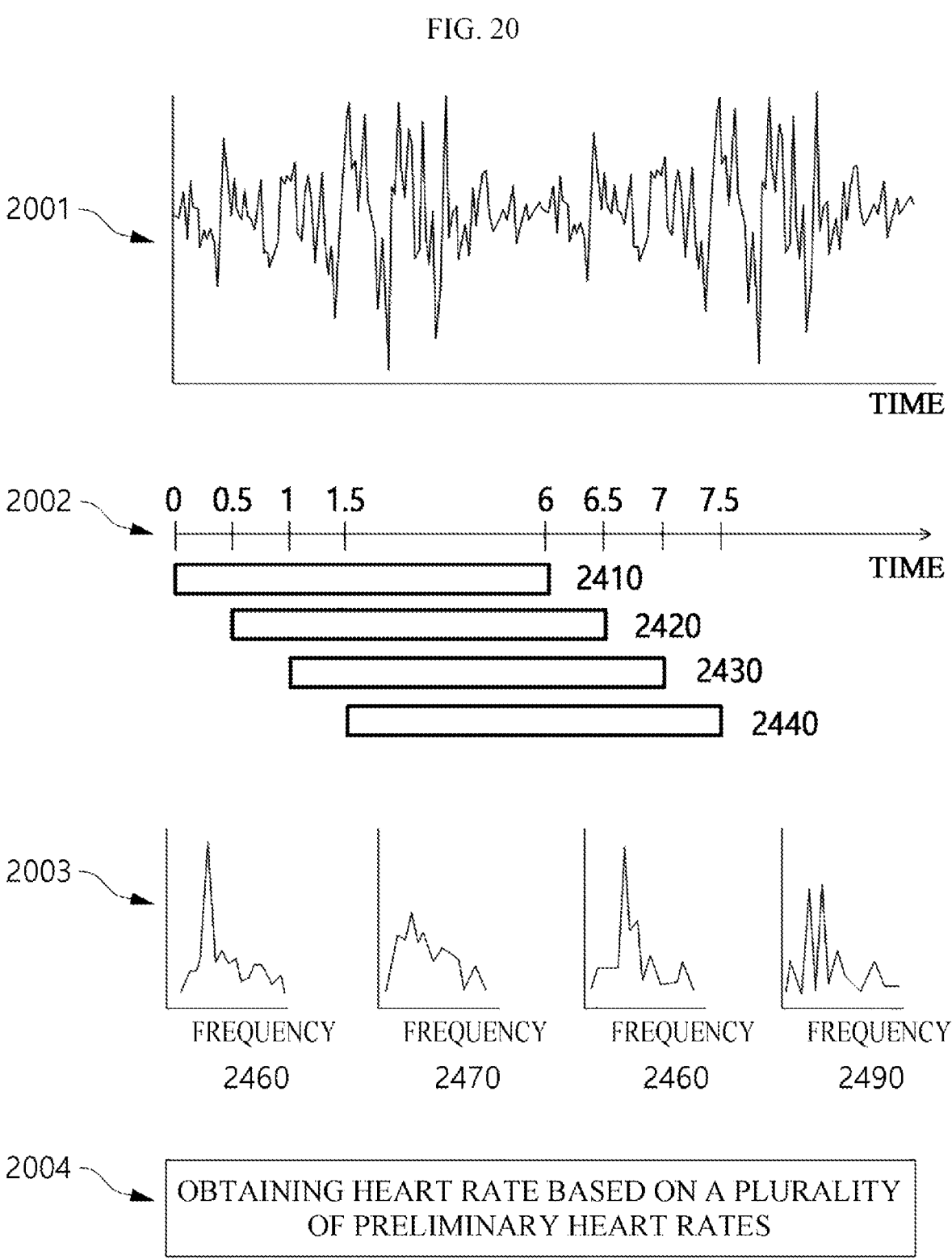
FIG. 20 is a diagram illustrating a heart rate obtaining method according to an embodiment.

Referring to 1703 of FIG. 17, it can be seen that the size of the overall value becomes constant as compared with 2001 of FIG. 20.

More specifically, the overall characteristic value in the time period 2302 in which the subject is positioned in the first state may be similar to the overall characteristic value in the time period 2302 in which the subject is positioned in the second state.

Therefore, as described above, the obtaining of the characteristic value may reduce noise due to movement of the subject and noise due to changes in external light intensity, and may better reflect a change in value due to heartbeat.

5.3 Various Embodiments of a Method of Using a Plurality of Characteristic Values The characteristic value obtained according to the above-described methods may be affected by a basic color channel value, a difference value, and a processing value. Therefore, obtaining a plurality of characteristic values based on various color channel values, difference values, and processing values and using the plurality of characteristic values may enable more accurate obtaining of a bioindex.

FIG. 18 is a diagram for describing a method of using a plurality of characteristic values.

1801 of FIG. 18 is a graph illustrating two characteristic values obtained according to an embodiment, and more particularly, is a graph illustrating a first characteristic value obtained based on a G-R value and a second characteristic value obtained based on a G-B value. However, this is merely illustrative of the above-described description, and is not limited thereto, and may be a characteristic value obtained based on various color channel values, difference values, and processing values.

In this case, the first characteristic value obtained based on the G-R value may be affected by the G-R value. For example, when the external light is light close to the Blue channel, the G-R value may not be able to reflect a change in blood due to heartbeat.

Alternatively, for example, the change in blood due to heartbeat may be reflected by being affected by a difference in absorbance of the Green channel and absorbance of the Red channel.

In addition, the second characteristic value obtained based on the G-B value may be affected by the G-B value. For example, when the external light is light close to the Red channel, the G-B value may not be able to reflect a change in blood due to heartbeat.

Alternatively, for example, the change in blood due to heartbeat may be reflected by being affected by a difference in absorbance of the Green channel and absorbance of the Blue channel.

Further, referring to 1801 of FIG. 18, the first characteristic value and the second characteristic value may have a complementary relationship. For example, in a section in which the first characteristic value does not well reflect the change according to heartbeat, the second characteristic value may well reflect the change according to heartbeat, and vice versa.

Therefore, the first characteristic value and the second characteristic value may be used to reduce noise according to the change of the wavelength of the external light or to better reflect the change of the blood according to heartbeat.

1802 of FIG. 18 is a graph illustrating a third characteristic value obtained using the first characteristic value and the second characteristic value, and more specifically, a graph illustrating a third characteristic value obtained by adding the first characteristic value and the second characteristic value. However, this is only specifically illustrated for convenience of description, and the present invention is not limited thereto.

In addition, the third characteristic value may be obtained based on an operation of the first characteristic value and the second characteristic value. For example, the third characteristic value may be obtained based on a sum operation of the first characteristic value and the second characteristic value, but is not limited thereto, and may be obtained based on various operations such as a difference operation, a product operation, and the like.

In addition, the third characteristic value may be obtained by assigning various weights to the first characteristic value and the second characteristic value. For example, the third characteristic value may be obtained based on Equation 6 below, but is not limited thereto.

$$\text{Third characteristic value}=a\cdot\text{first characteristic value}+b\cdot\text{second characteristic value} \qquad \text{Equation 6}$$

Referring to FIG. 18, the third characteristic value may be more well reflected a change of the blood according to heartbeat than the first characteristic value and the second characteristic value, and may reduce noise according to the change of the wavelength of the external light.

5.4 Various Embodiments of a Method for Obtaining Heart Rate

In order to obtain the heart rate from the data obtained from the above-described methods, it may be necessary to detect a periodic change according to heartbeat. For example, in order to obtain the heart rate from the obtained characteristic value, it is necessary to obtain the wavelength or frequency component most contained in the characteristic value.

Figure 19:
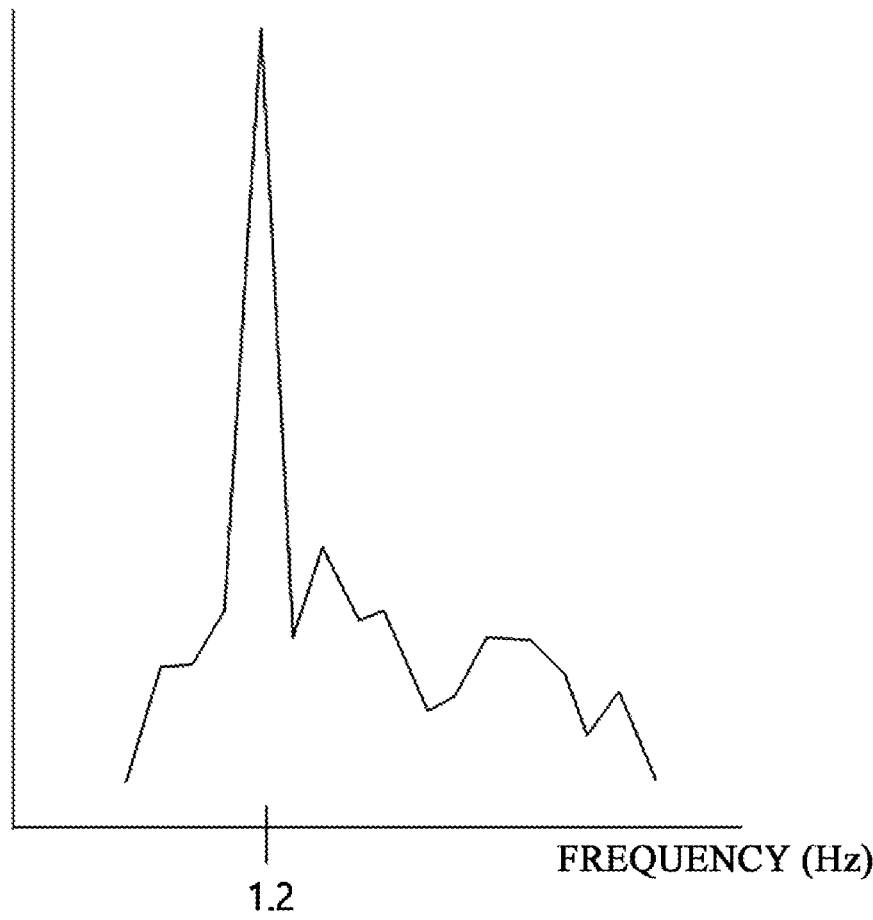
FIG. 19 is a graph obtained by extracting a frequency component from a graph of the characteristic values.

FIG. 19 is a graph obtained by extracting a frequency component from a graph of the characteristic value illustrated in 1802 of FIG. 18. More specifically, FIG. 19 is a graph obtained by transforming the graph of the characteristic value into a frequency domain by performing a fast Fourier transform. However, this is specifically illustrated by specifying the fast Fourier transform for convenience of description, and the graph of the characteristic value may be transformed according to a fast Fourier transform (FFT), a discrete Fourier transform (DFT), a short time Fourier transform (STFT), and the like, but is not limited thereto.

In addition, the graph of the characteristic value may be transformed into the frequency domain as illustrated in FIG. 19.

In this case, a frequency index having the highest intensity may be obtained, and the heart rate may be obtained by Equation 7 below.

$$\text{Heart rate}=\text{frequency index}\cdot 60 \qquad \text{Equation 7}$$

For example, as illustrated in FIG. 19, when the frequency index having the highest intensity is 1.2 Hz, the heart rate may be 72 bpm.

In addition, the graph of the characteristic value may be transformed into a frequency*measurement time domain, although not illustrated in FIG. 19.

In this case, a wavelength index having the highest intensity may be obtained, and the heart rate may be obtained by Equation 8 as follows.

$$\text{Heart rate} = \frac{\text{frequency index}}{\text{measurement time}} \cdot 60 \qquad \text{Equation 8}$$

For example, although not shown in FIG. 19, when the wavelength index having the highest intensity is 8, and the measurement time is 6.6 seconds, the heart rate may be 8/6.6*60 and may be 72 bpm.

In addition to the above example, various equations for obtaining the heart rate may be used.

In addition, the supplemental heart rate may be obtained to obtain the heart rate. In this case, the supplemental heart rate may be a calculated heart rate based on the basis for obtaining the heart rate.

FIG. 20 is a diagram for describing a method of obtaining a heart rate according to an embodiment.

Before explaining, the 'preliminary heart rate' described below may mean a heart rate obtained according to a method of obtaining a heart rate, and may mean a heart rate based on the basis for obtaining one heart rate. For example, at least two heart rates obtained according to the above-described method of obtaining a heart rate may be a first supplemental heart rate and a second supplemental heart rate based on the basis for obtaining one final heart rate, but the present invention is not limited thereto.

In addition, the supplemental heart rate may be a final heart rate, and a final heart rate may be obtained based on a plurality of supplemental heart rates.

2001 of FIG. 20 is a graph illustrating a value obtained by time series data. For example, 2001 of FIG. 20 may mean a color channel value obtained by time series data, but the present invention is not limited thereto, and may mean a difference value obtained by time series data, a processing value, or a characteristic value obtained by time series data.

Since the above-described description may be applied to a method of converting a graph illustrating a value obtained by time series data as illustrated in 2001 of FIG. 20 into a wavelength domain or a frequency domain, redundant descriptions will be omitted.

2002 of FIG. 20 is a schematic diagram for describing a window for a supplemental heart rate, and more specifically, a schematic diagram for describing a window for a supplemental heart rate set to a size of 6 seconds. However, this is only a specific example for convenience of description, and the present invention is not limited thereto, and the window may be set to various sizes.

In this case, the window for the supplemental heart rate may mean a preset time interval, and may mean a preset frame number, but the present invention is not limited thereto, and may mean a window for setting at least a part of a frame group among a plurality of frames to obtain the supplemental heart rate.

Referring to 2002 of FIG. 20, the obtained plurality of image frames may be set into groups by the window for the supplemental heart rate. For example, as illustrated in 2002 of FIG. 20, an image frame obtained between 0 seconds and 6 seconds may be included in a first image frame group 2410, but the present invention is not limited thereto.

Referring to 2002 of FIG. 20, the image frame group set by the window for the preliminary heart rate may overlap at least some of the image frame groups. For example, as illustrated in 2001 of FIG. 20, an image frame obtained between 0 seconds and 6 seconds may be included in the first image frame group 2410, an image frame obtained between 0.5 seconds and 6.5 seconds may be included in the second image frame group 2420, an image frame obtained between 1 second and 7 seconds may be included in the third image frame group 2430, and an image frame obtained between 1.5 seconds and 7.5 seconds may be included in the fourth image frame group 2440, but is not limited thereto.

In this case, the preliminary heart rate may be obtained for the image frame group set by the window for the preliminary heart rate. For example, the first preliminary heart rate may be obtained based on characteristic values obtained from image frames included in the first image frame group 2410.

In addition, in order to obtain the preliminary heart rate, the value obtained as the time series data in each image frame group may be converted into a wavelength domain or a frequency domain. For example, the value obtained as the time series data in the first image frame group may be converted into the first frequency data 2460, the value obtained as the time series data in the second image frame group may be converted into the second frequency data 2470, the value obtained as the time series data in the third image frame group may be converted into the third frequency data 2480, and the value obtained as the time series data in the fourth image frame group may be converted into the fourth frequency data 2490, but is not limited thereto.

In addition, since the above-described heart rate obtaining method may be applied to obtaining the first to fourth preliminary heart rates from the first to fourth frequency data 2460, 2470, 2480, and 2490, redundant descriptions will be omitted.

In addition, the heart rate may be obtained based on the plurality of preliminary heart rates. For example, the heart rate may be obtained by performing an operation on the plurality of preliminary heart rates, and more specifically, the heart rate may be obtained by performing an operation for extracting an average, a maximum value, a minimum value, and the like of the first to fourth preliminary heart rates, but is not limited thereto.

In addition, the heart rate may be obtained based on the plurality of preliminary heart rates. For example, the heart rate may be obtained by performing an operation on the remaining heart rate except for a preliminary heart rate having a different ten digit among the obtained plurality of preliminary heart rates.

More specifically, when the first preliminary heart rate is 72 bpm, the second preliminary heart rate is 80 bpm, the third preliminary heart rate is 75 bpm, and the fourth preliminary heart rate is 73 bpm, the heart rate may be obtained by performing an operation on the first, third, and fourth preliminary heart rates, except for the second preliminary heart rate having a different ten digit. In this case, the operation may be an operation for extracting an average, a maximum value, a minimum value, and the like.

In addition, the heart rate may be obtained based on the plurality of preliminary heart rates. For example, when 10 digits of the obtained four supplemental heartrates are paired and different, a calculation for the remaining heartrates may be performed except for a pair of supplemental heartrates in which 10 digits of the obtained four supplemental heartrates are different from previously obtained heartrates to obtain the heart rates.

More specifically, when the first supplemental heartrates are 72 bpm, the second supplemental heartrates are 80 bpm, the third supplemental heartrates are 85 bpm, and the fourth supplemental heartrates are 73 bpm, and the previously obtained heartrates are 75 bpm, calculation for the first and fourth supplemental heartrates may be performed except for the second and third supplemental heartrates to obtain the heart rates.

In addition, when a heart rate is obtained using a plurality of supplemental heartrates as described above, a heart rate that is more robust to noise and accurate may be obtained.

5.5 Various Embodiments of Outputting Heart Rate

The heart rate obtained by the above-described methods may be output through a display or the like, or may be transmitted to a terminal or a server using a communication unit. Hereinafter, for convenience of description, the operation will be described as an output of a heart rate.

When continuously performing real-time measurement on a heart rate, a correction may be performed on the output heart rate to impart stability and reliability to the measured heart rate.

In addition, when the output heart rate is corrected, even if a poor image is obtained in some of a plurality of image frames obtained, stability and reliability may be imparted to the obtained output heart rate.

Figure 21:
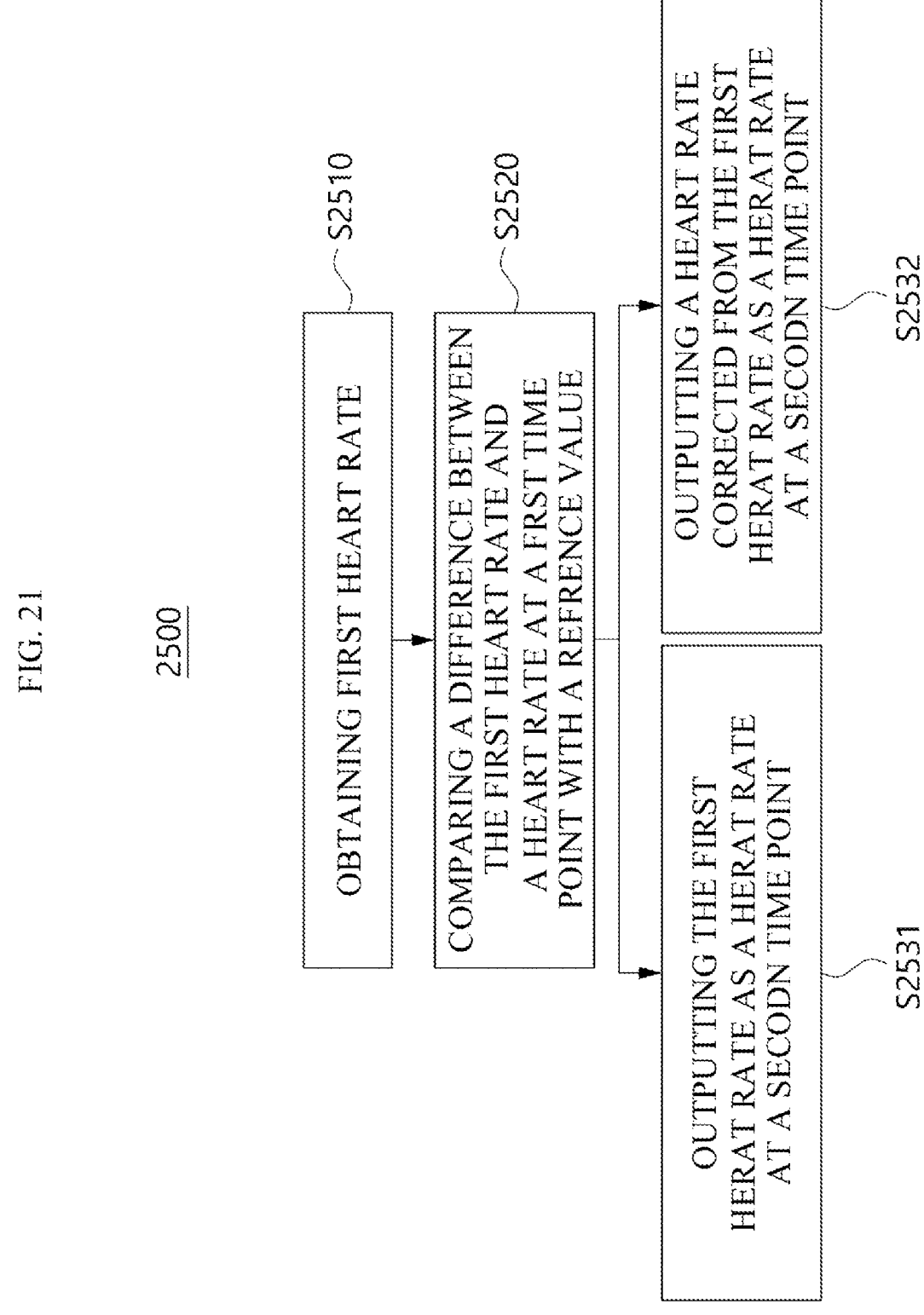
FIG. 21 is a flowchart illustrating a method of correcting an output heart rate according to an embodiment.

FIG. 21 is a flowchart illustrating a method for correcting an output heart rate according to an embodiment.

Referring to FIG. 21, the method 2500 for correcting an output heart rate according to an embodiment may include, but is not limited to, obtaining a first heart rate (S2510), and comparing a difference between the first heart rate and a first time point heart rate with a reference value (S2520).

Since the above-described methods for obtaining a heart rate may be applied to the step of obtaining the first heart rate (S2510), redundant descriptions will be omitted.

In comparing the difference between the first heart rate and the first time point heart rate with the reference value (S2520), the first time point heart rate may mean a heart rate obtained or output before the first heart rate is obtained. For example, when the first heart rate is obtained at 6.5 seconds, the first time point heart rate may be a heart rate obtained at 6 seconds, or a heart rate output at 6 seconds, but is not limited thereto.

In addition, the reference value may be determined as a predetermined numerical value or a predetermined ratio. For example, the reference value may be determined as 10, and in this case, it may be determined whether the difference between the first heart rate and the first time point heart rate exceeds 10, but is not limited thereto.

In addition, when the difference between the first heart rate and the first time point heart rate is equal to or less than the reference value, the step of outputting the first heart rate as a second time point heart rate (S2531) may be performed, and in this case, the second time point may be a time point later than the first time point.

For example, when the first time heart rate is 72 bpm, the first heart rate is 75 bpm, and the reference value is 10, the heart rate output at the second time may be 75 bpm, but is not limited thereto.

In addition, when the difference between the first heart rate and the first time heart rate exceeds the reference value, the step S2532 of outputting the heart rate corrected from the first time heart rate as the second time heart rate may be performed, and in this case, the second time heart rate may be a time later than the first time heart rate.

In addition, in order to obtain the heart rate corrected from the first time heart rate, an operation on the first time heart rate may be performed. For example, an operation such as adding or subtracting a predetermined value to or from the first time heart rate may be performed, but is not limited thereto.

For example, when the first time heart rate is 72 bpm, the first heart rate is 85 bpm, and the reference value is 10, the heart rate output at the second time may be 75 bpm with +3 bpm to the first time heart rate, but is not limited thereto.

In addition, for example, when the first time heart rate is 72 bpm, the first heart rate is 61 bpm, and the reference value is 10, the heart rate output at the second time may be 69 bpm with −3 bpm to the first time heart rate, but is not limited thereto.

5.6 Various Embodiments of Heartbeat Signal Extraction

The heartbeat signal may mean a signal that may be changed according to heartbeats, and may mean a signal that may be estimated to be changed according to heartbeats.

In addition, the heartbeat signal may be extracted based on the obtained plurality of image frames.

Figure 22:
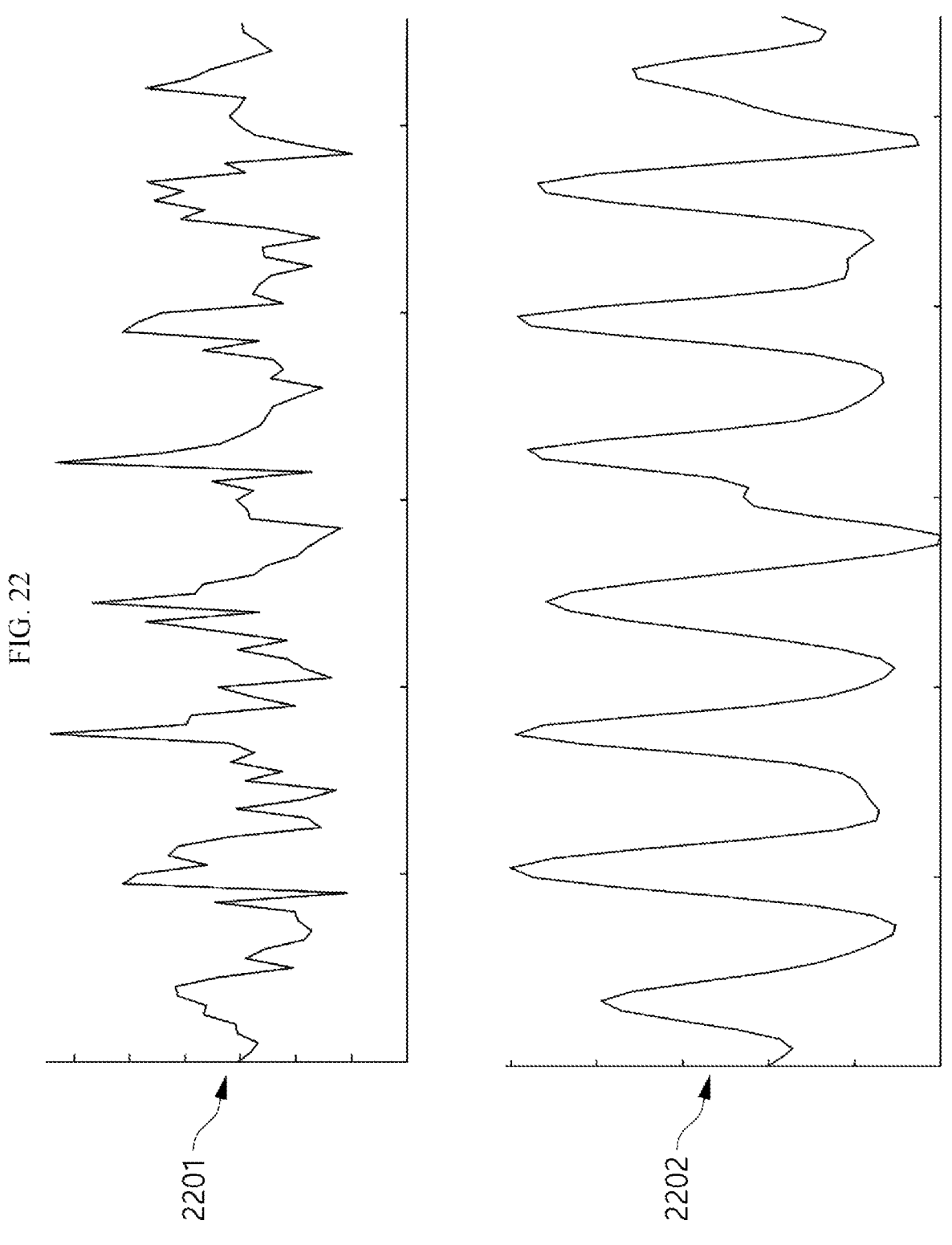
FIG. 22 is a diagram illustrating a heart rate signal extraction method according to an embodiment.

FIG. 22 is a diagram for describing a method of extracting a heartbeat signal according to an embodiment.

First, 2201 of FIG. 22 is a graph illustrating a value obtained by time series data. For example, 2201 of FIG. 22 may mean a color channel value obtained by time series data, but is not limited thereto, may mean a difference value obtained by time series data, a processing value, or may mean a characteristic value obtained by time series data.

In this case, the value obtained by the time series data may be extracted as a heartbeat signal through a band pass filter. More specifically, the value obtained by the time series data may be extracted as a heartbeat signal through a band pass filter of a frequency band or a wavelength band corresponding to the heartbeat rate.

In addition, the frequency band or the wavelength band corresponding to the heartbeat rate may be a commonly understandable frequency band or a wavelength band, but is not limited thereto, and may be a frequency band or a wavelength band determined based on the heartbeat rate obtained by the above-described methods.

For example, the common heartbeat rate may be 60 to 100 bpm, and the corresponding frequency band may be 1 Hz to 1.67 Hz, and a band pass filter corresponding thereto may be used, but is not limited thereto.

In addition, for example, when the obtained heartbeat rate is 72 bpm, the corresponding frequency is 1.2 Hz, and a frequency band may be set based on the frequency band. More specifically, when a frequency band in the range of 0.5 Hz is set, the frequency band may be set in the range of 0.95 Hz to 1.45 Hz, and a band pass filter corresponding to the frequency band may be used, but the present invention is not limited thereto.

2202 of FIG. 22 is a graph of a heart rate signal obtained by extracting a value obtained as the time series data illustrated in 2201 of FIG. 22 as a heart rate signal through a band pass filter.

Referring to 2202 of FIG. 22, it can be seen that the value obtained as the time series data may be extracted as the heart rate signal through the band pass filter.

5.7 Various Embodiments of a Method for Measuring Heart Rate Using Infrared Rays Basically, the above-described heart rate measurement methods may be used as a method for measuring heart rate using infrared rays.

Figure 23:
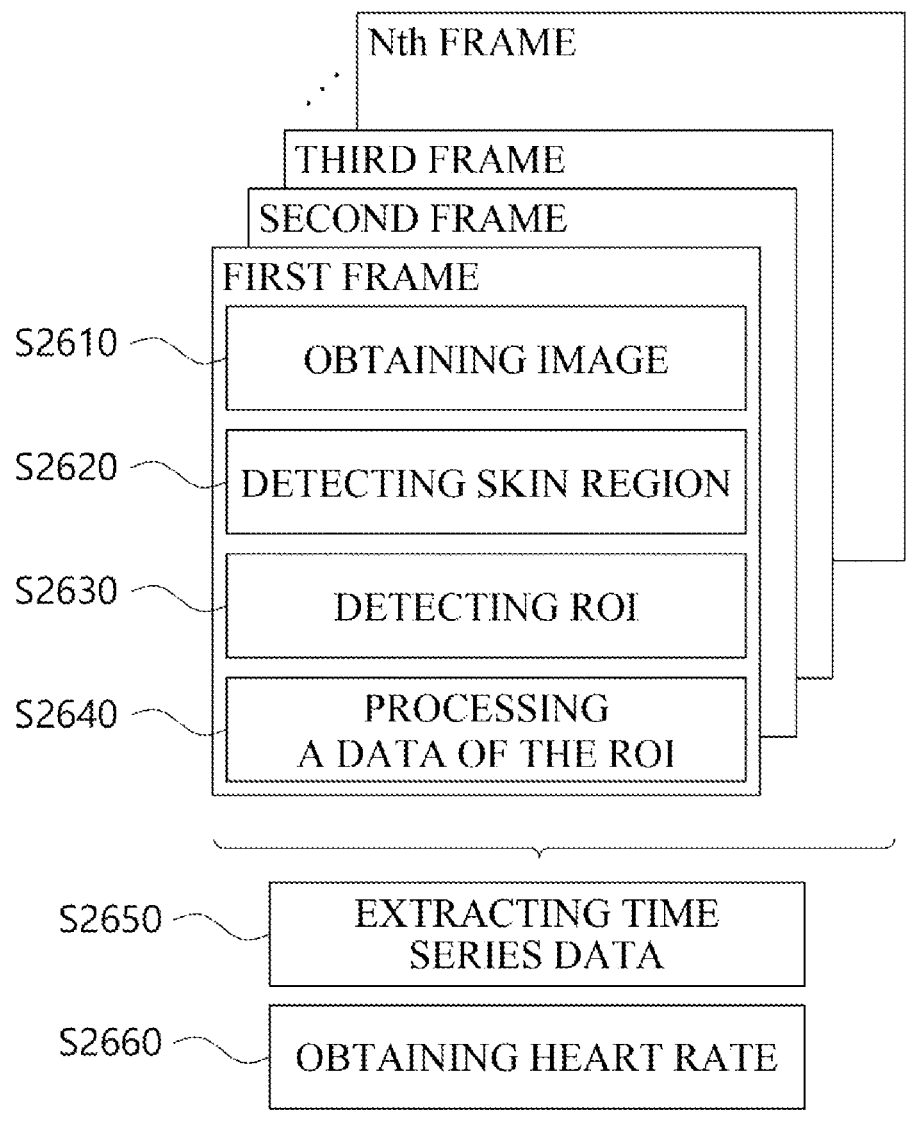
FIG. 23 is a diagram illustrating a heart rate obtaining method using infrared ray according to an embodiment.

FIG. 23 is a diagram for describing a method for obtaining heart rate using infrared rays according to an embodiment.

In this case, the infrared rays may be infrared rays in a near infrared region having a wavelength band of 750 nm to 3000 nm, but the present invention is not limited thereto, and may also be infrared rays in a middle infrared region, a far infrared region, and an extreme infrared region.

Referring to FIG. 23, the method 2600 for measuring heart rate using infrared rays according to an embodiment may include at least some of the following steps: obtaining an image (S2610), detecting a skin region (S2620), detecting a region of interest (S2630), and processing data for the region of interest (S2640), with respect to at least one image frame among the obtained plurality of image frames, but the present invention is not limited thereto.

In addition, the above-described descriptions may be applied to the obtaining of the image (S2610) and the detecting of the skin region (S2620), and thus redundant descriptions will be omitted.

In addition, detailed operations of the detecting of the region of interest (S2630) may be applied to the above-described methods for detecting the region of interest, and thus redundant descriptions will be omitted.

In addition, the detecting of the region of interest (S2630) may include detecting the first, second, and third region of interest, and may be performed on at least one image frame among the obtained plurality of image frames.

In addition, the first, second, and third region of interest may at least partially overlap with each other. For example, the first region of interest may be set to be included in the second and third region of interest, and the second region of interest may be set to be included in the third region of interest, but the present invention is not limited thereto, and the first to third region of interest may be set to at least partially overlap with each other.

In addition, the first, second, and third region of interest may be set not to overlap with each other. For example, the first region of interest and the second region of interest may be located up and down on a left ball of a subject, and the third region of interest may be located on a right ball of the subject, but the present invention is not limited thereto, and the first to third region of interest may be set not to overlap with each other.

In addition, detailed operations of the step of processing the data for the first, second, and third interest regions (S2640) may be applied to the methods for processing the data for the interest regions, and thus, redundant descriptions will be omitted.

In addition, the step of processing the data for the interest region (S2640) may be performed on at least one image frame among the obtained plurality of image frames.

In addition, the step of processing the data for the interest region (S2640) may be performed on the first, second, and third interest regions described above.

In addition, the IR intensity values for the first to third interest regions may be extracted for at least one image frame among the obtained plurality of image frames for processing the data for the first to third interest regions. In this case, the IR intensity value may be an average value of the IR intensity values of the pixels included in the first to third interest regions and may be referred to as an average pixel value.

In addition, when the method for processing the data for the interest region is applied, the IR intensity values for each interest region may correspond to the color channel values described above. For example, the IR intensity value of the first interest region may correspond to the Red channel value, the IR intensity value of the second interest region may correspond to the Green channel value, and the IR intensity value of the third interest region may correspond to the Blue channel value, but is not limited thereto.

In addition, for example, the G-R value may correspond to a difference value between the IR intensity value of the second interest region and the IR intensity value of the first interest region, and the G-B value may correspond to a difference value between the IR intensity value of the second interest region and the IR intensity value of the third interest region.

Accordingly, data may be processed based on the IR intensity values for each interest region, and detailed operations may be based on the data processing method for the interest region described above.

In addition, the heart rate measurement method 2600 using infrared rays according to an embodiment may include at least some of the steps of extracting time series data (S2650) and obtaining heart rate (S2660) for the image frame group of at least some of the obtained plurality of image frames, but is not limited thereto.

In this case, the step of extracting the time series data (S2650) and obtaining the heart rate (S2660) may be applied to the above descriptions, and thus, redundant descriptions will be omitted.

Figure 24:
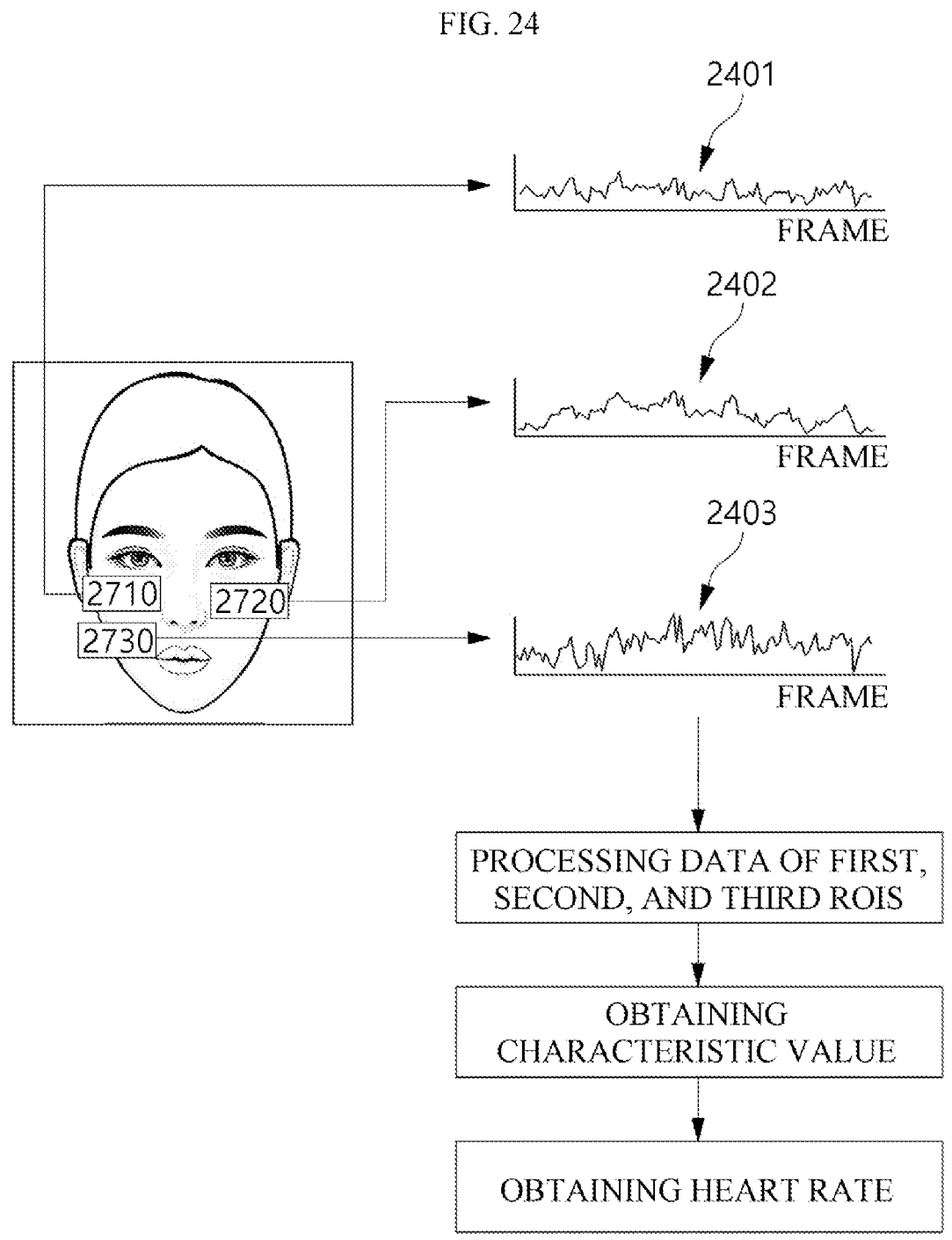
FIG. 24 is a diagram illustrating a heart rate obtaining method using infrared ray according to an embodiment.

FIG. 24 is a diagram for describing a method for obtaining heart rate using infrared rays according to an embodiment.

Referring to FIG. 24, at least two interest regions may be set in the face region of the subject. More specifically, the first interest region 2710, the second interest region 2720, and the third interest region 2730 may be set in the face region of the subject, but are not limited thereto.

In addition, the IR intensity values for the first to third interest regions 2710, 2720, and 2730 may be extracted.

For example, the IR intensity values (2401 of FIG. 24) of the first interest region 2710 may be extracted, the IR intensity values (2402 of FIG. 24) of the second interest region 2720 may be extracted, and the IR intensity values (2403 of FIG. 24) of the third interest region 2730 may be extracted, but the present invention is not limited thereto.

In addition, data of the first to third interest regions 2710, 2720, and 2730 may be processed based on the IR intensity values extracted for the first to third interest regions 2710, 2720, and 2730. However, the detailed operations thereof will be omitted from the descriptions of the redundant descriptions above.

In addition, a characteristic value may be obtained based on data processed for the first to third interest regions 2710, 2720, and 2730. However, the detailed operations thereof will be omitted from the descriptions of the redundant descriptions above.

In addition, a heart rate may be obtained using the characteristic values obtained based on the IR intensity values extracted for the first to third interest regions 2710, 2720, and 2730. However, the detailed operations thereof will be omitted from the descriptions of the redundant descriptions above.

6. A Method of Obtaining a Biometric Index According to an Embodiment

FIG. 25 is a flowchart illustrating a method of obtaining a biometric index according to an embodiment.

Referring to FIG. 25, a method of obtaining a biometric index according to an embodiment may include obtaining a plurality of image frames for a subject (S2810), obtaining first, second, and third color channel values (S2820), calculating a first difference value and a second difference value (S2830), obtaining a first characteristic value and a second characteristic value (S2840), obtaining time series data based on the first characteristic value and the second characteristic value (S2850), obtaining biosignal characteristic data based on the time series data (S2860), and obtaining a biometric index for the subject based on the biosignal characteristic data using a biometric index measurement model (S2870). In an embodiment, the steps may be performed by a biometric index obtaining device.

In this case, in the obtaining of the plurality of image frames for the subject (S2810), the plurality of images may be obtained by a camera. For example, the plurality of images may be obtained by a camera such as a visible light camera, an IR camera, or the like.

In addition, the plurality of images may be obtained from a camera disposed outside. For example, the plurality of images may be images obtained from a camera such as a visible light camera, an IR camera, or the like disposed outside.

In addition, the obtaining of the first, second, and third color channel values (S2820) may be performed on at least one image frame among the obtained plurality of image frames.

In this case, the first color channel value may mean an average pixel value for a first color channel of an image frame in which the step is performed, the second color channel value may mean an average pixel value for a second color channel of the image frame, and the third color channel value may mean an average pixel value for a third color channel of the image frame.

For example, the first color channel value may be a Green channel value, the second color channel value may be a Red channel value, and the third color channel value may be a Blue channel value, but the present invention is not limited thereto.

In addition, the calculating of the first difference value and the second difference value in operation S2830 may be performed on at least one image frame among the obtained plurality of image frames.

In this case, the first difference value may mean a difference value between a first color channel value and a second color channel value, for example, the first difference value may mean a difference value between a first color channel value and a second color channel value for the same image frame, but is not limited thereto.

More specifically, when the first color channel value is a Green channel value and the second color channel value is a Red channel value, the first difference value may be a G-R value, but is not limited thereto.

In addition, the second difference value may mean a difference value between a first color channel value and a third color channel value, for example, the second difference value may mean a difference value between a first color channel value and a third color channel value for the same image frame, but is not limited thereto.

More specifically, when the first color channel value is a Green channel value and the second color channel value is a Blue channel value, the second difference value may be a G-B value, but is not limited thereto.

In addition, the obtaining of the first characteristic value and the second characteristic value in operation S2840 may be performed on at least a part of an image frame group among the obtained plurality of image frames.

For example, the first characteristic value may be obtained for a first image frame group, and the first image frame group may mean an image frame group obtained for a predetermined time.

In addition, for example, the second characteristic value may be obtained for the first image frame group.

In addition, the first characteristic value may be obtained based on an average value of the first difference value for the first image frame group and a first difference value for an image frame included in the first image frame group.

For example, the first characteristic value may be a deviation value obtained based on an average value of the G-R value for the first image frame group and a G-R value for an image frame included in the first image frame group, but is not limited thereto.

In addition, the second characteristic value may be obtained based on an average value of the second difference value for the first image frame group and a second difference value for an image frame included in the second image frame group.

For example, the second characteristic value may be a deviation value obtained based on an average value of the G-B value for the second image frame group and a G-B value for an image frame included in the second image frame group, but is not limited thereto.

In addition, the first image frame group and the second image frame group may be the same as each other, but are not limited thereto and may be different from each other. That is, according to an embodiment, the first image frame group and the second image frame group may be the same.

In addition, the first characteristic value may be an average value, a standard deviation value, or the like for the first image frame group, but is not limited thereto.

In addition, the first characteristic value may be a deviation value or the like for at least a part of an image frame included in the first image frame group, but is not limited thereto.

In addition, the second characteristic value may be an average value, a standard deviation value, or the like for the second image frame group, but is not limited thereto.

In addition, the second characteristic value may be a deviation value for at least some image frames included in the second image frame group, but is not limited thereto.

In addition, the first and second characteristic values may be normalized. For example, the first characteristic value may be normalized using a standard deviation value for the first image frame group, but is not limited thereto.

In addition, for example, the second characteristic value may be normalized using a standard deviation value for the second image frame group, but is not limited thereto.

In operation S2850 of obtaining time series data based on the first characteristic value and the second characteristic value, the biometric index obtaining device may obtain time series data by performing an operation on the first characteristic value and the second characteristic value.

For example, the biometric index obtaining device may obtain a third characteristic value using the first characteristic value and the second characteristic value, and obtain time series data based on the third characteristic value. For example, the third characteristic value may be obtained based on a sum operation of the first characteristic value and the second characteristic value, but is not limited thereto, and may be obtained based on various operations such as a difference operation, a multiplication operation, and the like, or may be obtained by assigning various weights as in Equation 6 described above. For example, the biometric index obtaining device may obtain time series data for the third characteristic value as shown in 1802 of FIG. 18 in which the third characteristic value is configured in a time series. In addition, the time series data may be represented as a PPG signal or a rPPG signal according to an embodiment. The above-described description may be applied to operation S2850 of obtaining time series data based on the first characteristic value and the second characteristic value, and thus a detailed description thereof will be omitted.

In operation S2860 of obtaining biometric signal characteristic data based on the time series data, the biometric signal characteristic data may mean input data input from the time series data to a biometric index obtaining model to be described below. For example, the biometric signal characteristic data may mean features described with reference to FIGS. 7 and 8.

In an embodiment, the biometric index obtaining device may obtain target time series data based on the time series data, and obtain biometric signal characteristic data using the target time series data. Here, the target time series data may mean data obtained by processing the time series data to obtain more accurate biometric signal characteristic data.

Specifically, the biometric index obtaining device may perform filtering to reduce noise included in the time series data. More specifically, the biometric index obtaining device may filter the time series data using a bandpass filter. For example, the biometric index obtaining device may obtain time series data using a bandpass filter of a frequency band or a wavelength band corresponding to a heart rate. Here, the frequency band or the wavelength band corresponding to the heart rate may be a commonly understandable frequency band or a wavelength band, but is not limited thereto, and may be a frequency band or a wavelength band determined based on the heart rate obtained by the above-described methods. For example, the frequency band or the wavelength band corresponding to the heart rate may be a frequency band wavelength band corresponding to the heart rate of the measured person.

For example, the normal heart rate may be 60 to 100 bpm, the corresponding frequency band may be 1 Hz to 1.67 Hz, and the bandpass filter may be configured to perform filtering according to the frequency band.

In another example, the biometric index obtaining apparatus may perform Fourier transform on the time series data according to the above-described methods to obtain a frequency band corresponding to the heart rate of the measured person, and may filter the time series data using a bandpass filter in which filtering is performed according to the obtained frequency band.

For example, when the obtained heart rate of the measured person is 72 bpm, the frequency corresponding thereto is 1.2 Hz, and may set a frequency band based on the frequency band. More specifically, when a frequency band in the range of 0.5 Hz is set, the frequency band may be set to the range of 0.95 Hz to 1.45 Hz, and the bandpass filter corresponding thereto may be used for filtering, but the present invention is not limited thereto. The above-described description of FIG. 22 may be applied to the filtering of the time series data, and thus the detailed description thereof will be omitted.

In addition, the biometric signal measurement apparatus may divide the time series data into a plurality of detailed time series data in order to obtain the target time series data. Specifically, FIG. 26 is a diagram for describing time series data according to an embodiment.

Figure 26:
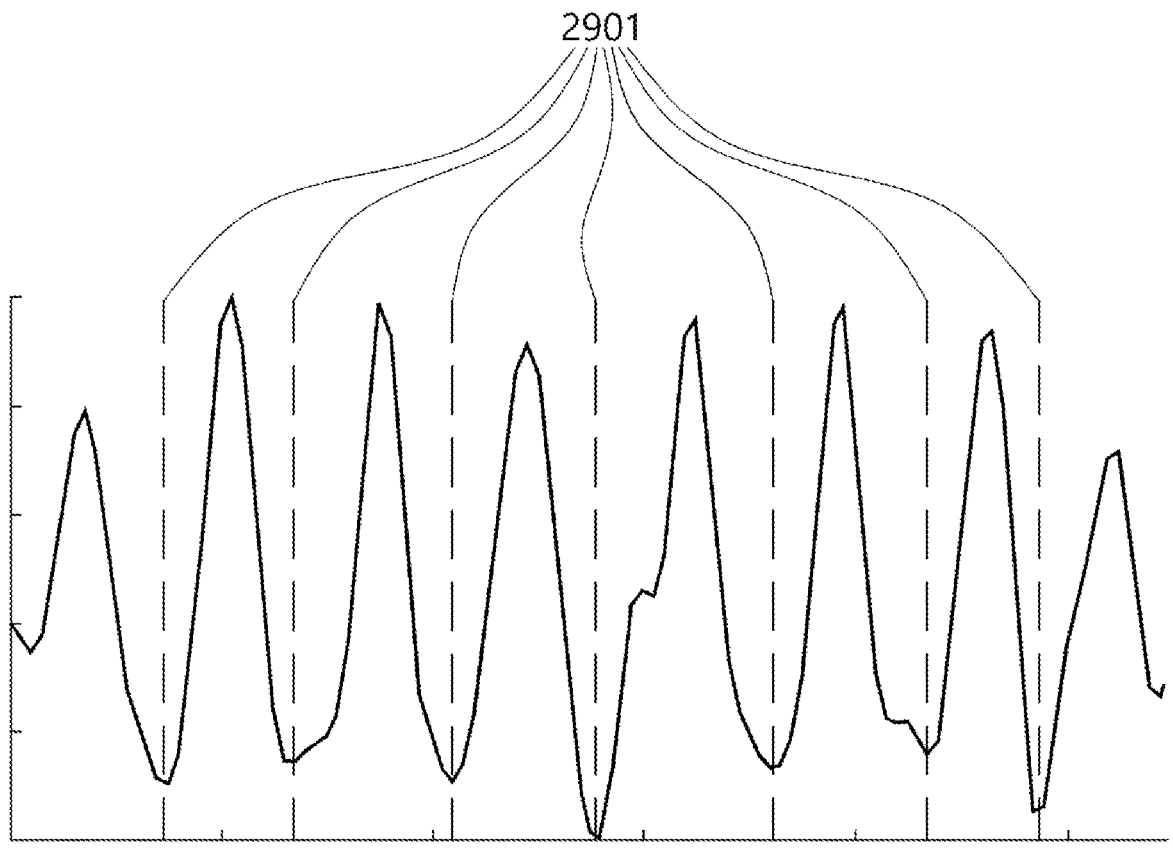
FIG. 26 is a diagram illustrating time series data according to an embodiment.

Referring to FIG. 26, the x-axis of the graph of FIG. 26 may indicate time, and the y-axis may indicate the size of the time series data. Even when the time series data is filtered, noise may be included in the filtered time series data. Accordingly, the biometric index obtaining apparatus may obtain the target time series data having the reduced noise based on the time series data. In an embodiment, the biometric index obtaining apparatus may obtain the detailed time series data using a tendency of a value of the time series data. For example, the time series data may be repeated in a section in which a value increases and decreases, and the biometric index obtaining apparatus may divide the time series data into a plurality of detailed time series data using minimum values of each section. For example, the time series data of FIG. 26 may be divided into a plurality of time series data based on minimum values of each section in which a value increases and decreases, as divided by the identification number 2901.

In addition, in an embodiment, the target time series data may be obtained based on the plurality of detailed time series data. For example, the biometric index obtaining apparatus may obtain detailed time series data satisfying a predetermined condition among the plurality of detailed time series data as the target time series data.

Specifically, FIG. 27 is a diagram for describing target time series data according to an embodiment.

Referring to FIG. 27, the biometric index obtaining apparatus may determine whether a highest value (or maximum value) of the detailed time series data is left of a section corresponding to the detailed time series data, i.e., whether the highest value of the detailed time series data is present between a start time point and an intermediate time point of the section corresponding to the detailed time series data, for each of the plurality of detailed time series data. In this case, when the highest value (or maximum value) of the detailed time series data is between the intermediate time point and the end time point of the section corresponding to the detailed time series data, the detailed time series data may not be selected as the target time series data. For example, 2701 of FIG. 27 is a graph illustrating detailed time series data. The x-axis of 2701 of FIG. 27 may indicate time, and the y-axis may indicate a value of the time series data. In the case of FIG. 27, the highest value 3010 of the detailed time series data may appear between the start time point 3001 and the intermediate time point 3002, and may not appear between the intermediate time point 3002 and the end time point 3003. In this case, the time series data of 2701 of FIG. 27 may satisfy at least some of the predetermined conditions.

In addition, as another example, the biometric index obtaining device may determine whether the detailed time series data includes a first maximum value and a second maximum value smaller than the first maximum value of the detailed time series data, for each of the plurality of detailed time series data. For example, in the example of 2701 of FIG. 27, the time series data may include the first maximum value 3010 and the second maximum value 3020. In this case, the time series data of 2701 of FIG. 27 may satisfy some of the predetermined conditions.

As still another example, the biometric index obtaining device may determine whether the predetermined condition is satisfied, based on a difference between the lowest value and the highest value of the detailed time series data, for each of the plurality of detailed time series data. For example, the section of the detailed time series data may be divided into a plurality of detailed sections. For example, the section of the detailed time series data may be divided into a first detailed section from a time point to a time point corresponding to the highest value and a second detailed section from the time point to the end time point corresponding to the highest value. Of course, the first detailed section may be a section from the start time point to the intermediate time point, and the second detailed section may be a section from the intermediate time point to the end time point, without being limited thereto. In addition, the detailed sections may be divided into two or more sections. In addition, the biometric index obtaining device may obtain the highest value in the entire section of the detailed time series data, the lowest value in the first detailed section, and the lowest value in the second detailed section, and determine whether the detailed time series data satisfies the predetermined condition by using the obtained values. Referring to 2702 of FIG. 27, the x-axis of 2702 of FIG. 27 may indicate time, and the y-axis of 2702 of FIG. 27 may indicate a value of the detailed time series data. In FIG. 27, the first detailed section may indicate a section between the start time point 3051 and the time point 3052 corresponding to the maximum value 3062, and the second detailed section may indicate a section between the time point 3052 and the end time point 3053 corresponding to the maximum value 3062. The biometric index obtaining device may obtain the highest value 3062 in the entire section, the lowest value 3061 in the first detailed section, and the lowest value 3063 in the second detailed section. The biometric index obtaining device may compare the difference value h2 between the lowest value 3061 in the first subsection and the lowest value 3062 in the second subsection and the magnitude value h1 of the highest value 3062, and determine whether the detailed time series data satisfies a predetermined condition. For example, when the difference value h2 between the lowest value 3061 in the first subsection and the lowest value 3062 in the second subsection is ⅓ times the magnitude value h1 of the highest value 3062, the biometric index obtaining device may determine that the detailed time series data satisfies at least some of the predetermined conditions. Of course, the ratio is not limited to the ⅓ time, and various ratio values may be used for satisfying the predetermined condition of the detailed time series data.

Figure 28:
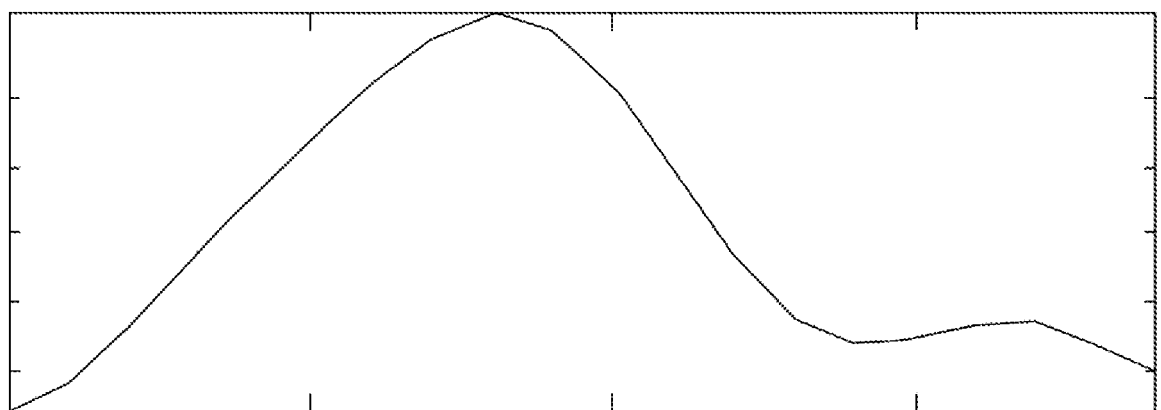
FIG. 28 is a diagram illustrating target time series data according to an embodiment.

When the detailed time series data satisfies at least some of the predetermined conditions described above, the biometric index obtaining device may select the detailed time series data as the target time series data. For example, FIG. 28 is a diagram for describing target time series data according to an embodiment. Referring to FIG. 28, in the graph of FIG. 28, an x-axis may represent a time, and a y-axis may represent a value of the target time series data. The target time series data of FIG. 28 may satisfy the predetermined conditions described above. As described above, when the target time series data satisfies at least some of the predetermined conditions, it is highly likely that the target time series data is similar to the time series data obtained while the heart rate of the measured person is stable, and accordingly, the biometric index obtaining device may obtain a more accurate biometric index.

In addition, in an embodiment, the biometric index obtaining device may obtain biosignal characteristic data by using the target time series data satisfying at least some of the predetermined conditions together, or may obtain biosignal characteristic data by using at least some of the target time series data, or only one of the target time series data. For example, the biometric index obtaining device may obtain biosignal characteristic data from each of the target time series data, obtain biosignal characteristic data from one target time series data generated by using an average value of the target time series data, or obtain biosignal characteristic data from the target time series data initially obtained among the target time series data.

In addition, in an embodiment, the biometric index obtaining device may obtain biosignal characteristic data from the target time series data or the time series data.

In an embodiment, the biometric index obtaining device may obtain at least one numerical value from the target time series data or the time series data, and use the obtained numerical value as the biosignal characteristic data. Here, the biosignal characteristic data may be one or more.

Figure 29:
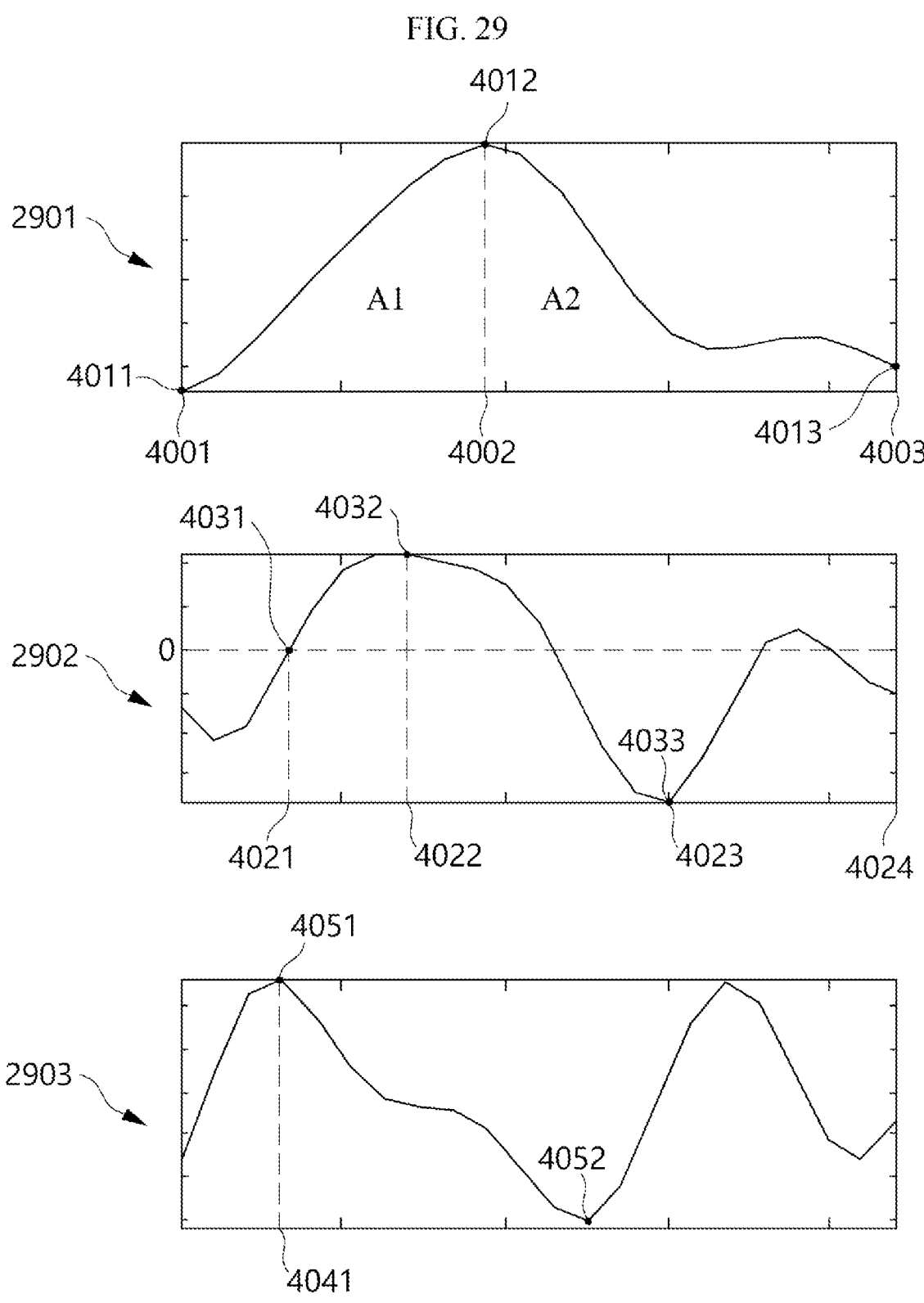
FIG. 29 is a diagram illustrating obtaining of biometric signal feature data according to an embodiment.

FIG. 29 is a diagram for describing obtaining of biosignal characteristic data according to an embodiment.

Referring to FIG. 29, 2901 of FIG. 29 may represent target time series data, 2902 of FIG. 29 may represent primary derivative data obtained by subjecting the target time series data to a first degree of differentiation, and 2903 of FIG. 29 may represent secondary derivative data obtained by subjecting the target time series data to a second degree of differentiation. In 2901 of FIG. 29, the x-axis may indicate time, the y-axis may indicate a value of the target time series data, in 2902 of FIG. 29, the x-axis may indicate time, the y-axis may indicate a value of the first differential data, and in 2903 of FIG. 29, the x-axis may indicate time, and the y-axis may indicate a value of the second differential data.

In an embodiment, the biometric index obtaining device may obtain biometric signal characteristic data from the target time series data. For example, in the target time series data of 2901 of FIG. 29, at least one of a value 4011 at a start time point 4001, a change amount of a value from the start time point 4001 to a time point 4002 corresponding to a maximum value 4012, an average change amount of a value from the start time point 4001 to the time point 4002 corresponding to the maximum value 4012, a value 4013 at an end time point 4003, a change amount of a value from the time point 4002 corresponding to the maximum value 4012 to the end time point 4003, an average change amount of a value from the time point 4002 corresponding to the maximum value 4012 to the end time point 4003, a width A1 of a graph corresponding to the target time series data from the start time point 4001 to the time point 4002 corresponding to the maximum value 4012, a width A2 of a graph corresponding to the target time series data from the time point 4002 corresponding to the maximum value 4012 to the end time point 4003, or a heart rate of a measured person may be included in the biometric signal characteristic data. Here, the heart rate of the measured person may be obtained based on the target time series data, obtained according to the heart rate obtaining process described above, or may be obtained separately from the target time series data. In addition, the target time series data may correspond to a tendency of a heart to contract and relax. For example, the start time point 4001 of the target time series data may correspond to a start time point of contraction of the heart, the time point 4002 corresponding to the maximum value 4012 may correspond to a maximum arrest time point of the heart, and the end time point 4003 may correspond to a lowest arrest time point of the heart. In addition, the average change amount of the value from the start time point 4001 to the time point 4002 corresponding to the maximum value 4012 may correspond to an average velocity of a blood flow from the time point 4001 to the time point 4002, and the average change amount of the value from the time point 4002 corresponding to the maximum value 4012 to the end time point 4003 may correspond to an average velocity of a blood flow from the time point 4002 to the end time point 4003.

In addition, in an embodiment, the biometric index obtaining device may obtain biometric signal characteristic data from the first differential data of the target time series data. For example, at least one of a maximum value 4032 of the first differential data of 2902 of FIG. 29, an average change amount between the time point 4021 where the value of the first differential data is 0 to the time point 4222 corresponding to the maximum value 4032, a lowest value 4033 between the time point 4222 corresponding to the maximum value 4032 and the end time point 4024 (or between the time point 4024 where the first differential data is intermediate) and an average change amount of a value from the time point 4022 corresponding to the highest value 4032 to the time point 4023 corresponding to the lowest value 4032 may be included in the biometric signal characteristic data. In addition, the first differential data may correspond to a tendency of a velocity of a blood flow. For example, the maximum value 4032 of the primary differential data may correspond to the highest velocity of the atrial systole, the average variation between the time point 4021 having the primary differential data value 0 and the time point 4222 corresponding to the maximum value 4032 may correspond to the average acceleration of the blood flow between the time point 4021 and the time point 4022, and the average variation between the time point 4022 corresponding to the highest value 4032 and the time point 4023 corresponding to the lowest value 4033 may correspond to the average acceleration of the blood flow between the time point 4022 and the time point 4023.

In addition, in an embodiment, the biometric index obtaining device may obtain biometric signal characteristic data from the secondary differential data of the target time sequence data. For example, at least one of the maximum value 4051 of the secondary differential data of 2903 of FIG. 29 and the lowest value 4052 after the time point 4041 corresponding to the maximum value 4051 may be included in the biometric signal characteristic data. In addition, the secondary differential data may correspond to an acceleration tendency of the blood flow. For example, the maximum value 4051 of the secondary differential data may correspond to the highest acceleration of the blood flow of the atrial systole, and the lowest value 4052 after the time point 4041 corresponding to the maximum value 4051 may correspond to the lowest acceleration after the highest acceleration of the blood flow.

In addition, in an embodiment, the biometric index obtaining device may input each of the obtained biometric signal characteristic data to the biometric index obtaining model, calculate an average value for each characteristic of the obtained biometric signal characteristic data, and input the calculated average values for each characteristic to the biometric index obtaining model.

In an embodiment, the biometric signal characteristic data may include image data obtained by imaging a graph of the target time sequence data or image data obtained by imaging a graph of the time sequence data. For example, the biometric index obtaining device may input the biometric index obtaining model to the image data obtained by imaging a graph of the target time sequence data or the image data obtained by imaging a graph of the time sequence data. In this case, the image data may include the target time sequence data itself or the image data obtained by imaging the time sequence data itself, and may also include the target time sequence data and the image data obtained by secondarily imaging the time sequence data to be suitable for processing the biometric index obtaining model.

Figure 30:
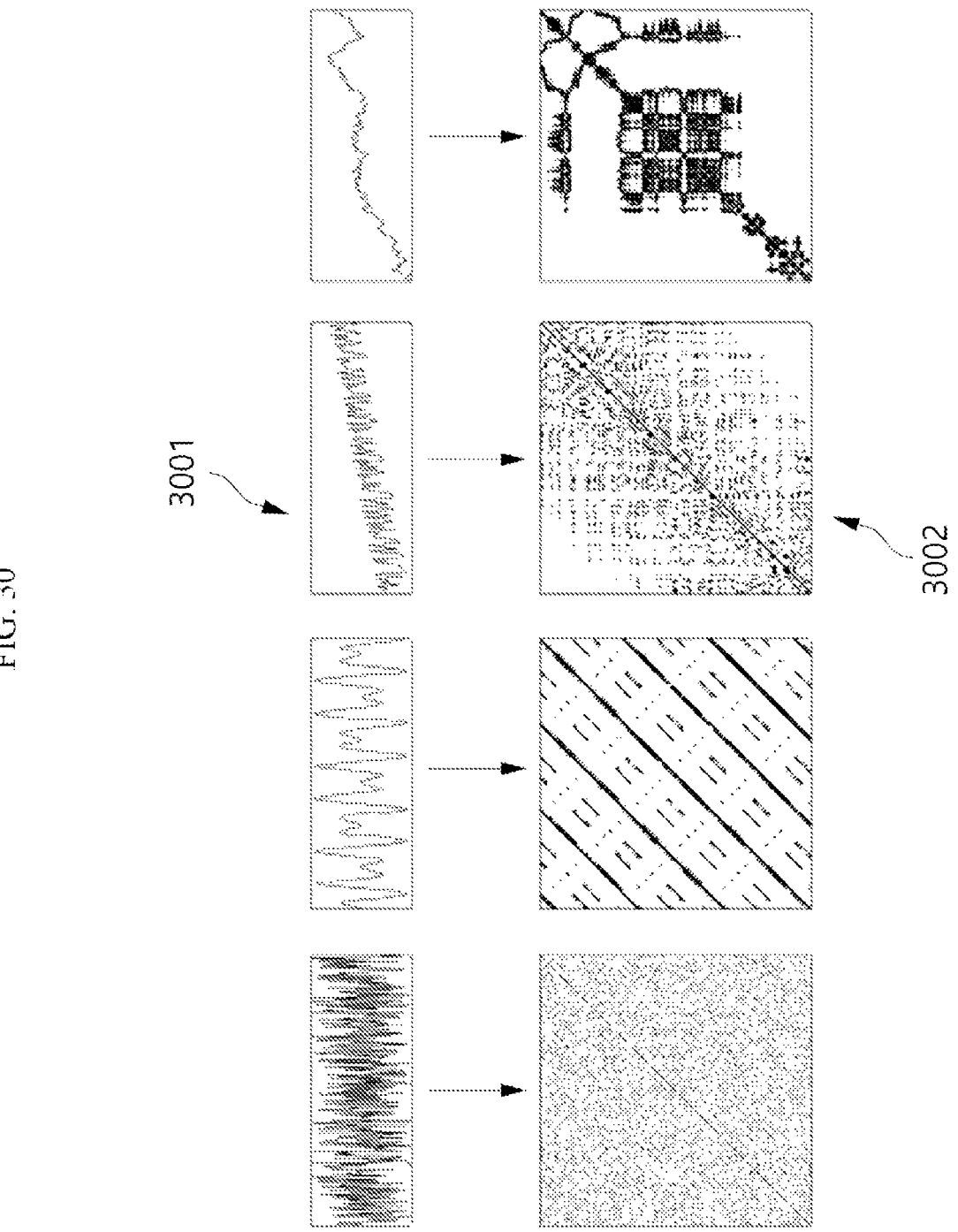
FIG. 30 is a diagram illustrating obtaining of image data according to an embodiment.

More specifically, FIG. 30 is a diagram for describing obtaining of image data according to an embodiment. Referring to FIG. 30, 3001 of FIG. 30 may represent time sequence data, and 3002 of FIG. 30 may represent image data obtained by secondarily imaging the time sequence data. For example, the biometric signal measurement device may generate the image data of 3002 of FIG. 30 for the time sequence data of 3001 of FIG. 30 using a recurrence plot, and may input the generated image data to the biometric index obtaining model. Of course, the biometric index obtaining device may obtain image data using a recurrence plot even for the target time sequence data, or may obtain image data using other methods than the recurrence plot. Of course, the biometric signal measurement device may obtain image data by imaging the time sequence data of 3001 of FIG. 30 without change.

In addition, in the step S2870 of obtaining the biometric index for the subject using the biometric index measurement model based on the biometric signal characteristic data, the biometric index obtaining device may obtain the biometric index for the subject by inputting the obtained biometric signal characteristic data or data obtained by processing the obtained biometric signal characteristic data to the biometric index obtaining model. Here, the obtained biometric index may be at least one of a heart rate, blood pressure (at least one of a highest blood pressure or a lowest blood pressure), oxygen saturation, and a heart rate. In addition, various biometric indices (such as a stress index) may be obtained. Hereinafter, for convenience of description, an embodiment in which the obtained biometric index is blood pressure (at least one of a highest blood pressure or a lowest blood pressure) will be described, but the embodiment is not limited thereto.

As described above, the biometric index measurement model may be implemented by a machine learning method. For example, the biometric index obtaining model may be a model implemented through supervised learning, but is not limited thereto, and may be a model implemented through non-supervised learning, semi-supervised learning, reinforcement learning, and the like. In addition, the biometric index obtaining model according to an embodiment may be implemented as an artificial neural network (ANN). For example, the biometric index obtaining model may be implemented as a forward neural network, a radial basis function network, a cohonen self-organizing network, and the like, but is not limited thereto.

In addition, the biometric index obtaining model according to an embodiment may be implemented as a deep neural network (DNN). For example, the biometric index obtaining model may be implemented as a convolutional neural network (CNN), a recursive neural network (RNN), a long short term memory network (LSTM), a gated recurrent units (GRUs), and the like, but is not limited thereto.

In an embodiment, as described above, the raw blood signal feature data may be a numerical value generated based on the target time series data or the time series data. In this case, the biometric index obtaining device may input at least a part or the entirety of the numerical values to the biometric index obtaining model, and may output blood pressure data (at least one of a highest blood pressure or a lowest blood pressure) from the biometric index obtaining model. For example, 15 biometric signal feature data may be input to the biometric index obtaining model. In this case, the biometric index obtaining model may include five hidden layers, and an activation function of the hidden layer may be ReLU, and an activation function for a final result value may be Linear. In addition, blood pressure (at least one of a highest blood pressure or a lowest blood pressure) data may be output from the biometric index obtaining model.

In addition, in another embodiment, as described above, the raw blood signal feature data may be image data generated based on the target time series data or the time series data. In this case, the biometric index obtaining model may be configured with various models such as a CNN. The biometric index obtaining model may be trained in advance using image data obtained by the target time series data or the time series data. In addition, the biometric index obtaining device may obtain blood pressure data (at least one of a highest blood pressure or a lowest blood pressure) by inputting the image data to the biometric index obtaining model.

The above-described matters in FIGS. 7 and 8 may be applied to the biometric index obtaining model and the biometric index obtaining using the biometric index obtaining model, and thus a detailed description thereof will be omitted.

The method according to the embodiment may be implemented in a form of a program instruction that may be executed by various computer means and recorded in a computer-readable medium. The computer-readable medium may include program instructions, data files, data structures, and the like, alone or in combination. The program instructions recorded in the medium may be specially designed and configured for the embodiment or may be used by those skilled in the art of computer software. Examples of the computer-readable recording medium include magnetic media such as hard disks, floppy disks, and magnetic tapes, optical media such as CD-ROMs and DVDs, magneto-optical media such as floptical disks, and hardware devices specially configured to store and execute program instructions such as ROMs, RAMs, and flash memories. Examples of the program instructions include machine codes such as those made by a compiler, and higher-level language codes that can be executed by a computer using an interpreter. The above-described hardware devices may be configured to operate as one or more software modules to perform operations of the embodiment, and vice versa.

Although the embodiments have been described above with reference to the limited embodiments and the drawings, various modifications and variations may be made from the above descriptions by those skilled in the art. For example, although the described techniques are performed in a different order from the described method, and/or the components such as the described system, structure, device, and circuit are combined or substituted by a different form from the described method, or by other components or equivalents, appropriate results may be achieved.

Therefore, other implementations, equivalents to other embodiments and claims fall within the scope of the following claims.

What is claimed is:

1. A method of measuring a biometric index of a subject using an artificial neural network in a non-contact manner, performed by one or more processors, the method comprising:

obtaining a plurality of image frames of the subject;

obtaining a first color channel value, a second color channel value, and a third color channel value for at least one image frame included in the plurality of image frames;

calculating a first difference value and a second difference value based on the first color channel value, the second color channel value, and the third color channel value for at least one image frame included in the plurality of image frames, wherein the first difference value is a difference value between the first color channel value and the second color channel value for a same image frame, and the second difference value indicates a difference value between the first color channel value and the third color channel value for the same image frame;

obtaining a first characteristic value based on the first difference value for at least one image frame included in a first image frame group for a first image frame group obtained for a first predetermined time;

obtaining a second characteristic value based on the second difference value for at least one image frame included in the first image frame group;

obtaining time series data based on the first characteristic value and the second characteristic value; obtaining biosignal characteristic data based on the time series data; and obtaining a biometric index of the subject using a biometric index obtaining model based on the biosignal characteristic data.

2. The method of claim 1, wherein obtaining biosignal characteristic data based on the time series data comprises:

filtering the time series data using a band pass filter; and obtaining the biosignal characteristic data using the filtered time series data.

3. The method of claim 2, wherein filtering the time series data using the band pass filter comprises:

filtering the time series data using a band pass filter having a frequency band corresponding to a heart rate of the subject.

4. The method of claim 1, wherein filtering the time series data using a band pass filter corresponding to a heart rate of the subject comprises:

performing Fourier transform on the time series data to extract a frequency band corresponding to the heart rate of the subject.

5. The method of claim 1, wherein obtaining biosignal characteristic data based on the time series data comprises:

dividing the time series data into a plurality of detailed time series data; and extracting target time series data based on the divided time series data, wherein the target time series data comprises a first maximum value and a second maximum value smaller than the first maximum value.

6. The method of claim 5, wherein the biosignal characteristic data is generated based on at least one of a value at a start time point of the target time series data, the first maximum value, and a value at an end time point of the target time series data.

7. The method of claim 5, wherein the biosignal characteristic data is generated based on time series data obtained by first differentiating the target time series data and time series data obtained by second differentiating.

8. The method of claim 1, wherein the biometric index of the subject comprises at least one of a lowest blood pressure or a highest blood pressure of the subject.

9. The method of claim 1, wherein the first, second, and third color channels are color channels according to an RGB color space.

10. The method of claim 9, wherein the first color channel is set to a Green channel, the second color channel is set to a Red channel, and the third color channel is set to a Blue channel.

11. The method of claim 1, wherein the first characteristic value is obtained based on a first deviation value of the first difference value for at least one image frame included in the first image frame group, wherein the second characteristic value is obtained based on a second deviation value of the second difference value for at least one image frame included in the first image frame group, wherein the first deviation value is calculated based on a first difference value for the at least one image frame and an average value of the first difference value for the first image frame group, and wherein the second deviation value is calculated based on a second difference value for the at least one image frame and an average value of the second difference value for the first image frame group.

12. The method of claim 11, wherein the first characteristic value and the second characteristic value are normalized values.

13. The method of claim 12, wherein the first characteristic value is a value normalized by a first standard deviation value, and the second characteristic value is a value normalized by a second standard deviation value, wherein the first standard deviation value is a standard deviation value of the first difference value for the first image frame group, and the second standard deviation value is a standard deviation value of the second difference value for the first image frame group.

14. The method of claim 1, wherein the time series data is obtained based on third characteristic data obtained as a sum of the first characteristic value and the second characteristic value.

15. A non-transitory computer-readable storage medium storing instructions thereon, the instructions, when executed by a processor cause the processor to:

obtaining a plurality of image frames of a subject;

obtain a first color channel value, a second color channel value, and a third color channel value for at least one image frame included in the plurality of image frames;

calculate a first difference value and a second difference value based on the first color channel value, the second color channel value, and the third color channel value for at least one image frame included in the plurality of image frames, wherein the first difference value is a difference value between the first color channel value and the second color channel value for a same image frame, and the second difference value indicates a difference value between the first color channel value and the third color channel value for the same image frame;

obtain a first characteristic value based on the first difference value for at least one image frame included in a first image frame group for a first image frame group obtained for a first predetermined time;

obtain a second characteristic value based on the second difference value for at least one image frame included in the first image frame group;

obtain time series data based on the first characteristic value and the second characteristic value; obtaining biosignal characteristic data based on the time series data; and obtain a biometric index of the subject using a biometric index obtaining model based on the biosignal characteristic data.

* * * * *